(12) United States Patent
Meng et al.

(10) Patent No.: US 9,897,605 B2
(45) Date of Patent: Feb. 20, 2018

(54) PORCINE TORQUE TENO VIRUS VACCINES AND DIAGNOSIS

(71) Applicant: Virginia Tech Intellectual Properties, Inc., Blacksburg, VA (US)

(72) Inventors: Xiang-Jin Meng, Blacksburg, VA (US); Yaowei Huang, Blacksburg, VA (US)

(73) Assignee: Virginia Tech Intellectual Properties, Inc., Blacksburg, VA (US)

( * ) Notice: Subject to any disclaimer, the term of this patent is extended or adjusted under 35 U.S.C. 154(b) by 77 days.

(21) Appl. No.: 14/946,384

(22) Filed: Nov. 19, 2015

(65) Prior Publication Data
US 2016/0216263 A1 Jul. 28, 2016

Related U.S. Application Data

(63) Continuation of application No. 12/861,378, filed on Aug. 23, 2010, now Pat. No. 9,228,242.

(60) Provisional application No. 61/316,519, filed on Mar. 23, 2010, provisional application No. 61/235,833, filed on Aug. 21, 2009.

(51) Int. Cl.
| | | |
|---|---|---|
| G01N 33/569 | (2006.01) | |
| C07K 16/08 | (2006.01) | |
| C12Q 1/70 | (2006.01) | |
| A61K 39/12 | (2006.01) | |
| C07K 14/005 | (2006.01) | |
| C12N 7/00 | (2006.01) | |
| A61K 39/00 | (2006.01) | |

(52) U.S. Cl.
CPC ....... *G01N 33/56983* (2013.01); *A61K 39/12* (2013.01); *C07K 14/005* (2013.01); *C07K 16/081* (2013.01); *C12N 7/00* (2013.01); *C12Q 1/701* (2013.01); *A61K 2039/552* (2013.01); *C12N 2750/00021* (2013.01); *C12N 2750/00022* (2013.01); *C12N 2750/00034* (2013.01); *C12N 2750/14034* (2013.01); *G01N 2333/01* (2013.01); *G01N 2333/085* (2013.01); *G01N 2469/20* (2013.01)

(58) Field of Classification Search
CPC .................. C12N 7/00; C12N 2750/00; C12N 2750/00021; C12N 2750/14034; C07K 14/005

See application file for complete search history.

(56) References Cited

U.S. PATENT DOCUMENTS

2011/0045019 A1 2/2011 Meng et al.

FOREIGN PATENT DOCUMENTS

| WO | WO-2008127279 A2 | 10/2008 |
|---|---|---|
| WO | WO-2008150275 A2 | 12/2008 |
| WO | WO-2010044889 A2 | 4/2010 |

OTHER PUBLICATIONS

Huang YW, Meng XJ. ORF1 protein [Torque teno sus virus 1 b]. GenBank: ADD46854.1.*
Fenaux M, et al. "Cloned Genomic DNA of Type 2 Porcine Circovirus is Infectious When Injected Directly into the Liver and Lymph Nodes of Pigs: Characterization of Cinical Disease, Virus Distribution, and Pathologic Lesions" Journal of Virology 76 (2) (2002) 541-551.
Genbank AB076001 SD-TTV32.
Genbank AF298585 TTV Polish isolate.
Genbank AY823991 TTSuVk2 isolate 2p.
Huang, Y-W, et al. "Serological Profile of Torque Teno Sus Virus Species 1 (TTSuV1) in Pigs and Antigenic Relationships between Two TTSuV1 Genotypes (1a and 1b), between Two Species (TTSuV1 and -2), and between Porcine and Human Anellovirueses" Journal of Virology 86 (19) (2012) 10628-10639.
Huang, Y-W, et al. "Rescue of a Porcine Anellovirus (Torque Teno Sus Virus 2) from Cloned Genomic DNA in Pigs" Journal of Virology 86 (11) (2012) 6042-6054.
Taira, O, et al. "Prevalence of swine Torque teno virus genotypes 1 and 2 in Japanese swine with suspected post-weaning multisystemic wasting syndrome and porcine respiratory disease complex" Veterinary Microbiology 139 (2009) 347-350.

(Continued)

*Primary Examiner* — Rachel B Gill
(74) *Attorney, Agent, or Firm* — Blank Rome LLP; Michael C. Greenbaum

(57) ABSTRACT

The present invention provides four purified preparation containing a polynucleic acid molecule encoding porcine Torque teno virus (PTTV) genotypes or subtypes PTTV1a-VA, PTTV1b-VA, PTTV2b-VA, and PTTV2c-VA. The present invention also provides infectious DNA clones, biologically functional plasmid or viral vector containing the infectious nucleic acid genome molecule of the same. The present invention further provides live, attenuated, vector-expressed and purified recombinant capsid subunit or killed viral vaccines for protection against PTTV infection. The present invention additionally provides subunit vaccines comprising PTTV specific gene products, especially ORF1 capsid gene product for protection against PTTV infection. Further, the present invention provides methods for diagnosing PTTV infection via polymerase chain reaction (PCR) using specific primer for PTTV1, PTTV2, and individual PTTV1 genotypes. Finally, the present invention provides methods for diagnosing PTTV infection via immunological methods, e.g., enzyme-linked immunoabsorbent assay (ELISA) and Western blot using PTTV specific antigens for detecting serum PTTV specific antibodies.

11 Claims, 31 Drawing Sheets

(56) References Cited

OTHER PUBLICATIONS

Okamoto, et al., "Genomic characterization of TT viruses (TTVs) in pigs, cats and dogs and their relatedness with species-specific TTVs in primates and tupalas". Journal of General Virology, 2002, (83), 1291-1297.
Biagini, P., M. Bendinelli, S. Hino, L. Kakkola, A. Mankertz, C. Niel, H. Okamoto, S. Raidal, C. G. Teo, and D. Todd. 2011. Anelloviridae, p. 331-341.
Ninomiya, M. M., et al., "Development of PCR assays with nested primers specific for differential detection of three human anelloviruses and early acquisition of dual or triple infection during infancy." J Clin. Microbiol 46, pp. 507-514, 2008.
Huang, Y.W. et al., Multiple infection of porcine Torque teno virus in a single pig and characterization of the full-length genomic sequences of four U.S. prototype PTTV strains: Implication for genotyping of PTTV, Nov. 2009, p. 289-297, Virology, vol. 396.
Niel, et al., "Rolling-circle amplification of Torque teno virus (TTV) complete genomes from human and swine sera and identification of a novel swine TTV genogroup". Journal of General Virology, 2005, pp. 1343-1347, vol. 86, Pt. 5.
Huang, Y. W., et al., "Expression of the putative ORF1 capsid protein of Torque teno sus virus 2 (TTSuV2) and development of Western blot and ELISA serodiagnostic assays: correlation between TTSuV2 viral load and IgG antibody level in pigs," Virus Res 158, pp. 79-88, 2011.
Kakkola, L., et al., "Expression of all six human Torque teno virus (TTV) proteins in bacteria and in insect cells, and analysis of their IgG responses" Virology 382, pp. 182-189, 2008.
Ott, C., et al., Use of a TT virus ORF1 recombinant protein to detect anti-TT virus antibodies in human sera, J Gen Virol 81, pp. 2949-2958, 2000.
Ellis, et al., "Effect of coinfection with genogroup 1 porcine torque teno virus on porcine circovirus type 2-associated postweaning multisystemic wasting syndrome in gnotobiotic pigs". American Journal of Veterinary Research, Dec. 2008, pp. 1608-1614, vol. 69, Issue 12, Schaumburg, IL.
Aramouni, M., et al., Torque teno sus virus 1 and 2 viral loads in postweaning multisystemic wasting syndrome (PMWS) and porcine dermatitis and nephropathy syndrome (PDNS) affected pigs, Vet Microbiol 153, pp. 377-381, 2011.
Gauger, P. C., et al., "Postweaning multisystemic wasting syndrome produced in gnotobiotic pigs following exposure to various amounts of porcine circovirus type 2a or type 2b," Vet Microbiol 153, pp. 229-239, 2011.
Huang, Y. W., et al., "Serological profile of Torque teno sus virus species 1 (TTSuV1) in pigs and antigenic relationships between two TTSuV1 genotypes (1a and 1b), between two species (TTSuV1 and 2), and between porcine and human anelloviruses," J. Virol., Submitted Manuscript, 2012.
Lee, S. S., et al. "Quantitative detection of porcine Torque teno virus in Porcine circovirus-2-negative and Porcine circovirus-associated disease-affected pigs," J Vet Diagn Invest 22, pp. 261-264, 2010.
Ninomiya, M., et al., "Development of PCR assays with nested primers specific for differential detection of three human anelloviruses and early acquisition of dual or triple infection during infancy." J Clin Microbiol 46, pp. 507-514, 2008.
De Villiers, E. M., et al., "The diversity of torque teno viruses: in vitro replication leads to the formation of additional replication-competent subviral molecules," J Virol 85, pp. 7284-7295, 2011.
Kakkola, L., et al., "Construction and biological activity of a full-length molecular clone of human Torque teno virus (TTN) genotype6," FEBS J 274, pp. 4719-4730, 2007.
Leppik, L., et al., "In vivo and in vitro intragenomic rearrangement of TT viruses," J Virol 81, pp. 9346-9356, 2007.
Ball, J.K., et al., "TT virus sequence heterogeneity in vivo: evidence for co-infection with multiple genetic types," J Gen Virol 80, Pt 7, pp. 1759-1768, 1999.

Forns, X., et al., "High prevalence of TT virus (TTV) infection in patients on maintenance hemodialysis: frequent mixed infections with different genotypes and lack of evidence of associated liver disease," J Med Virol 59, pp. 313-317, 1999.
Pesch, W., et al., "Porcine Torque teno virus: determination of viral genomic loads by genogroup-specific multiplex rt-PCR, detection of frequent multiple infections with genogroups 1 or 2, and establishment of viral full-length sequences," Vet Microbiol 143, pp. 202-212, 2010.
Finsterbusch, et al., "Gene expression of the human Torque Teno Virus isolate P/1C1," Virology 381, pp. 36-45, 2008.
Teixeira, T. F., et al., "Torque teno sus virus (TTSuV) in cell cultures and trypsin," PLoS One 6:e17501, 2011.
Beach, N. M., et al., "Productive infection of human hepatocellular carcinoma cells by porcine circovirus type 1," Vaccine 29, pp. 7303-7306, 2011.
Hattermann, K., et al., "Infection studies on human cell lines with porcine circovirus type 1 and porcine circovirus type 2," Xenotransplantation 11, pp. 284-294, 2004.
Ma, H., et al., "Investigations of porcine circovirus type 1 (PCV1) in vaccine-related and other cell lines," Vaccine 29, pp. 8429-8437, 2011.
Tischer, I., et al., "A very small porcine virus with circular single-stranded DNA," Nature 295, pp. 64-66, 1982.
Kekarainen, T., et al. "Swine torque teno virus detection in pig commercial vaccines, enzymes for laboratory use and human drugs containing components of porcine origin," J Gen Virol 90, pp. 648-653, 2009.
Mueller, B., et al., "Gene expression of the human Torque Teno Virus isolate P/1C1," Virology 381, pp. 36-45, 2008.
Martinez-Guino, L., et al., "Expression profile and subcellular localization of Torque teno sus virus proteins," J Gen Virol 92, pp. 2446-2457, 2011.
Miyata, H., et al. "Identification of a novel GC-rich 113-nucleotide region to complete the circular, single-stranded DNA genome of TT virus, the first human circovirus," J Virol 73, pp. 3582-3586, 1999.
Okamoto, H., et al., "The entire nucleotide sequence of a TT virus isolate from the United States (TUS01): comparison with reported isolates and phylogenetic analysis," Virology 259, pp. 437-448, 1999.
Huang, Y. W., et al., "Development of SYBR green-based real-time PCR and duplex nested PCR assays for quantitation and differential detection of species- or type-specific porcine Torque teno viruses," J Virol Methods 170, pp. 140-146, 2010.
Crowther, R. A., et al., "Comparison of the structures of three circoviruses: chicken anemia virus, porcine circovirus type 2, and beak and feather disease virus," J Virol 77, pp. 13036-13041, 2003.
Handa, A., et al. "Prevalence of the newly described human circovirus, TTV, in United States blood donors," Transfusion 40, pp. 245-251, 2000.
Zoller et al., DNA 3, pp. 479-488, 1984.
Fenaux, M., et al., "A chimeric porcine circovirus (PCV) with the immunogenic capsid gene of the pathogenic PCV type 2 (PCV2) cloned into the genomic backbone of the nonpathogenic PCV1 induces protective immunity against PCV2 infection in pigs," J Virol 78, pp. 6297-6303, 2004.
Halbur, P. G., et al. "Comparison of the pathogenicity of two US porcine reproductive and respiratory syndrome virus isolates with that of the Lelystad virus," Vet Pathol 32, pp. 648-660, 1995.
Ritterbusch, G.A., et al. "Natural Co-Infection of Torque Teno Virus and Porcine Circovirus 2 in the Reproductive Apparatus of Swine," Res. Vet Sci., 2011.
Huang, Y.W., et al., "Rescue of a Porcine Anellovirus (Torque teno sus virus 2) from Cloned Genomic DNA in Pigs," J. Virol. Submitted Manuscript, 2012.
O'Reilly et al., "Baculovirus Expression Vectors: A Lab Manual," Freeman & Co., 1995.
Schierack, P., "Characterization of a Porcine Intestinal Epithelial Cell Line for In Vitro Studies of Microbial Pathogenesis in Swine," Histochem. Cell Biology 125, pp. 293-305, 2006.
Emerson, S.U., et al. "In Vitro Replication of Hepatitis E Virus (HEV) Genomes and of an HEV Replicon Expressing Green Fluorescent Protein," J. Virol. 78, pp. 4838-4846, 2004.

(56) References Cited

OTHER PUBLICATIONS

Buck, C.B. et al., "Efficient Intracellular Assembly of Papillomaviral Vectors," J. Virol. 78, pp. 751-757, 2004.
Anderson, et al., "Failure to genotype herpes simplex virus by real-time PCR assay and melting curve analysis due to sequence variation within probe binding sites". Journal of Clinical Microbiology, 2003, pp. 2135-2137 vol. 41, American Society for Microbiology.
Bao, et al., "Virus Classification by Pairwise Sequence Comparison (PASC)", 2008, pp. 342-348, vol. 5, Elsevier Ltd. Oxford, U.K.
Biagini, et al., "Classification of TTV and related viruses (anelloviruses)". Current Topics in Microbiology Immunology, 2009, pp. 21-33, vol. No. 331, Springer-Verlag Berlin Heidelberg.
Biagini, et al., "Distribution and genetic analysis of TTV and TTMV major phylogenetic groups in French blood donors". Journal of Medical Virology, 2006, pp. 298-304, vol. No. 78, Issue No. 2, Journal of Medical Virology, Marseille, France.
Biagini, et al., "Circular genomes related to anelloviruses identified in human and animal samples by using a combined rolling-circle amplification/sequence-independent single primer amplification approach". Journal of General Virology, 2007, pp. 2696-2701, vol. 88, Pt 10, Marseille, France.
Brassard, et al., "Development of a real-time TaqMan PCR assay for the detection of porcine and bovine Torque teno virus", Journal of Applied Microbiology, Agriculture and Agri-food Canada, Nov. 2009, pp. 2191-2198, Food Research and Development Centre, Saint-Hyacinthe, QC, Canada.
Davidson, et al., "Unraveling the puzzle of human anellovirus infections by comparison with avian infections with the chicken anemia virus", Virus Research, 2008, pp. 1-15, vol. 137, Issue 1, Israel.
De Smit, et al., "Apoptosis-inducing proteins in chicken anemia virus and TT virus". Current Topics in Microbiology and Immunology, 2009, pp. 131-149, vol. 331.
Gallei, et al., "Porcine Torque teno virus: Determination of viral genomic loads by genogroup-specific multiplex rt-PCR, detection of frequent multiple infections with genogroups 1 or 2, and establishment of viral full-length sequences". Veterinary Microbiology, 2010, pp. 202-212, vol. 143, Veterinary Microbiology, Munster, Germany.
Gibellini, et al., "Simultaneous detection of HCV and HIV-1 by SYBR Green real time multiplex RT-PCR technique in plasma samples". Molecular and Cellular Probes, Mar. 2006, pp. 223-229, vol. 20.
Hino, et al., "Torque teno virus (TTV): current status". Reviews in Medical Virology, 2007, pp. 45-57, vol. 17, Wiley Interscience.
Hino, et al., "Relationship of Torque teno virus to chicken anemia virus". Current Topics in Microbiology and Immunology, 2009, pp. 117-130, vol. 331, Springer Verlag Berlin Heidelberg.
Ilyina, et al., "Conserved sequence motifs in the initiator proteins for rolling circle DNA replication encoded by diverse replicons from eubacteria, eucaryotes and archaebacteria". Nucleic Acids Research, pp. 3279-3285, vol. 20, No. 13, NIH, Bethesda, MD.
Inami, et al., "Full-length nucleotide sequence of a simian TT virus isolate obtained from a chimpanzee: evidence for a new TT virus-like species". Virology, 2000, pp. 330-335, vol. 277, No. 2, Academic Press.
Jelcic, et al., "Isolation of multiple TT virus genotypes from spleen biopsy tissue from a Hodgkin's disease patient: genome reorganization and diversity in the hypervariable region". Journal of Virology, 2004, pp. 7498-7507, vol. 78, No. 14, American Society for Microbiology.
Kakkola, et al., "Replication of and protein synthesis by TT viruses". Current Topics in Microbiology and Immunology, 2009, pp. 53-64, vol. 331, Springer Verlag Berlin Heidelberg.
Kekarainen, et al., "Detection of swine Torque teno virus genogroups 1 and 2 in boar sera and semen". Theriogenology, 2007, pp. 966-971, vol. 68, No. 7.
Kekarainen, et al., "Prevalence of swine Torque teno virus in post-weaning multisystemic wasting syndrome (PMWS)-affected and non-PMWS-affected pigs in Spain". Journal of General Virology, 2006, pp. 833-837, vol. 87, Part 4, UK.
Krakowka, et al., "Evaluation of the effects of porcine genogroup 1 torque teno virus in gnotobiotic swine". American Journal of Veterinary Research, 2008, pp. 1623-1629, vol. 69.
Krakowka, et al., "Evaluation of induction of porcine dermatitis and nephropathy syndrome in gnotobiotic pigs with negative results for porcine circovirus type 2". American Journal of Veterinary Research, 2008, pp. 1615-1622, vol. 69, Part 12.
Maggi, et al., "Immunobiology of the Torque teno viruses and other anelloviruses". Current Topics in Microbiology and Immunology, 2009, pp. 65-90, vol. 331.
Martinez, "Simultaneous detection and genotyping of porcine reproductive and respiratory syndrome virus (PRRSV) by real-time RT-PCR and amplicon melting curve analysis using SYBR Green". Research in Veterinary Science, 2008, pp. 184-193 vol. 85, Issue 1.
McKeown, et al., "Molecular characterization of porcine TT virus, an orphan virus, in pigs from six different countries". Veterinary Microbiology, 2004, pp. 113-117, vol. 104, Issues 1-2.
Mouillesseaux, et al., Improvement in the specificity and sensitivity of detection for the Taura syndrome virus and yellow head virus of penaeid shrimp by increasing the amplicon size in SYBR Green real-time RT-PCR. Journal of Virological Methods, 2003, pp. 121-127, vol. 111, Issue 2.
Mueller, et al., "Gene expression of the human Torque Tena Virus isolate P/1C1" Virology, 2008, pp. 36-45, vol. 381, Issue 1.
Ng, et al., "Novel anellovirus discovered from a mortality event of captive California sea lions". Journal of General Virology, 2009, pp. 1256-1261, vol. 90, Pt 5.
Niel, et al., "Coinfection with multiple TT virus strains belonging to different genotypes is a common event in healthy Brazilian adults". Journal of Clinical Microbiology, 2000, pp. 1926-1930, vol. 38, No. 5.
Ninomiya, et al., "Analysis of the entire genomes of torque teno midi virus variants in chimpanzees: infrequent cross-species infection between humans and chimpanzees". Journal of General Virology, 2009, pp. 347-358, vol. 90, Pt 2.
Nishizawa, et al., "A novel DNA virus (TTV) associated with elevated transaminase levels in posttransfusion hepatitis of unknown etiology". Biochemical Biophysical Research Communications, 1997, pp. 92-97, vol. 241, No. 1.
Okamoto, et al., "History of discoveries and pathogenicity of TT viruses". Current Topics in Microbiology and Immunology, 2009, pp. 1-20, vol. 331.
Okamoto, et al., "TT viruses in animals". Current Topics in Microbiology and Immunology, 2009, pp. 35-52, vol. 331.
Okamoto, et al., "Genomic and evolutionary characterization of TT virus (TTV) in tupaias and comparison with species-specific TTVs in humans and non-human primates". Journal of General Virology, 2001, pp. 2041-2050, vol. 82, Pt 9.
Okamoto, et al., "Species-specific TT viruses in humans and non-human primates and their phylogenetic relatedness". Virology, 2000, pp. 368-378,vol. 277, No. 2.
Okamoto, et al., "TT virus mRNAs detected in the bone marrow cells from an infected individual". Biochemical and Biophysical Research Communications. 2000, pp. 700-707, vol. 279, No. 2.
Okamoto, et al., "Genomic characterization of TT viruses (TTVs) in pigs, cats and dogs and their relatedness with species-specific TTVs in primates and tupaias". Journal of General Virology, 2002, pp. pp. 700-707, vol. 83, Pt 6.
Opriessnig, et al., "Porcine circovirus type 2 associated disease: update on current terminology, clinical manifestations, pathogenesis, diagnosis, and intervention strategies". Journal of Veterinary Diagnostic Investestigation, 2007, pp. 591-615, vol. 19.
Pal, et al., "Development and validation of a duplex real-time PCR assay for the simultaneous detection and quantification of porcine circovirus type 2 and an internal control on porcine semen samples". Journal of Virological Methods, 2008, pp. 217-225, vol. 149.
Peters, et al., "Attenuation of chicken anemia virus by site-directed mutagenesis of VP2". Journal of General Virology, 2007, pp. 2168-2175, vol. 88, Pt. 8.

(56) References Cited

OTHER PUBLICATIONS

Peters, et al., "Site-directed mutagenesis of the VP2 gene of Chicken anemia virus affects virus replication, cytopathology and host-cell MHC class I expression". Journal of General Virology, 2006, pp. 823-831, vol. 87, Pt. 4.

Peters, et al., "Chicken anemia virus VP2 is a novel dual specificity protein phosphatase". Journal of Biological Chemistry, 2002, pp. 39566-39573, vol. 277, No. 42.

Pozzuto, et al., "In utero transmission of porcine torque teno viruses". Veterinary Microbiology, 2009, pp. 375-379, vol. 137.

Prasetyo, et al., "Replication of chicken anemia virus (CAV) requires apoptin and is complemented by VP3 of human torque teno virus (TTV)". Virology, 2009, pp. 85-92, vol. 385, No. 1.

Qiu, et al., "Human circovirus TT virus genotype 6 expresses six proteins following transfection of a full-length clone". Journal of Virology, 2005, pp. 6505-6510, vol. 79, No. 10.

Ririe, et al., "Product differentiation by analysis of DNA melting curves during the polymerase chain reaction". Analytical Biochemistry, 1997, pp. 154-160, vol. 245.

Sibila, et al., "Swine torque teno virus (TTV) infection and excretion dynamics in conventional pig farms". Veterinary Microbiology, 2009, pp. 213-228, vol. 139.

Takayama, et al., "Prevalence and persistence of a novel DNA TT virus (TTV) infection in Japanese haemophiliacs". British Journal of Haematology, 1999, vol. 104, No. 3, pp. 626-629.

Wilhelm, et al., "Real-time PCR protocol for the detection of porcine parvovirus in field samples". Journal of Virological Methods, 2006, pp. 257-260, vol. 134.

Genbank; GU456383.1.
Genbank; GU456384.1.
Genbank; GU456385.1.
Genbank; GU456386.1.

* cited by examiner

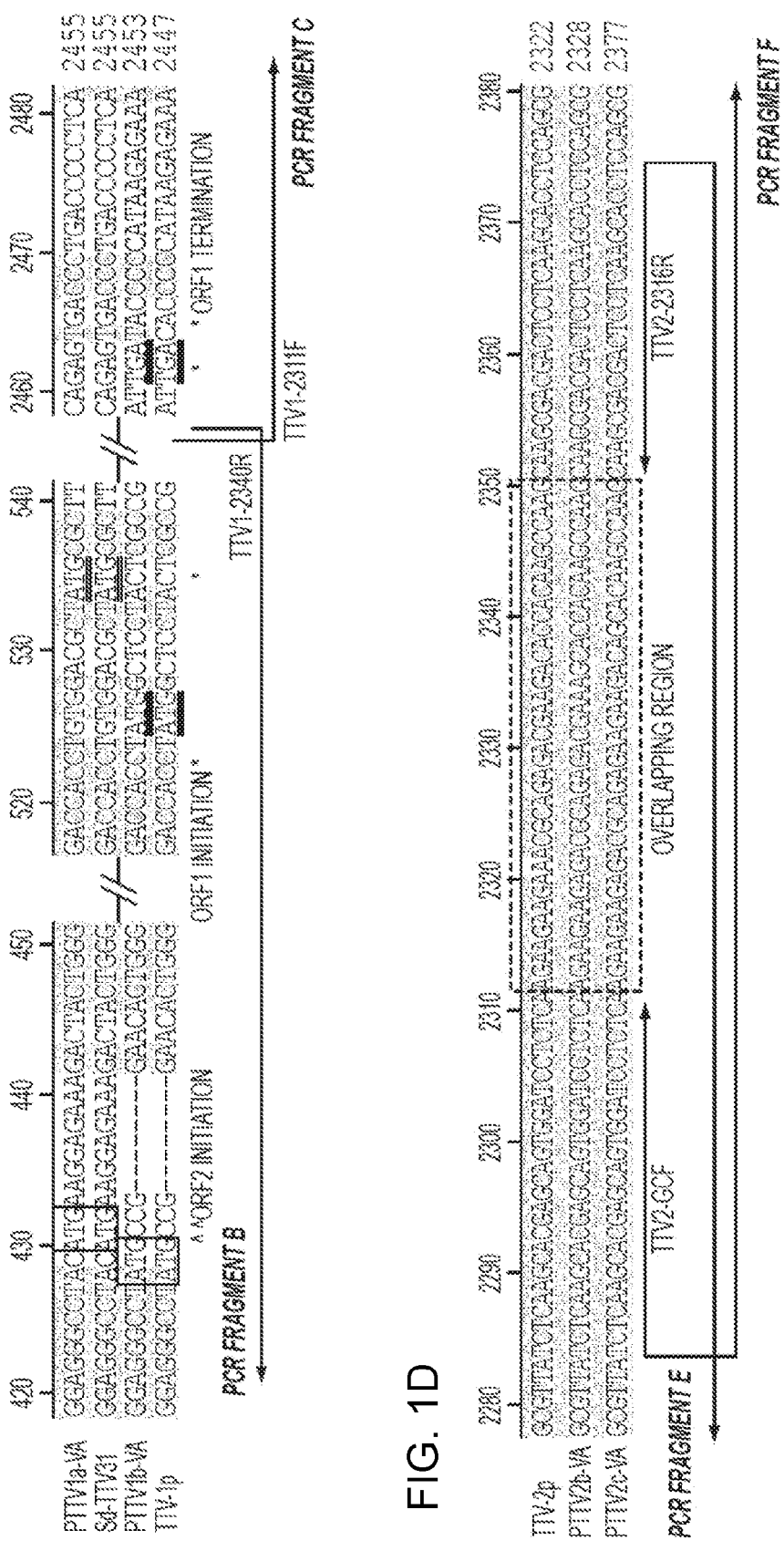

DOMAIN I

```
                  322                                         349
                   |                                           |
CONSENSUS         SEQDIKKLAHDQXIAREYARDPKSKKKLK
PTTV2c-VA         ..

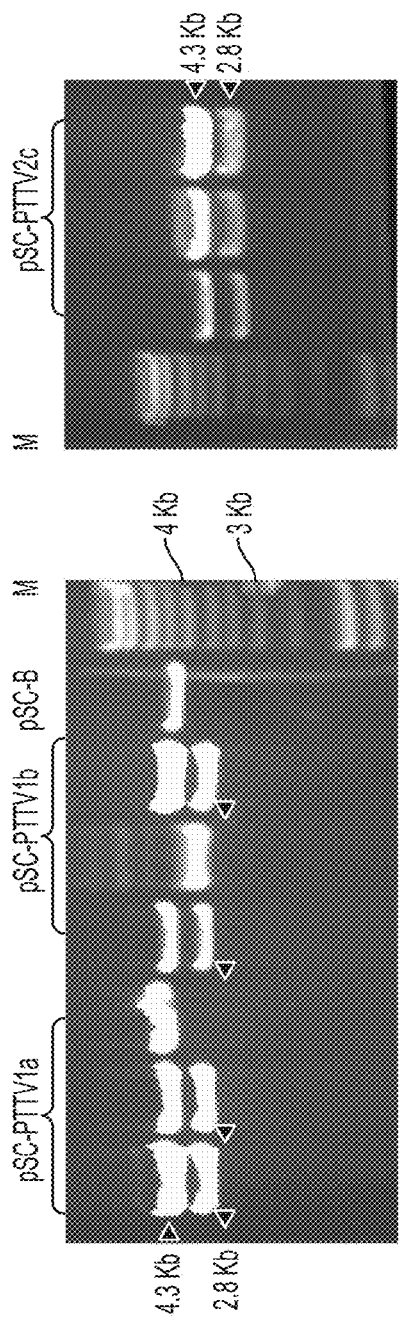
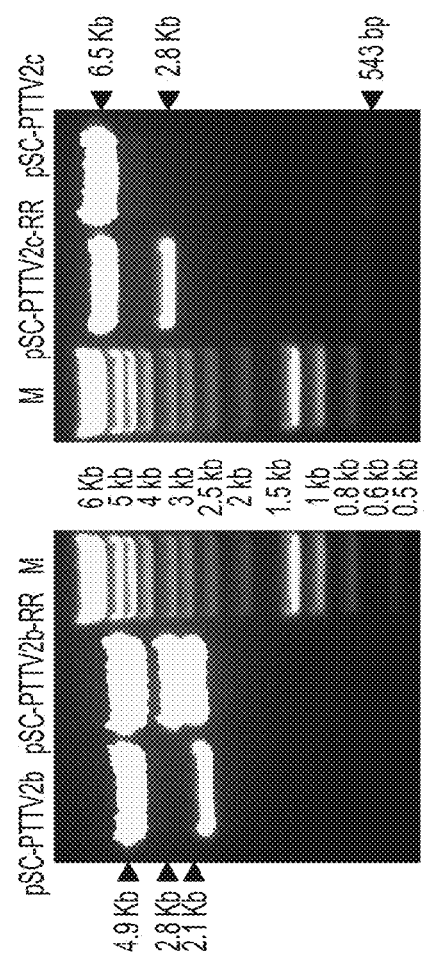
FIG. 18A
FIG. 18B

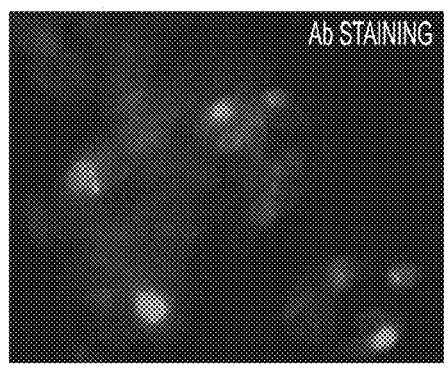
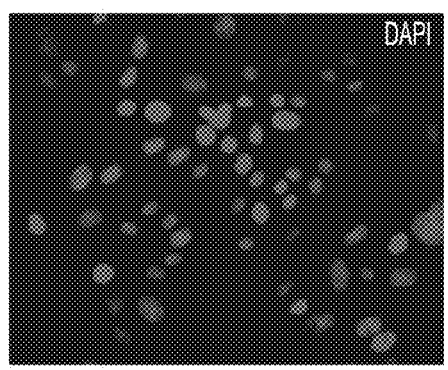
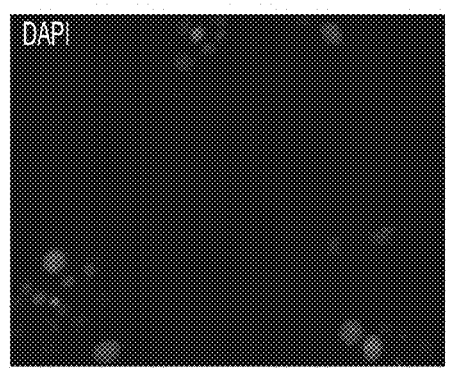
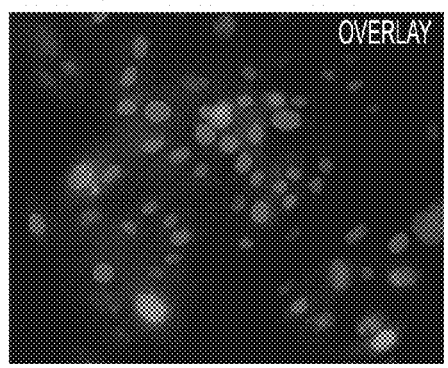
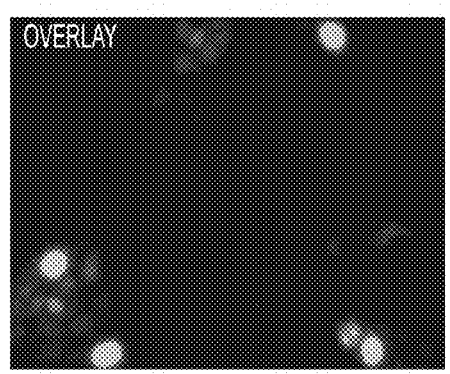
FIG. 20A                    FIG. 20B

PORCINE TORQUE TENO VIRUS VACCINES AND DIAGNOSIS

CROSS REFERENCE TO RELATED APPLICATION

This patent application is a continuation of U.S. application Ser. No. 12/861,378, filed Aug. 23, 2010, and issued as U.S. Pat. No. 9,228,242 on Jan. 5, 2016, which claims the benefit of U.S. Provisional Patent Application No. 61/235,833, filed on Aug. 21, 2009, and U.S. Provisional Patent Application 61/316,519, filed on Mar. 23, 2010, whose disclosures are herein incorporated by reference in their entirety into the present disclosure.

FIELD OF INVENTION

The present invention relates to vaccines for protecting against porcine Torque teno virus (TTV) infection, and infectious DNA clones of porcine TTV (PTTV) and their uses thereof. The present invention also relates to diagnosis of porcine Torque teno virus (PTTV) infection, particularly diagnosis of species- or type-specific PTTV infection, and simultaneous infection of multiple strains from different genotypes.

BACKGROUND OF THE INVENTION

Torque teno virus (TTV) was first discovered in a Japanese patient with post-transfusion non-A-E hepatitis in 1997. (Nishizawa, T., et al. A novel DNA virus (TTV) associated with elevated transaminase levels in posttransfusion hepatitis of unknown etiology. *Biochem Biophys Res Commun* 241(1) (1997) 92-7). Since then, a large number of human TTV strains and two groups of TTV-related viruses, designated subsequently as Torque teno mini virus (TTMV) and Torque teno midi virus (TTMDV), have been identified with high prevalence in serum and other tissues from healthy humans. (Hino, S., and Miyata, H. Torque teno virus (TTV): current status. *Rev Med Virol* 17(1) (2007) 45-57; Okamoto, H. History of discoveries and pathogenicity of TT viruses. *Curr Top Microbiol Immunol* 331 (2009a) 1-20). Human TTV, TTMV and TTMDV are non-enveloped spherical viruses with circular single-stranded DNA (ssDNA) genomes of 3.6-3.9, 2.8-2.9 and 3.2 kb in length, respectively, and they are currently classified into a newly-established family Anelloviridae by the International Committee on Taxonomy of Viruses (ICTV) (Biagini, P. Classification of TTV and related viruses (anelloviruses). *Curr Top Microbiol Immunol* 331 (2009) 21-33). These three groups of TTV-related viruses exhibit a high degree of genetic heterogeneity, each consisting of many genogroups and genotypes. (Biagini, P., et al. Distribution and genetic analysis of TTV and TTMV major phylogenetic groups in French blood donors. *J Med Virol* 78(2) (2006) 298-304; Jelcic, I., et al. Isolation of multiple TT virus genotypes from spleen biopsy tissue from a Hodgkin's disease patient: genome reorganization and diversity in the hypervariable region. *J Virol* 78(14) (2004) 7498-507). The prevalence of multiple infections of TTV with different genotypes as well as dual or triple infections of TTV, TTMV and TTMDV have been documented in humans, and are considered to be a common event in healthy human adults. (Niel, C., et al. Coinfection with multiple TT virus strains belonging to different genotypes is a common event in healthy Brazilian adults. *J Clin Microbiol* 38 (5) (2000) 1926-30; Ninomiya, M., et al. Analysis of the entire genomes of torque teno midi virus variants in chimpanzees: infrequent cross-species infection between humans and chimpanzees. *J Gen Virol* 90(Pt 2) (2009) 347-58; Okamoto, H. History of discoveries and pathogenicity of TT viruses. *Curr Top Microbiol Immunol* 331 (2009a) 1-20; Takayama, S., et al. Prevalence and persistence of a novel DNA TT virus (TTV) infection in Japanese haemophiliacs. *Br J Haematol* 104 (3) (1999) 626-9).

TTV infects not only humans but also various other animal species as well including non-human primates, tupaias, pigs, cattle, cats, dogs and sea lions (Biagini, P., et al. (2007). Circular genomes related to anelloviruses identified in human and animal samples by using a combined rolling-circle amplification/sequence-independent single primer amplification approach. *J Gen Virol* 88 (Pt 10), 2696-701; Inami, T., et al. (2000). Full-length nucleotide sequence of a simian TT virus isolate obtained from a chimpanzee: evidence for a new TT virus-like species. *Virology* 277(2), 330-5; Ng, T. F., et al. (2009). Novel anellovirus discovered from a mortality event of captive California sea lions. *J Gen Virol* 90(Pt 5), 1256-61; Okamoto, H. (2009b). TT viruses in animals. *Curr Top Microbiol Immunol* 331, 35-52; Okamoto, H., et al. (2001). Genomic and evolutionary characterization of TT virus (TTV) in tupaias and comparison with species-specific TTVs in humans and non-human primates. *J Gen Virol* 82(Pt 9), 2041-50; Okamoto, H., et al. (2000a). Species-specific TT viruses in humans and nonhuman primates and their phylogenetic relatedness. *Virology* 277(2), 368-78; Okamoto, H., et al. (2002). Genomic characterization of TT viruses (TTVs) in pigs, cats and dogs and their relatedness with species-specific TTVs in primates and tupaias. *J Gen Virol* 83(Pt 6), 1291-7). In addition, chimpanzees are also infected with TTMV and TTMDV (Ninomiya, M., et al. (2009). Analysis of the entire genomes of torque teno midi virus variants in chimpanzees: infrequent cross-species infection between humans and chimpanzees. *J Gen Virol* 90(Pt 2), 347-58; Okamoto et al., 2000a, supra). Although the genomic sizes of the identified animal TTV strains, especially non-primate animal TTV, are relatively smaller than that of human TTV, they share the same genomic structure with a minimum of two partially overlapping open reading frames (ORF1 and ORF2) translated from the negative ssDNA as well as a short stretch of untranslated region (UTR) with high GC content (~90%) (Okamoto, 2009b, supra). The arrangement of TTV ORFS is quite similar to that of chicken anemia virus (CAV) belonging to the genus Gyrovirus in the family Circoviridae but is different from porcine circovirus (PCV) types 1 (PCV1) and 2 (PCV2), which are also classified into the same family (Davidson, I., and Shulman, L. M. (2008). Unraveling the puzzle of human anellovirus infections by comparison with avian infections with the chicken anemia virus. *Virus Res* 137(1), 1-15; Hino, S., and Prasetyo, A. A. (2009). Relationship of Torque teno virus to chicken anemia virus. *Curr Top Microbiol Immunol* 331, 117-30). The genomes of PCV1 and PCV2 are ambisense, in which the ORF1 is coded for by the genomic strand and the ORF2 is coded for by the antigenomic strand (Hino and Miyata, 2007, supra). Recently, the transcription pattern and translated products of both human TTV genotypes 1 and 6 have been identified by transfection of the respective TTV infectious DNA clones into cultured cells (Mueller, B., et al. (2008). Gene expression of the human Torque Teno Virus isolate P/1C1. *Virology* 381(1), 36-45; Qiu, J., et al. (2005). Human circovirus TT virus genotype 6 expresses six proteins following transfection of a full-length clone. *J Virol* 79(10), 6505-10). Expression of at least six proteins, designated ORF1, ORF2, ORF1/1, ORF2/2, ORF1/2 and ORF2/3, from three or more spliced mRNAs, have been reported (Kakkola, L., et al. (2009). Replication of and protein synthesis by TT viruses. *Curr Top Microbiol Immunol* 331, 53-64; Mueller et al., 2008, supra; Qiu et al., 2005, supra). Accordingly, it is likely that, when more data regarding the animal TTV become available, the presumed genome structure of animal TTV will need to be modified.

Although TTV was first identified in a cryptogenic hepatitis patient, subsequent studies were not able to produce evidence of a significant role of TTV in the pathogenesis of hepatitis or other diseases (Hino and Miyata, 2007, supra; Maggi, F., and Bendinelli, M. (2009). Immunobiology of the Torque teno viruses and other anelloviruses. *Curr Top Microbiol Immunol* 331, 65-90; Okamoto, 2009a, supra). While human TTV is not considered to be directly associated with a disease, porcine TTV (PTTV) was recently shown to partially contribute to the experimental induction of porcine dermatitis and nephropathy syndrome (PDNS) combined with porcine reproductive and respiratory syndrome virus (PRRSV) infection (Krakowka, S., et al. (2008). Evaluation of induction of porcine dermatitis and nephropathy syndrome in gnotobiotic pigs with negative results for porcine circovirus type 2. *Am J Vet Res* 69(12), 1615-22), and also to the experimental induction of postweaning multisystemic wasting syndrome (PMWS) combined with PCV2 infection in a gnotobiotic pig model (Ellis, J. A., et al. (2008). Effect of coinfection with genogroup 1 porcine torque teno virus on porcine circovirus type 2-associated postweaning multisystemic wasting syndrome in gnotobiotic pigs. *Am J Vet Res* 69(12), 1608-14). The data suggested that porcine TTV is pathogenic in pigs. However, further in-depth studies with a biologically pure form of PTTV virus to definitively characterize the diseases and lesions associated with PTTV infection are needed.

Compared to human TTV, the genomic information of PTTV is very limited. Currently, only one full-length and two near full-length genomic sequences of PTTV are reported from pigs in Japan and Brazil, respectively (Niel, C., et al. (2005). Rolling-circle amplification of Torque teno virus (TTV) complete genomes from human and swine sera and identification of a novel swine TTV genogroup. *J Gen Virol* 86 (Pt 5), 1343-7; Okamoto et al., 2002, supra). Among the three known PTTV strains, the Sd-TTV31 and TTV-1p stains were clustered together into the genogroup 1 (PTTV1), whereas TTV-2p was the sole strain classified into the genogroup 2 (PTTV2) (Niel et al., 2005, supra). However, genogroup classification is a vague concept in the taxonomy of virology, and further and more accurate classification of PTTV is needed but can only be performed when more full-length genomic sequences of new PTTV strains representing multiple genotypes become available.

It was previously showed that PTTV infections were widespread in pigs from six different countries including the United States, Canada, Spain, China, Korea and Thailand (McKeown, N. E., Fenaux, M., Halbur, P. G., and Meng, X. J. (2004). Molecular characterization of porcine TT virus, an orphan virus, in pigs from six different countries. *Vet Microbiol* 104(1-2), 113-7).

Whether porcine TTVs play a significant role in pathogenesis of specific swine diseases is still debatable. In a gnotobiotic pig model, it was shown that PTTV1 infection alone did not develop any clinical diseases but induced mild histological lesions (Krakowka, S. and Ellis, J. A., 2008. Evaluation of the effects of porcine genogroup 1 torque teno virus in gnotobiotic swine. *Am J Vet Res* 69, 1623-9). Gnotobiotic pigs that were experimentally inoculated with both PTTV1 and porcine reproductive and respiratory syndrome virus (PRRSV) developed clinical porcine dermatitis and nephropathy syndrome (PDNS) (Krakowka, S., et al. 2008. Evaluation of induction of porcine dermatitis and nephropathy syndrome in gnotobiotic pigs with negative results for porcine circovirus type 2. *Am J Vet Res* 69, 1615-22), whereas pigs inoculated with both PTTV1 and porcine circovirus type 2 (PCV2) developed acute postweaning multisystemic wasting syndrome (PMWS) (Ellis et al., 2008, supra). Although PCV2 is considered as the primary causative agent for clinical PMWS or PCV-associated diseases (PCVAD), a higher prevalence of PTTV2 infection in PMWS-affected pigs with low or no PCV2 than that in non-PMWS-affected pigs was observed in Spain (Kekarainen et al., 2006, supra). The data collectively suggest that porcine TTVs may serve as co-factors involved in triggering or exacerbating diseases in pigs.

Porcine TTV has been detected in porcine serum, fecal, saliva, semen and tissue samples of infected pigs, indicating its diverse transmission routes including both horizontal and vertical transmissions (Kekarainen et al., 2007, supra; Pozzuto, T., et al. 2009. In utero transmission of porcine torque teno viruses. *Vet Microbiol* 137, 375-9; Sibila, M., et al. 2009. Swine torque teno virus (TTV) infection and excretion dynamics in conventional pig farms. *Vet Microbiol* 139, 213-8). However, current detection of porcine TTV infection was mainly based upon conventional PCR assays. Thus far, neither serological assay nor viral culture system has been established. In particular, nested PCR amplifications of the conserved regions in the UTR of PTTV1 and PTTV2, respectively, developed by a Spanish group, have become widely used (Kekarainen et al., 2006, supra). Since the amount of virus is likely associated with the severity of clinical diseases, as demonstrated for PCV2-induced PCVAD (Opriessnig, T., Meng, X. J. and Halbur, P. G., 2007. Porcine circovirus type 2 associated disease: update on current terminology, clinical manifestations, pathogenesis, diagnosis, and intervention strategies. *J Vet Diagn Invest* 19, 591-615), it will be important to determine the viral load of porcine TTV by quantitative real-time PCR than the presence of TTV DNA by conventional PCR. In addition, real-time PCR is more reliable, rapid and less expensive than conventional PCR. Recently, two TaqMan probe-based real-time PCR assays were described for detection and quantification of two porcine TTV species (Brassard, J., et al. 2009. Development of a real-time TaqMan PCR assay for the detection of porcine and bovine Torque teno virus. *J Appl Microbiol.* Nov. 14, 2009, Epub ahead of print; Gallei, A., et al. 2009. Porcine Torque teno virus: Determination of viral genomic loads by genogroup-specific multiplex rt-PCR, detection of frequent multiple infections with genogroups 1 or 2, and establishment of viral full-length sequences. *Vet Microbiol.* Dec. 21, 2009, Epub ahead of print). A main drawback of probe-based assays is that the false-negative results may be obtained if the probe-binding sequences contain mutations (Anderson, T. P., et al. 2003. Failure to genotype herpes simplex virus by real-time PCR assay and melting curve analysis due to sequence variation within probe binding sites. *J Clin Microbiol* 41, 2135-7). Considering the high degree of heterogeneity among the sequences of known porcine TTV strains, variations in the probe-binding sequences are expected for field strains of PTTVs. The SYBR green-based real-time PCR is an alternative method avoiding this potential problem, in spite of its relatively lower specificity, which provides a universal way to detect and quantify the potential porcine TTV variants. Moreover, melting curve analysis (MCA) following SYBR green real-time PCR ensures reaction specificity and also allows multiplex detection of distinct types of virus (Ririe, K. M., et al. 1997. Product differentiation by analysis of DNA melting curves during the polymerase chain reaction. Anal Biochem 245, 154-60). MCA-based SYBR green real-time PCR methods have been successfully applied to various human and veterinary viruses (Gibellini, D., et al. 2006. Simultaneous detection of HCV and HIV-1 by SYBR Green real time multiplex RT-PCR technique in plasma samples. *Mol Cell Probes* 20, 223-9; Martinez, E., et al. 2008. Simultaneous detection and genotyping of porcine reproductive and respiratory syndrome virus (PRRSV) by real-time RT-PCR and amplicon melting curve analysis using SYBR Green. *Res Vet Sci* 85, 184-93; Mouillesseaux, K. P., et al. 2003. Improvement in the specificity and sensitivity of detection for the Taura syndrome virus and yellow head virus of penaeid shrimp by increasing the amplicon size in SYBR Green real-time RT-PCR. *J Virol Methods* 111, 121-7; Wilhelm, S., et al. 2006. Real-time PCR protocol for the detection of porcine parvovirus in field samples. *J Virol Methods* 134, 257-60).

Currently, little is known about PTTV-specific humoral response. Since PCR-based assays do not reflect the course of PTTV infection in pigs, an efficient enzyme-linked immunosorbent assay (ELISA) for detection of PTTV serum antibody is necessary to evaluate seroprevalence of PTTV and help characterize the role of PTTV in porcine diseases.

Thus far, no subunit, killed and live vaccines for porcine TTVs are available. It will be desirable and advantageous to express recombinant PTTV capsid proteins from different genotypes for development of PTTV subunit vaccines, and to construct infectious PTTV molecular DNA clones from different genotypes for propagating biological pure form of PTTVs in cell culture system that are used for killed and live vaccines development.

SUMMARY OF THE INVENTION

The present invention provides an infectious nucleic acid molecule ("infectious DNA clone") of porcine Torque teno virus (PTTV) comprising a nucleic acid molecule encoding an infectious PTTV which contains at least one copy of genomic sequence having at least 80% homology to a genomic sequence selected from the group consisting of genotypes of PTTV1a-VA, PTTV1b-VA, PTTV2b-VA, and PTTV2c-VA.

According to one aspect of the present invention, the infectious DNA clones of PTTV of set forth in claim 1, wherein the genomic sequence is selected from sequences set forth in SEQ ID NO:9, SEQ ID NO:10, SEQ ID NO:11, and SEQ ID NO:12.

The present invention provides a biologically functional plasmid or viral vector containing the infectious PTTV genomes.

The present invention provides a suitable host cell transfected with the infectious clone DNA plasmid or viral vector.

The present invention provides an infectious PTTV produced by cells transfected with the PTTV infectious DNA clones.

The present invention also provides a viral vaccine comprising a nontoxic, physiologically acceptable carrier and an immunogenic amount of a member selected from the group consisting of (a) a nucleic acid molecule containing at least one copy of genomic sequence having at least 80% homology to a genomic sequence selected from the group consisting of PTTV genotypes or subtypes PTTV1a-VA, PTTV1b-VA, PTTV2b-VA, and PTTV2c-VA, or its complementary strand, (b) a biologically functional plasmid or viral vector containing a nucleic acid molecule containing at least one copy of genomic sequence having at least 80% homology to a genomic sequence selected from the group consisting of PTTV genotypes or subtypes PTTV1a-VA, PTTV1b-VA, PTTV2b-VA, and PTTV2c-VA, or its complementary strand, and (c) an avirulent, infectious nonpathogenic PTTV which contains at least one copy of genomic sequence having at least 80% homology to a genomic sequence selected from the group consisting of PTTV genotypes or subtypes PTTV1a-VA, PTTV1b-VA, PTTV2b-VA, and PTTV2c-VA.

According to one aspect of the present invention, the vaccine contains live PTTV virus derived from the PTTV infectious clones. According to another aspect of the present invention, the vaccine contains killed PTTV virus derived from the PTTV infectious clones.

The present invention provides purified recombinant proteins expressed from the ORF1 capsid genes of PTTV genotypes or subtypes PTTV1a-VA, PTTV1b-VA, and PTTV2c-VA in bacterial expression system, and the use of these recombinant capsid proteins as subunit vaccines against PTTV infections. In one embodiment of the present invention, the recombinant capsid proteins for the use as subunit vaccines are expressed in baculovirus expression system and other expression vector systems.

According to a further aspect of the present invention, further contains an adjuvant.

The present invention further provides a method of immunizing a pig against PTTV viral infection, comprising administering to a pig an immunologically effective amount of the viral vaccine.

According to one aspect of the present invention, the method comprising administering the recombinant subunit capsid protein, the infectious nucleic acid molecule or live PTTV virus to the pig.

According to another aspect of the present invention, the method comprising administering the vaccine parenterally, intranasally, intradermally, or transdermally to the pig. According a further aspect of the present invention, the method comprising administering the vaccine intralymphoidly or intramuscularly to the pig.

The present invention also provides an isolated polynucleotide consisting of the sequence of the nucleotide sequence of PTTV1a-VA set forth in SEQ ID NO:9.

The present invention also provides an isolated polynucleotide consisting of the sequence of the nucleotide sequence of PTTV1b-VA set forth in SEQ ID No:10.

The present invention also provides an isolated polynucleotide consisting of the sequence of the nucleotide sequence of PTTV2b-VA set forth in SEQ ID No:11.

The present invention also provides an isolated polynucleotide consisting of the sequence of the nucleotide sequence of PTTV2c-VA set forth in SEQ ID No:12.

The present invention further provides a subunit vaccine comprising an immunogenic fragment of a polypeptide sequence or a complete protein translated according to a polynucleotide sequence selected from the group consisting of ORF1, ORF2, ORF1/1, and ORF2/2 of PTTV genotypes or subtypes PTTV1a-VA, PTTV1b-VA, PTTV2b-VA, and PTTV2c-VA, particularly the ORF1 encoding the capsid protein.

According to one aspect of the present invention, the polynucleotide sequence is selected from the group consisting of ORF1 of PTTV genotypes or subtypes PTTV1a-VA, PTTV1b-VA, PTTV2b-VA, and PTTV2c-VA.

According to another aspect of the present invention, the polynucleotide sequence is ORF1 of PTTV genotype PTTV1a-VA. According to a further aspect of the present invention, the polynucleotide sequence is ORF1 of PTTV genotype PTTV1b-VA. According to yet another aspect of the present invention, the polynucleotide sequence is ORF1 of PTTV subtype PTTV2c-VA.

According to one aspect of the present invention, the polypeptide sequence is selected from the group consisting of sequence set forth in SEQ ID No:13, SEQ ID No:14, SEQ ID No:15, SEQ ID No:16, SEQ ID No:17, SEQ ID No:18, SEQ ID No:19, SEQ ID No:20, SEQ ID No:21, SEQ ID No:22, SEQ ID No:23, SEQ ID No:24, SEQ ID No:25, SEQ ID No:26, SEQ ID No:27, and SEQ ID No:28.

According to another aspect of the present invention, the polypeptide sequence is set forth in SEQ ID No:13. According to another aspect of the present invention, the polypeptide sequence is set forth in SEQ ID No:14. According to a further aspect of the present invention, the polypeptide sequence is set forth in SEQ ID No:16. In one specific embodiment of the present invention, the polypeptide sequence is C-terminal region (aa 310-625) of SEQ ID No:16. According to yet another aspect of the present invention, the polypeptide sequence is set forth in SEQ ID No:20.

According to an additional aspect of the present invention, the vaccine further contains an adjuvant.

The present invention further provides method of immunizing a pig against PTTV viral infection, comprising administering to a pig an immunologically effective amount of the vaccine comprising an immunogenic fragment of a polypeptide sequence or a complete protein translated according to a polynucleotide sequence selected from the group consisting of ORF1, ORF2, ORF1/1, and ORF2/2 of PTTV genotypes or subtypes PTTV1a-VA, PTTV1b-VA, PTTV2b-VA, and PTTV2c-VA.

According to one aspect of the present invention, the method comprises administering the immunogenic fragment or recombinant capsid protein to the pig.

According to another aspect of the present invention, the method comprises administering the vaccine parenterally, intranasally, intradermally, or transdermally to the pig. According to a further aspect of the present invention, the method comprises administering the vaccine intralymphoidly or intramuscularly to the pig.

The present invention additionally provides a method for diagnosing PTTV1 infection and quantification of PTTV1 load, comprising extracting DNA from a sample suspected of PTTV1 infection, performing polymerase chain reaction (PCR) using primers comprising the sequences set forth in SEQ ID NO:29 and SEQ ID NO:30, and detecting PTTV1 specific amplification. According to one aspect of the present invention, the polymerase chain reaction is a SYBR green real-time PCR.

The present invention further provides a method for diagnosing PTTV2 infection and quantification of PTTV2 load, comprising extracting DNA from a sample suspected of PTTV2 infection, performing polymerase chain reaction (PCR) using primers comprising the sequences set forth in SEQ ID NO:29, SEQ ID NO:30, SEQ ID NO:31 and SEQ ID NO:32, and detecting PTTV2 specific amplification. According to one aspect of the present invention, the polymerase chain reaction is a SYBR green real-time PCR.

The present invention also provides a method for simultaneously detecting and diagnosing PTTV1 and PTTV2 infection, comprising extracting DNA from a sample suspected of PTTV infection, performing polymerase chain reaction (PCR) using primers comprising the sequences set forth in SEQ ID NO:31 and SEQ ID NO:32, and detecting PTTV1 and PTTV2 specific amplification. According to one aspect of the present invention, the polymerase chain reaction is a SYBR green real-time PCR.

The present invention, in addition, provides a method for simultaneously detecting and diagnosing PTTV1a and PTTV1b infection, comprising extracting DNA from a sample suspected of PTTV1 infection, performing a first polymerase chain reaction (PCR) using primers comprising the sequences set forth in SEQ ID NO:33 and SEQ ID NO:34, performing a second PCR using primers comprising the sequences set forth in SEQ ID NO:35, SEQ ID NO:36, SEQ ID NO:37, and SEQ ID NO:38, and detecting PTTV1a and PTTV1b specific amplification.

The present invention provides a method for diagnosing PTTV infection, comprising immobilizing an immunogenic fragment of a polypeptide sequence translated according to a polynucleotide sequence selected from the group consisting of ORF1, ORF2, ORF1/1, and ORF2/2 of PTTV genotypes or subtypes PTTV1a-VA, PTTV1b-VA, PTTV2b-VA, and PTTV2c-VA; contacting a serum sample from a pig suspected of PTTV infection with the immobilized immunogenic fragment, and detecting captured antibody specific to the immunogenic fragment.

According to one aspect of the present invention, the polynucleotide sequence is selected from the group consisting of ORF1 of PTTV genotypes or subtypes PTTV1a-VA, PTTV1b-VA, PTTV2b-VA, and PTTV2c-VA.

According to one embodiment of the present invention, the polynucleotide sequence is ORF1 of PTTV genotype PTTV1a-VA. According to another embodiment of the present invention, the polynucleotide sequence is ORF1 of PTTV genotype PTTV1b-VA. According to a further embodiment of the present invention, the polynucleotide sequence is ORF1 of PTTV subtype PTTV2c-VA.

According to another aspect of the present invention, the polypeptide sequence is selected from the group consisting of sequence set forth in SEQ ID No:13, SEQ ID No:14, SEQ ID No:15, SEQ ID No:16, SEQ ID No:17, SEQ ID No:18, SEQ ID No:19, SEQ ID No:20, SEQ ID No:21, SEQ ID No:22, SEQ ID No:23, SEQ ID No:24, SEQ ID No:25, SEQ ID No:26, SEQ ID No:27, and SEQ ID No:28.

According to one embodiment of the present invention, the polypeptide sequence is set forth in SEQ ID No: 13. According to another aspect of the present invention, the polypeptide sequence is set forth in SEQ ID No: 14. According to another embodiment of the present invention. The polypeptide sequence is set forth in SEQ ID No: 16. According to a further embodiment of the present invention, the immunogenic fragment is C-terminal region (aa 310-625) of SEQ ID No: 16. According to yet another embodiment of the present invention, the polypeptide sequence is set forth in SEQ ID No: 20.

The present invention provides three standardized enzyme-linked immunosorbent assays (ELISA) to diagnose PTTV infections and detect antibodies in serum of pigs infected by PTTV genotypes PTTV1a-VA, PTTV1b-VA, and all known subtypes in PTTV species 2.

The ELISA diagnostic tests are based on the bacterial-expressed or baculovirus-expressed recombinant ORF1 capsid protein of PTTV genotypes PTTV1a-VA, PTTV1b-VA, and PTTV2c-VA.

According to another aspect of the present invention, the detecting captured antibody is via Western blot. According to yet another aspect of the present invention, the detecting captured antibody is via enzyme-linked immunosorbent assay (ELISA).

BRIEF DESCRIPTION OF THE DRAWINGS

The above-mentioned features of the invention will become more clearly understood from the following detailed description of the invention read together with the drawings in which:

FIG. 1C illustrates differentiation and assembly of full-length genomic sequences of PTTV1 strains PTTV1a-VA and PTTV1b-VA with PCR fragments Band C that were subsequently cloned. (PTTV1a-VA=SEQ ID NO: 9, Sd-TTV31=SEQ ID NO: 53, PTTV1bVA=SEQ ID NO: 10, TTV-1p=SEQ ID NO: 56);

FIG. 1D genomic sequences of PTTV2 strains PTTV2b-VA and PTTV2c-VA with PCR fragments E and F that were subsequently cloned. (TTV-2p=SEQ ID NO: 59, PTTV2b-VA=SEQ ID NO: 11, and PTTV2c-VA=SEQ ID NO: 12);

FIGS. 9A and 9B represent hydrophilicity profiles and conserved regions of the four known porcine TTV2 (TTV-2p=SEQ ID NO: 60, TTV2#472142=SEQ ID NO: 62, PTTV2b-VA=SEQ ID NO: 15, and PPT2c-VA=SEQ ID NO: 16);

FIG. 17A: pSC-PTTV1a (from the US PTTV isolate PTTV1a-VA; GenBank accession no. GU456383). FIG. 17B: pSC-PTTV1b (from the US PTTV isolate PTTV1b-VA; GenBank accession no. GU456384). FIG. 17C: pSC-PTTV2c (from the US PTTV isolate PTTV2c-VA; GenBank accession no. GU456386). FIG. 17D: pSC-2PTTV2c-RR (tandem-dimerized genomes). FIG. 17E: TTV2-#471942-full (from the Germany PTTV isolate TTV2-#471942; a gift from Dr. Andreas Gallei, not generated by the applicants). FIG. 17F: pSC-2PTTV2b-RR (tandem-dimerized genomes; generated by the applicants based on the clone TTV2-#471942-full). The plasmid backbone used for the cloning of (A)-(D), and (F) was the pSC-B-amp/kan vector (indicated in black). Grey arrows indicated the PTTV genomic copies;

FIGS. 18A and 18B represent the identification of porcine TTV full-length DNA clones by restriction digestion patterns. FIG. 18A: BamH I single digestion of pSC-PTTV1a, pSC-PTTV1b and pSC-PTTV2c clones and the backbone vector pSC-B-amp/kan (pSC-B). The 4.3-Kb fragments indicated the size of the backbone vector whereas the 2.8-Kb fragments indicated the inserted PTTV genomes (black arrowheads). FIG. 18B: Comparisons of the Hind III single digestion between pSC-PTTV2b and pSC-2PTTV2b-RR (left; derived from the clone TTV2-#471942-full) and Afl II single digestion between pSC-PTTV2c and pSC-2PTTV2c-RR (right). M: DNA markers;

FIG. 19A: Results observed at 5 days post-transfection. FIG. 19B: Cells transfected with DNA clones were passaged and used for the IFA detection at 2 days post-passaging. Magnification=200×. DAPI was used to stain the cell nucleus;

FIGS. 20A and 20B represent the IFA results of transfection (20A) or transfected cell passaging (20B) of the concatemerized PTTV2c DNA in PK-15 cells using a PTTV2-specific anti-ORF1 Ab. FIG. 20A: Results observed at 5 days post-transfection. FIG. 20B: Cells transfected with the DNA clones were passaged and used for the IFA detection at 2 days post-passaging. Magnification=200×. DAPI was used to stain the cell nucleus;

FIG. 23A: Changes of viremia or virus titers (copies/ml) as determined by PTTV2-specific real-time PCR. FIG. 23B: Seroconversion to IgG anti-porcine TTV2 ORF1 antibodies in pigs. Anti-PTTV2 antibody is plotted as the ELISA optical density (A405). The ELISA cutoff value, indicated by a dashed line in each panel, is 0.4.

DETAILED DESCRIPTION OF THE INVENTION

In accordance with the present invention, in one specific example, the aforementioned four novel porcine TTV subtypes are isolated from a single boar in Virginia.

Figures 1A, 1B:
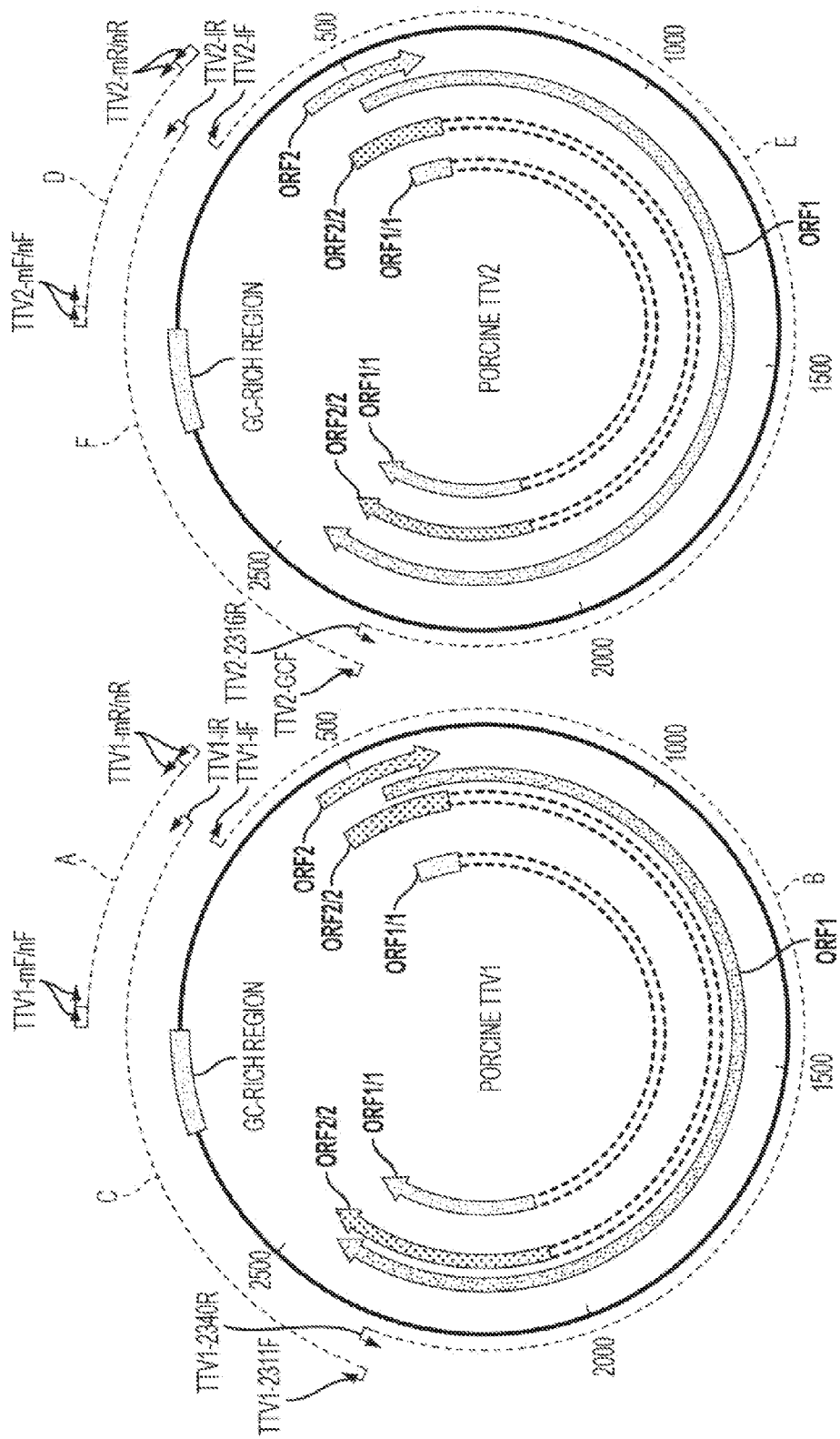
FIG. 1A represents a schematic diagram of genomic structures and strategies for genomic cloning of porcine TTV virus group 1 strains.
FIG. 1B represents a schematic diagram of genomic structures and strategies for genomic cloning of porcine TTV virus group 2 strains.

In FIGS. 1A and 1B respectively, both the PTTV1 and PTTV2 genomes are shown in bold and the sizes and directions of the four putative ORFs (ORF1, ORF2, ORF1/1 and ORF2/2) are indicated by arrows. The GC-rich regions are also shown. Dashed-line arcs A and D represent the regions used for detection of PTTV1 and PTTV2 from serum and semen samples by nested PCR, respectively. Dashed-line arcs B and C represent the two overlapping PCR fragments for genomic cloning of PTTV1 whereas dashed-line arcs E and F represent the two overlapping PCR fragments for genomic cloning of PTTV2. The locations of the primers used in the study (see Table 1) are also shown in the corresponding positions.

One boar serum sample (SR#5) that was shown to be positive for both PTTV1 and PTTV2 in the first-round PCR, thus indicative of higher virus load, was used for subsequent full-length genomic cloning of PTTV. Surprisingly, initial attempts to utilize two primer sets (NG372/NG373 and NG384/NG385) of an inverse PCR (Okamoto et al., 2002, supra) designed for cloning of the first PTTV strain Sd-TTV31 to amplify the virus genomic DNA were not successful. No PCR product was obtained after several trials. Based upon the initial sequence of the region A of PTTV1 and the region D of PTTV2, two new pairs of primers (TTV1-If (SEQ ID NO:1)/TTV1-2340R (SEQ ID NO:2) and TTV1-2311F (SEQ ID NO:3)/TTV1-IR (SEQ ID NO:4)) were subsequently designed to amplify regions B and C spanning the assumed PTTV1 genome, and two additional pairs of primers (TTV2-IF (SEQ ID NO:5)/TTV2-2316R (SEQ ID NO:6) and TTV2-GCF (SEQ ID NO:7)/TTV2-IR (SEQ ID NO:8)) to amplify regions E and F spanning the assumed PTTV2 genome, respectively (FIGS. 1A-1D and Table 1). Primers TTV1-2340R (SEQ ID NO:2) and TTV1-2311F (SEQ ID NO:3) were deduced from a common sequence in PTTV1 stains Sd-TTV31 (Okamoto et al., 2002, supra) and TTV-1p (Niel et al., 2005) that is absent in PTTV2 strain TTV-2p (Niel et al., 2005, supra), whereas primers TTV2-2316R (SEQ ID NO:6) and TTV2-GCF (SEQ ID NO:7) were deduced from a sequence of strain TTV-2p that is absent in the two PTTV1 strains. The resulting four different PCR products with expected sizes were each inserted into a blunt-end cloning vector, and the resulting recombinant plasmids were transformed into *Escherichia coli*. Eight to fifteen positive (with white color) bacterial clones for each construct representing fragments B, C, E and F were identified and subsequently sequenced.

TABLE 1

Oligonucleotide primers used for nested PCR and genomic PCR amplifications of porcine TT viruses

| Primer ID | Sequence (5' to 3') | Used for: |
|---|---|---|
| TTV1-mF (SEQ ID NO: 45) | TACACTTCCGGGTTCAGGA GGCT | Detection of porcine TTV1 |
| TTV1-mR (SEQ ID NO: 46) | ACTCAGCCATTCGGAACCT CAC | Detection of porcine TTV1 |
| TTV1-nF (SEQ ID NO: 47) | CAATTTGGCTCGCTTCGCT CGC | Detection of porcine TTV1 |
| TTV1-nR (SEQ ID NO: 48) | TACTTATATTCGCTTTCGT GGGAAC | Detection of porcine TTV1 |
| TTV2-mF (SEQ ID NO: 49) | AGTTACACATAACCACCAA ACC | Detection of porcine TTV2 |
| TTV2-mR (SEQ ID NO: 50) | ATTACCGCCTGCCCGATA GGC | Detection of porcine TTV2 |
| TTV2-nF (SEQ ID NO: 51) | CCAAACCACAGGAAACTG TGC | Detection of porcine TTV2 |
| TTV2-nR (SEQ ID NO: 52) | CTTGACTCCGCTCTCAGG AG | Detection of porcine TTV2 |
| TTV1-IF (SEQ ID NO: 1) | CATAGGGTGTAACCAATC AGATTTAAGGCGTT | Genomic cloning (fragment B) |
| TTV1-2340R (SEQ ID NO: 2) | GGTCATCAGACGATCCAT CTCCCTCAG | Genomic cloning (fragment B) |
| TTV1-2311F (SEQ ID NO: 3) | CTTCTGAGGGAGATGGAT CGTCTGATGA | Genomic cloning (fragment C) |
| TTV1-IR (SEQ ID NO: 4) | TTGAGCTCCCGACCAATC AGAATTGACT | Genomic cloning (fragment C) |
| TTV2-IF (SEQ ID NO: 5) | TTGTGCCGGAGCTCCTGA GAGC | Genomic cloning (fragment E) |
| TTV2-2316R (SEQ ID NO: 6) | AGGTGCTTGAGGAGTCGT CGCTTG | Genomic cloning (fragment E) |

TABLE 1-continued

Oligonucleotide primers used for nested PCR and
genomic PCR amplifications of porcine TT viruses

| Primer ID | Sequence (5' to 3') | Used for: |
|---|---|---|
| TTV2-GCF (SEQ ID NO: 7) | CTCAAGCACGAGCAGTGG ATCCTCTCA | Genomic cloning (fragment F) |
| TTV2-IR (SEQ ID NO: 8) | TACCCAGGCGGTTAGACA CTCAGCTCT | Genomic cloning (fragment F) |

Unexpectedly, two groups of sequence data from each construct were identified, indicating that there exist two types of PTTVs in genogroup 1 and genogroup 2 from the same pig. In order to differentiate and assemble the four PTTV strains, sequence comparisons were performed together with the three known PTTV strains, Sd-TTV31, TTV-1p and TTV-2p (FIGS. 1C and 1D).

FIG. 1C illustrates differentiation and assembly of full-length genomic sequences of PTTV1 strains PTTV1a-VA and PTTV1b-VA with PCR fragments B and C that were subsequently cloned. The initiation codons of ORF1 and ORF2 in the fragment B as well as the termination codons of ORF1 in the fragment C are marked by "^" or "*". The corresponding sequences of two known PTTV1 strains, Sd-TTV31 and TTV-1p, are also shown. Conserved sequences are shaded, and dashes indicate nucleotide deletions.

For PTTV1, the initiation codon ATG and the termination codon TGA of the putative ORF1 were located in fragments B and C, respectively (FIG. 1C). The positions of the codons differed in two PTTV1 groups, the first one identical to Sd-TTV31 and the second one identical to TTV-1p (FIG. 1C). In addition, the ORF2 initiation codons in the two groups were also located at different positions consistent with that of ORF1. Moreover, phylogenetic analyses using four different sequences of the region B (two from the sequencing data and two from strains Sd-TTV31 and TTV-1p) and four different sequences of the region C supported that the first sequence was clustered with Sd-TTV31 and the second was clustered with TTV-1p (data not shown). Therefore, we were able to differentiate and assemble two groups of sequence data from both fragments B and C into two full-length PTTV1 genomes that were designated as strains PTTV1a-VA (SEQ ID NO:9) and PTTV1b-VA (SEQ ID NO:10), respectively (FIG. 1C).

FIG. 1D illustrates differentiation and assembly of full-length genomic sequences of PTTV2 strains PTTV2b-VA and PTTV2c-VA with PCR fragments E and F that were subsequently cloned. The corresponding sequence of TTV-2p strain is included and the conserved sequences are shaded. Dashes indicate nucleotide deletions. The unique nucleotides within the overlapping region (boxed with dashed-line) for each strain (a continuous "AG" nucleotides for PTTV2b-VA (SEQ ID NO:11) and two single "A" and "G" nucleotides for PTTV2c-VA (SEQ ID NO:12)) are shown, respectively.

Differentiation of the two PTTV2 strains was easier. A unique continuous "AG" nucleotides located in the overlapping region of two PCR fragments was shared by two groups of sequence data from fragments E and F, respectively (FIG. 1D). The assembled full-length genomic sequence represented a PTTV2 strain and was designated as PTTV2b-VA (SEQ ID NO:11). Similarly, the complete genomic sequence of a second strain designated as PTTV2c-VA (SEQ ID NO:12) was assembled based upon two unique single "A" and "G" nucleotides shared in the overlapping region by another set of sequence data from fragments E and F, respectively (FIG. 1D). Phylogenetic analyses using four sequences from fragments E and F together with the two corresponding sequences from TTV-2p also supported this assignment (data not shown).

The present invention provides four isolated porcine TTV virus genotypes or subtypes that are associated with viral infections in pigs. This invention includes, but is not limited to, porcine TTV virus genotypes or subtypes PTTV1a-VA, PTTV1b-VA, PTTV2b-VA, and PTTV2c-VA, the virus genotypes or subtypes which have nucleotide sequences set forth in SEQ ID NO:9 (PTTV1a-VA), SEQ ID NO:10 (PTTV1b-VA), SEQ ID NO:11 (PTTV2b-VA), and SEQ ID NO:12 (PTTV2c-VA), their functional equivalent or complementary strand. It will be understood that the specific nucleotide sequence derived from any porcine TTV will have slight variations that exist naturally between individual viruses. These variations in sequences may be seen in deletions, substitutions, insertions and the like.

The proposed genomic structure for each of the four PTTV strains was analyzed in detail and summarized in Table 2, together with the three known PTTV strains, Sd-TTV31, TTV-1p and TTV-2p. All the four U.S. strains of PTTV have a similar genomic size of 2,878 bp (PTTV1a-VA SEQ ID NO:9), 2,875 bp (PTTV1b-VA SEQ ID NO:10), 2,750 bp (PTTV2b-VA SEQ ID NO:11), and 2,803 bp (PTTV2c-VA SEQ ID NO:12), respectively. Both PTTV1a-VA (SEQ ID NO:9) and Sd-TTV31 have the same genomic length. The published sequences of the strains TTV-1p and TTV-2p all have many undetermined nucleotides in the GC-rich region of the UTR. After artificial filling of these nucleotides with the consensus sequences corresponding to PTTV1 and PTTV2, it was shown that the TTV-1p is more closely-related to PTTV1b-VA (SEQ ID NO:10), and that TTV-2p is more closely-related to PTTV2b-VA (SEQ ID NO:11) in genomic length, respectively (data not shown).

The assembled genomic sequences of porcine TTV virus genotypes or subtypes PTTV1a-VA (SEQ ID NO:9). PTTV1b-VA (SEQ ID NO:10), PTTV2b-VA (SEQ ID NO:11), and PTTV2c-VA (SEQ ID NO:12) are submitted to Genbank® (*Nucleic Acids Research*, 2008 January; 36(Database issue):D25-30) with accession numbers GU456383, GU456384, GU456385, and GU456386, respectively.

TABLE 2

Comparison of the genomic organization and ORFs of the seven porcine TTV strains

| | Porcine TTV species 1 | | | | Porcine TTV species 2 | | |
|---|---|---|---|---|---|---|---|
| | Type 1a | | Type 1b | | Subtype 2a | Subtype 2b | Subtype 2c |
| Virus | | | | | | | |
| Strain | PTTV1a-VA | Sd-TTV31 | PTTV1b-VA | TTV-1p | TTV-2p | PTTV2b-VA | PTTV2c-VA |
| Country | USA | Japan | USA | Brazil | Brazil | USA | USA |
| Full-length (nt) | 2878 | 2878 | 2875 | Uncompleted | Uncompleted | 2750 | 2803 |
| GenBank accession # | GU456383 | AB076001 | GU456384 | AY823990 | AY823991 | GU456385 | GU456386 |
| TATA box | 288-291 | 288-291 | 288-291 | 288-291 | 233-236 | 233-236 | 285-288 |
| Putative mRNA 5'-end | 316 | 316 | 316 | 316 | 261 | 261 | 313 |
| ORF1 | | | | | | | |
| Size (aa) | 635 | 635 | 639 | 637 | 624 | 625 | 625 |
| Exon # | 1 | 1 | 1 | 1 | 1 | 1 | 1 |
| Initiation | 534 | 534 | 517 | 517 | 476 | 476 | 528 |
| Termination | 2441 | 2441 | 2436 | 2430 | 2350 | 2353 | 2405 |
| ORF2 | | | | | | | |
| Size (aa) | 73 | 73 | 72 | 72 | 68 | 68 | 68 |
| Exon # | 1 | 1 | 1 | 1 | 1 | 1 | 1 |
| Initiation | 430 | 430 | 428 | 428 | 393 | 393 | 445 |
| Termination | 651 | 651 | 646 | 646 | 599 | 599 | 651 |
| ORF1/1 | | | | | | | |
| Size (aa) | 174 | 174 | 182 | 182 | 178 | 178 | 178 |
| Exon # | 2 | 2 | 2 | 2 | 2 | 2 | 2 |
| Initiation | 534 | 534 | 517 | 517 | 476 | 476 | 528 |
| Splicing | 647/648 2030/2031 | 647/648 2030/2031 | 642/643 2013/2014 | 642/643 2007/2008 | 595/596 1933/1934 | 595/596 1936/1937 | 647/648 1988/1989 |
| Termination | 2441 | 2441 | 2436 | 2430 | 2350 | 2353 | 2405 |
| ORF2/2 (ORF3) | | | | | | | |
| Size (aa) | 224 | 224 | 228 | 228 | 199 | 199 | 199 |
| Exon # | 2 | 2 | 2 | 2 | 2 | 2 | 2 |
| Initiation | 430 | 430 | 428 | 428 | 393 | 395 | 445 |
| Splicing | 647/648 2030/2031 | 647/648 2030/2031 | 642/643 2013/2014 | 642/643 2007/2008 | 595/596 1933/1934 | 595/596 1936/1937 | 647/648 1988/1989 |
| Termination | 2487 | 2487 | 2485 | 2479 | 2330 | 2333 | 2385 |
| Polyadenylation signal (AATAAA) | 2458-2463 | 2458-2463 | 2462-2467 | 2456-2461 | 2473-2478 | 2476-2481 | 2528-2533 |

The numbers (except sizes of the full-length genome, ORFs and the exon numbers) indicate the nucleotide (nt) positions on the genome of respective PTTV strains.

Two recent studies have identified the transcribed viral mRNAs and the expression of at least six viral proteins during human TTV replication (Mueller et al., 2008, supra; Qiu et al., 2005, supra), which is more than the predicted number of ORFs encoded by human TTV (Okamoto, H., et al. (2000b). TT virus mRNAs detected in the bone marrow cells from an infected individual. *Biochem Biophys Res Commun* 279(2), 700-7), therefore we included the new human TTV genomic information for comparison with the PTTV sequences. The 5'-ends of the mRNA transcripts of human TTV strain P/1C1 were mapped to an "A" that is 25 nt downstream of the TATA-box (Mueller et al., 2008, supra). This starting point, its adjacent sequence (CGAATGGCTGAGTTTATGCCGC (SEQ ID NO:39); the starting point was underlined) and the distance to the upstream TATA-box (24 nt; Table 2) are very conserved in all seven PTTV strains, suggesting that PTTV and human TTV may utilize a common 5'-end of mRNA for translation.

Five additional completely-conserved regions were identified in the vicinity of the TATA-box among all seven PTTV strains. Two regions of 11 nt each (AGTCCTCATTT (SEQ ID NO:40) and AACCAATCAGA (SEQ ID NO:41)) are located in the upstream of the TATA-box, whereas the remaining three regions (CTGGGCGGGTGCCGGAG of 17 nt (SEQ ID NO:42); CGGAGTCAAGGGGC of 14 nt (SEQ ID NO:43); TATCGGGCAGG of 11 nt (SEQ ID NO:44)) are located between the proposed 5'-end of mRNA and the initiation codon of ORF2. These conserved PTTV-specific sequences may contain the common elements regulating the viral gene expression.

Previously, three ORFs (ORFs 1-3) were proposed in the genome of the three known PTTV strains, respectively (Niel et al., 2005, supra; Okamoto et al., 2002, supra). The four prototype U.S. strains of PTTV identified in this study possess this structure. The corresponding ORF3 in human TTV has been renamed as ORF2/2 since it initiates at the same ATG in ORF2 and remains in the same ORF (extending ORF2) after the splicing (FIG. 1A-1B) (Mueller et al., 2008, supra; Qiu et al., 2005, supra). We follow the nomenclature of human TTV for revising PTTV classification in this study. Human TTV ORF1/1 is a newly identified viral protein that is encoded by two exons in ORF1 (Qiu et al., 2005, supra). ORF1/1 share the identical N- and C-terminal part with ORF1. The PTTV ORF1/1 counterpart was readily identified in all seven PTTV strains (FIGS. 1A-1B and Table 2).

The ORF1 and ORF2 are encoded by a ~2.8 kb viral mRNA whereas the ORF1/1 and ORF2/2 are encoded by a spliced viral mRNA with ~1.2 kb in human TTV (Mueller et al., 2008, supra; Qiu et al., 2005, supra). Since these four ORFs were also deduced in PTTV genomes, and since the sequences and positions of the putative splice donor and acceptor sites in the seven PTTV strains are very conserved (Table 2), it is speculated that porcine TTV probably also encodes the two corresponding mRNAs.

Most of the human TTV strains share a genetic similarity with the CAV, encoding a TTV apoptosis-inducing protein (TAIP) in which its CAV counterpart was named apoptin (de Smit, M. H., and Noteborn, M. H. (2009). Apoptosis-inducing proteins in chicken anemia virus and TT virus. Curr Top Microbiol Immunol 331, 131-49). The ORF of TAIP is embedded within the ORF2. However, the corresponding TAIP does not exist in porcine TTV. A recent study showed that the expression of apoptin or TAIP was required for CAV replication in cultured cells (Prasetyo, A. A., et al. (2009). Replication of chicken anemia virus (CAV) requires apoptin and is complemented by VP3 of human torque teno virus (TTV). Virology 385(1), 85-92).

Figure 2:
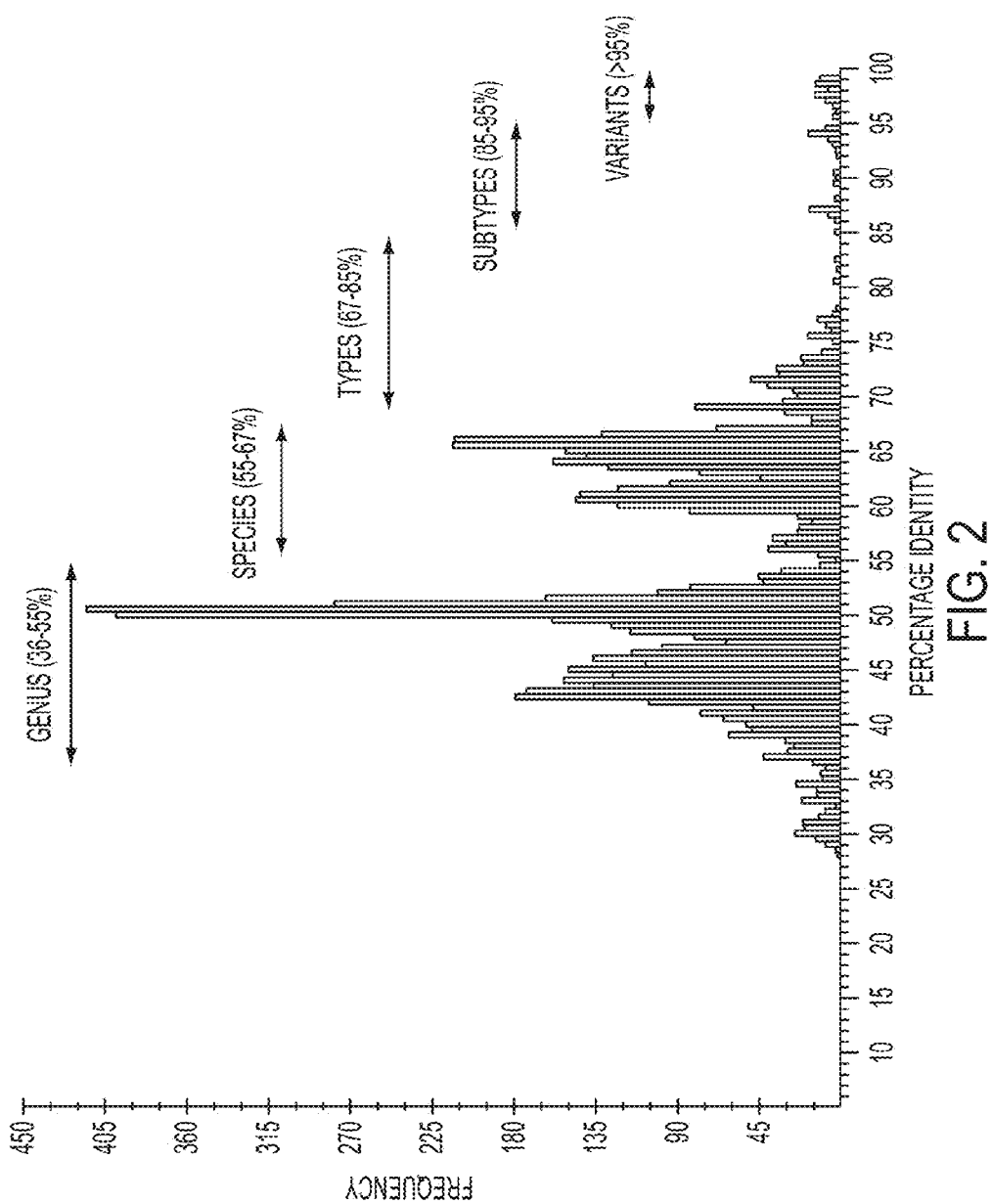
FIG. 2 represents PASC (pairwise sequence comparisons) distribution of nucleotide sequence comparisons of 121 TTV strains available in GenBank database. The genus, species, types, subtypes and variants and their corresponding percentage of nucleotide sequence identities are displayed.

Pairwise sequence comparisons (PASC) is a useful method that plots the frequency distribution of pairwise nucleotide sequence identity percentages from all available genomic sequence of viruses in the same family (Bao, Y., Kapustin, Y., and Tatusova, T. (2008). Virus Classification by Pairwise Sequence Comparison (PASC). In "Encyclopedia of Virology, 5 vols." (B. W. J. Mahy, and M. H. V. Van Regenmortel, Eds.), Vol. 5, pp. 342-8. Elsevier, Oxford). The different peaks generated by the PASC program usually represent groups of virus genera, species, types, subtypes and strains (FIG. 2). In this study, we performed PASC analyses of TTV using 121 full-length genomic sequences of human and animal TTV-related strains available in GenBank database (FIG. 2). Assuming that TTV members are classified into a separate family, Anelloviridae, the two major peaks, at 36-55% and 55-67% nucleotide sequence identities, represent groups of genera and species, respectively (FIG. 2). Accordingly, a TTV type is defined as a group of TTV having 67-85% nucleotide sequence identity whereas a TTV subtype may be defined as a group of TTV sequences sharing 85-95% nucleotide sequence identity. TTV strains sharing more than 95% nucleotide sequence identity may be further classified into variants (FIG. 2). A similar classification has been proposed using sequences of 103 TTV isolates by Jelcic et al (Jelcic, I., et al. (2004). Isolation of multiple TT virus genotypes from spleen biopsy tissue from a Hodgkin's disease patient: genome reorganization and diversity in the hypervariable region. J Virol 78(14), 7498-507).

Figure 3A:
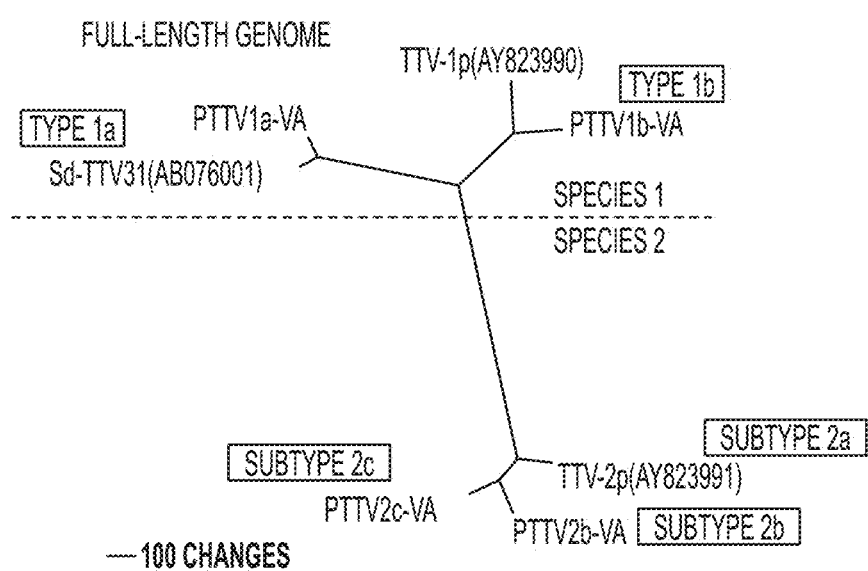
FIG. 3A illustrates a phylogenetic tree constructed by the neighbor-joining method based upon the full-length genomic nucleotide sequences.
Figure 3B:
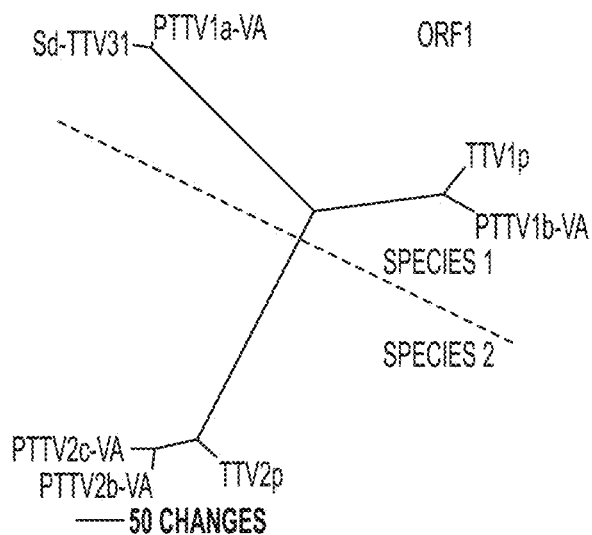
FIG. 3B illustrates a phylogenetic trees constructed based upon deduced amino acid sequences of ORF1 among seven porcine TTV strains.
Figure 3C:
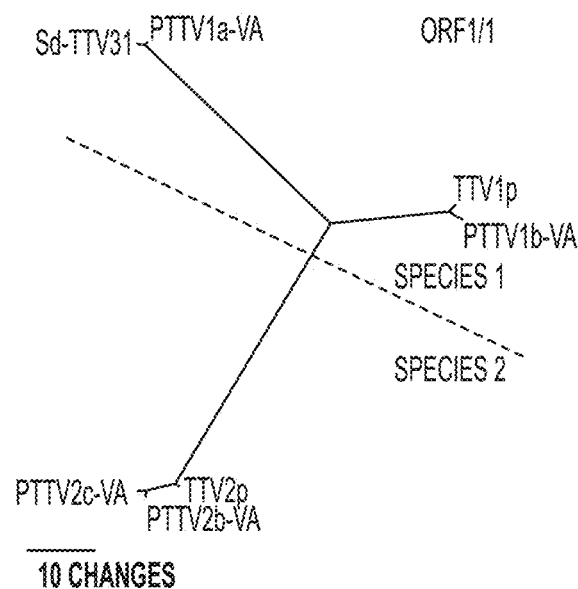
FIG. 3C illustrates a phylogenetic trees constructed based upon deduced amino acid sequences of ORF1/1 among seven porcine TTV strains.
Figure 3D:
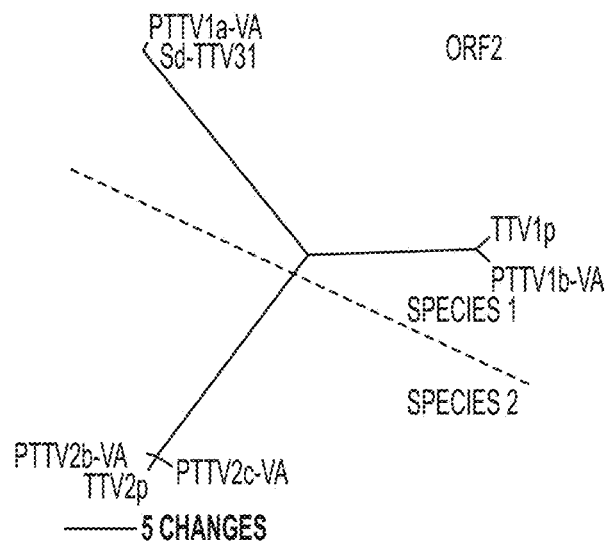
FIG. 3D illustrates a phylogenetic trees constructed based upon deduced amino acid sequences of ORF2 among seven porcine TTV strains.
Figure 3E:
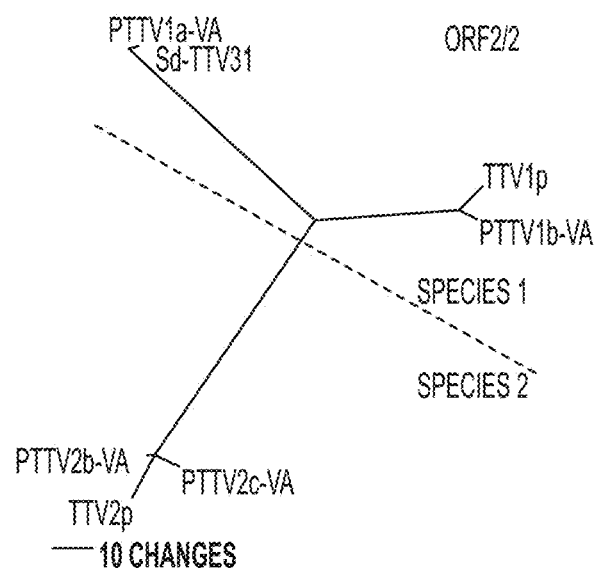
FIG. 3E illustrates a phylogenetic trees constructed based upon deduced amino acid sequences of ORF2/2 among seven porcine TTV strains.
Figure 4A:
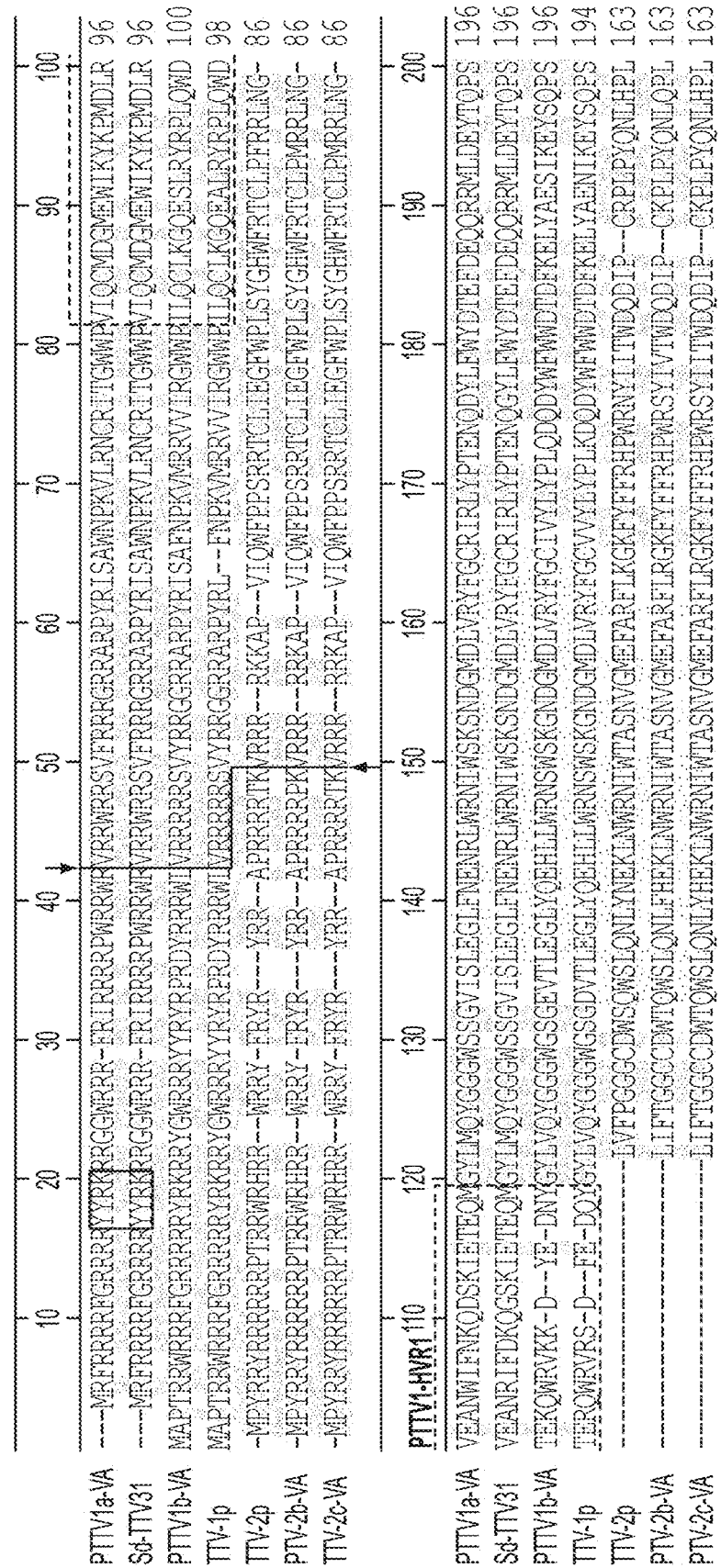
FIG. 4 represents an alignment of the full-length amino acid sequences of ORF1 among seven PTTV strains (PTTV1a-VA=SEQ ID NO: 13, Sd-TTV31=SEQ ID NO: 54, PTTV1b-VA=SEQ ID NO: 14, TTV-1p=SEQ ID NO: 57, TTV-2p=SEQ ID NO: 60, PTTV2b-VA=SEQ ID NO: 15, and PPT2c-VA=SEQ ID NO: 16)
Figure 5:
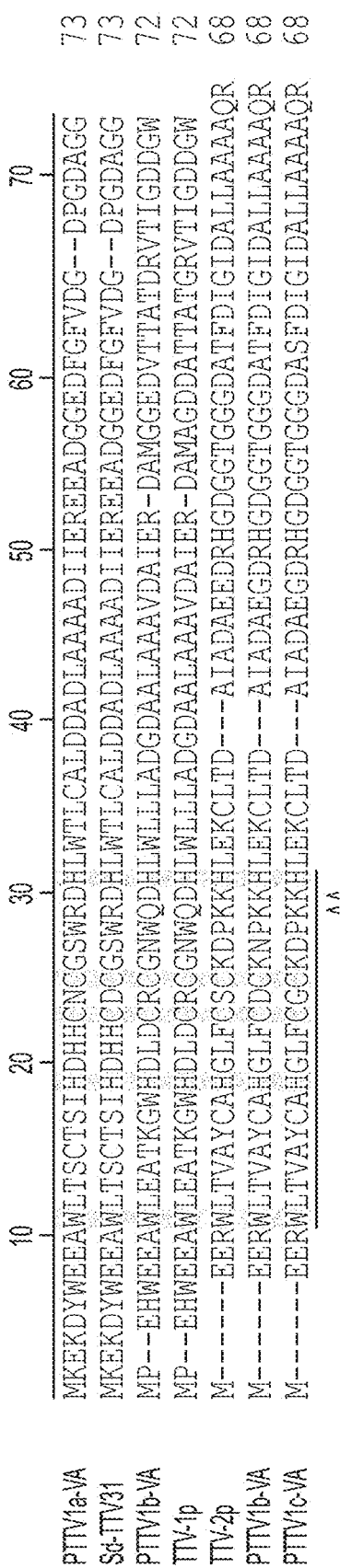
FIG. 5 represents an alignment of the full-length amino acid sequences of ORF2 among seven PTTV strains (PTTV1a-VA=SEQ ID NO: 17, Sd-TTV31=SEQ ID NO: 55, PTTV1b-VA=SEQ ID NO: 18, TTV-1p=SEQ ID NO: 58, TTV-2p=SEQ ID NO: 61, PTTV2b-VA=SEQ ID NO: 19, and PPT2c-VA=SEQ ID NO: 20)

This proposed criteria of TTV classification were applied to phylogenetic analyses of the genomic sequences of the 4 prototype U.S. strains of PTTV and the 3 other known PTTV strains. Pairwise comparison of full-length nucleotide sequences among these strains showed that the four PTTV1 strains have 54.0-56.4% nucleotide sequence identity compared to the three PTTV2 strains (Table 3). Therefore, the previously designated "genogroup" of PTTV in the literature will probably be more appropriate to designate as "species", and PTTV1 and PTTV2 probably should represent porcine TTV species 1 and species 2, respectively. PTTV species 1 consists of two types of viruses designated as type 1a (including Sd-TTV31 and PTTV1a-VA (SEQ ID NO:9)) and type 1b (including TTV-1p and PTTV1b-VA (SEQ ID NO:10)), respectively, since the nucleotide sequence identity between these two types of viruses is between 69.8-70.7% (Table 3). Sd-TTV31 and TTV1a-VA (SEQ ID NO:9) are recognized as variant strains of the same species due to their higher sequence identity (95.1%). However, the two type 1b strains, TTV-1p and PTTV1b-VA (SEQ ID NO:10), may belong to two different subtypes (nucleotide sequence identity=86.4%). For PTTV species 2, three strains are likely to be classified into separate subtypes (TTV-2p for subtype 2a, PTTV2b-VA (SEQ ID NO:11) for subtype 2b, and PTTV2c-VA (SEQ ID NO:12) for subtype 2c, respectively) based upon their 86.5-90.9% nucleotide sequence identity. This proposed new classification system for PTTV was clearly evident in the phylogenetic tree (FIG. 3A). Phylogenetic trees constructed based upon the deduced amino acid sequences of ORF1, ORF1/1, ORF2 and ORF2/2 of PTTV were also consistent with this proposed classification (FIGS. 3B to 3E).

TABLE 3

Pairwise sequence comparison of the full-length genomic sequence of the seven porcine TTV strains

| | Porcine TTV species 1 | | | | Porcine TTV species 2 | | |
| | Type 1a | | Type 1b | | Subtype 2a | Subtype 2b | Subtype 2c |
| | PTTV1a-VA | Sd-TTV31 | PTTV1b-VA | TTV-1p | TTV-2p | PTTV2b-VA | PTTV2c-VA |
| Type 1a | | | | | | | |
| PTTV1a-VA | — | 95.1 | 70.5 | 69.8 | 55.7 | 55.1 | 56.2 |
| Sd-TTV31 | | — | 70.7 | 70.1 | 55.9 | 56.0 | 56.4 |
| Type 1b | | | | | | | |
| PTTV1b-VA | | | — | 86.4 | 54.0 | 54.7 | 55.2 |
| TTV-1p | | | | — | 55.2 | 54.7 | 55.4 |
| Subtype 2a | | | | | | | |
| TTV-2p | | | | | — | 86.5 | 86.8 |
| Subtype 2b | | | | | | | |
| PTTV2b-VA | | | | | | — | 90.9 |
| Subtype 2c | | | | | | | |
| PTTV2c-VA | | | | | | | — |

The data were generated by using the PASC program, and the values indicate % nucleotide sequence identities.

Unique mutations and deletions and/or insertions are scattered throughout the genomes between PTTV species, types and subtypes. For example, the location of ORF1 initiation and termination codons and the ORF2 initiation codons between PTTV type 1a and 1b, which was shown in FIG. 1C as mentioned above, are different. The two PTTV1b strains also have a 2-codon deletion after the ORF2 initiation compared to PTTV1a (FIG. 1C).

Remarkably, both TTV-2p and PTTV2b-VA have a large 52-nt deletion, which is 39 nt upstream of the first 11-nt conserved sequence (AGTCCTCATTT (SEQ ID NO:40)) in the UTR, compared to PTTV2c-VA. Due to this deletion, the genomic size of PTTV2b-VA (probably TTV-2p as well) was significantly smaller than that of PTTV2c-VA (Table 2). A number of "subviral" human TTV clones have been isolated from serum samples that are considered as full-length TTV genomes since the ORFs in a majority of these subviral molecules usually remain intact (de Villiers et al., 2009; Leppik et al., 2007). They have variable lengths in the UTR that are completely or partially deleted. The situation of TTV-2p and PTTV2b-VA appears to resemble that of the human TTV subviral molecules, implying that subtypes PTTV2a and PTTV2b might be the subviral molecules derived from subtype PTTV2c. Of note, the 3'-terminal sequence of a nested-PCR primer TTV2-nF (Table 1) that is commonly used for detection of the PTTV2 from field samples by other groups (Ellis et al., 2008, supra; Kekarainen et al., 2007, supra; Kekarainen et al., 2006, supra; Krakowka et al., 2008, supra) is located at both sides of the deletion. Therefore, the current nested-PCR assay for PTTV2 detection is likely not sufficient to identify the genetically diverse strains of PTTV2c subtype.

The source of the isolated virus strain is serum, fecal, saliva, semen and tissue samples of pigs having the porcine TTV viral infection. However, it is contemplated that recombinant DNA technology can be used to duplicate and chemically synthesize the nucleotide sequence. Therefore, the scope of the present invention encompasses the isolated polynucleotide which comprises, but is not limited to, a nucleotide sequence set forth in SEQ ID NO:9, SEQ ID NO:10, SEQ ID NO:11, and SEQ ID NO:12, or its complementary strand; a polynucleotide which hybridizes to and which is at least 67% complementary to the nucleotide sequence set forth in SEQ ID NO:9, SEQ ID NO:10, SEQ ID NO:11, and SEQ ID NO:12, preferably 85% complementary, or more preferably 95% complementary; or an immunogenic fragment selected from the group consisting of an amino acid sequence of ORF1 protein set forth in SEQ ID NO:13 (PTTV1a-VA), SEQ ID NO:14 (PTTV1b-VA), SEQ ID NO:15 (PTTV2b-VA), SEQ ID NO:16 (PTTV2c-VA), an amino acid sequence of ORF2 protein set forth in SEQ ID NO:17 (PTTV1a-VA), SEQ ID NO:18 (PTTV1b-VA), SEQ ID NO:19 (PTTV2b-VA), SEQ ID NO:20 (PTTV2c-VA), an amino acid sequence of ORF1/1 protein set forth in SEQ ID NO:21 (PTTV1a-VA), SEQ ID NO:22 (PTTV1b-VA), SEQ ID NO:23 (PTTV2b-VA), SEQ ID NO:24 (PTTV2c-VA), an amino acid sequence of ORF2/2 protein set forth in SEQ ID NO:25 (PTTV1a-VA), SEQ ID NO:26 (PTTV1b-VA), SEQ ID NO:27 (PTTV2b-VA), SEQ ID NO:28 (PTTV2c-VA). The immunogenic or antigenic coding regions or fragments can be determined by techniques known in the art and then used to make monoclonal or polyclonal antibodies for immunoreactivity screening or other diagnostic purposes. The invention further encompasses the purified, immunogenic protein encoded by the isolated polynucleotides. Desirably, the protein may be an isolated or recombinant ORF1 protein or an ORF2 protein of at least one of the above isolated porcine TTV subtypes, more desirably ORF1 protein.

The ORF1 of porcine TTV is believed to encode a structural and replication-associated protein (Maggi, F., and Bendinelli, M. (2009). Immunobiology of the Torque teno viruses and other anelloviruses. *Curr Top Microbiol Immunol* 331, 65-90). The ORF1-encoding products of seven PTTV strains have 624-635 aa in length and possess a high number of arginine residues at the N-terminus that are thought to have the DNA-binding activity (FIG. 4). In FIG. 4, conserved sequences are shaded. Dashes indicate amino acid deletions. The RCR motifs are boxed with solid lines. Three HVRs (PTTV1-HVRs 1, 2 and 3) of PTTV1 strains and two HVRs (PTTV2-HVRs 1 and 2) of PTTV2 strains are boxed with dashed lines. The connection boundaries of ORF1/1 are indicated by arrows. The predicted rolling-circle replication (RCR) motifs (Ilyina, T. V., and Koonin, E. V. (1992). Conserved sequence motifs in the initiator proteins for rolling circle DNA replication encoded by diverse replicons from eubacteria, eucaryotes and archaebacteria. *Nucleic Acids Res* 20(13), 3279-85) are presented at different positions in different PTTV types and subtypes that may be type- or subtype-specific. RCR motif-III (YxxK) is conserved in the PTTV type 1a (aa position 14-17 of PTTV1a-VA SEQ ID NO:13) and type 1b strains (aa position 379-382 of PTTV1b-VA SEQ ID NO:14), respectively, whereas the same conserved motif identified in all three PTTV2 strains is located at aa position 482-485 of PTTV2b-VA SEQ ID NO:15 (FIG. 4). Both PTTV2b-VA SEQ ID NO:15 and PTTV2c-VA SEQ ID NO:16 also have a conserved RCR motif-II (HxQ) at aa position 331-333 of PTTV2b-VA that is absence in TTV-2p (FIG. 4).

The ORF1 proteins of PTTV strains between species 1 and species 2 share very low aa sequence identity with only 22.4 to 25.8%, which makes it difficult to identify significantly conserved aa sequences between the two species (FIG. 4). In PTTV species 1, the aa identity of ORF1 between type 1a and 1b strains are 50.3-52.7%. Three major hypervariable regions (HVR), PTTV1-HVRs 1 to 3, with a relatively high number of aa substitutions, were identified among the four PTTV1 strains, whereas two HVRs (PTTV2-HVRs 1 and 2) were observed among the three PTTV2 strains (FIG. 4). The three PTTV2 strains have an approximately 20-aa deletion in the corresponding PTTV1-HVR1 region. Moreover, the two HVRs of PTTV2 are within the corresponding PTTV1-HVR3 region (FIG. 4). These HVRs are located only in the ORF1 but not in the truncated ORF1/1. They likely play a role in evading the host immune surveillance and helping PTTV to establish a persistent infection, as suggested by studies of human TTV.

The aa sequences of ORF2 differed considerably between the four PTTV1 (PTTV1a-VA SEQ ID NO:17; PTTV1b-VA SEQ ID NO:18) and three PTTV2 (PTTV2b-VA SEQ ID NO:19; PTTV2c-VA SEQ ID NO:20) strains (FIG. 5). However, they share a conserved protein-tyrosine phosphatase (PTPase)-like motif ($Wx_7Hx_3CxCx_5H$) at the N-terminus (FIG. 4). This motif is also conserved among all human TTV, TTMV and TTMDV strains as well as CAV. The TTMV or CAV ORF2 protein also exhibited a serine/threonine phosphatase (S/T PPase) activity (Peters, M. A., Jackson, D. C., Crabb, B. S., and Browning, G. F. (2002). Chicken anemia virus VP2 is a novel dual specificity protein phosphatase. *J Biol Chem* 277(42), 39566-73). The dual specificity of the ORF2 protein is thought to regulate host gene transcription, signal transduction and cytokine responses during viral replication. Recently, mutagenesis analyses of two conserved basic aa residues before the last histidine residue of the motif in CAV revealed that the two residues affect virus replication, cytopathology in vitro and attenuation in vivo (Peters, M. A., Crabb, B. S., Washington, E. A., and Browning, G. F. (2006). Site-directed mutagenesis of the VP2 gene of Chicken anemia virus affects virus replication, cytopathology and host-cell MHC class I expression. *J Gen Virol* 87(Pt 4), 823-31; Peters, M. A., Crabb, B. S., Tivendale, K. A., and Browning, G. F. (2007). Attenuation of chicken anemia virus by site-directed mutagenesis of VP2. *J Gen Virol* 88(Pt 8), 2168-75). The two basic aa residues ("KK") are conserved in the three PTTV2 strains. However, only the first basic residue ("R") is retained in the two PTTV1a strains whereas both basic residues are substituted in the PTTV1b strains (FIG. 5). In FIG. 5, dashes indicate amino acid deletions. The five conserved amino acids within the common motif $Wx_7Hx_3CxCx_5H$ (underlined) identified in TTV, TTMV and CAV are shaded. The positions of the two basic aa residues before the last histidine of the motif, which have been shown to affect virus replication, cytopathology or in vivo attenuation in CAV, are indicated by "^".

In summary, the present invention has determined the full-length genomic sequences of four porcine TTV strains representing different genotypes or subtypes in a serum sample of a single boar in Virginia. The finding from this study clearly indicates that, similar to human TTV, multiple PTTV infections with distinct genotypes or subtypes exist and probably are common in pigs. We have also provided new information regarding the genomic organization, the degree of variability and the characteristics of conserved nucleotide and amino acid motifs of PTTV, which will improve the current PCR detection assay, aid in developing reagents for serological diagnostics and help initiate the structural and functional study of PTTV. A new classification of PTTV is also proposed in this study based upon the phylogenetic and genetic analyses of the genomic sequences of seven known PTTV strains.

The present invention also provides methods for diagnostics of porcine TTV infection by detecting viral DNA in samples of porcine TTV infected pigs or other mammals. One preferred embodiment of the present invention involves methods for detecting porcine TTV nucleic acid sequences in a porcine or other mammalian species using oligonucleotide primers for polymerase chain reaction (PCR) to further aid in the diagnosis of viral infection or disease. The diagnostic tests, which are useful in detecting the presence or absence of the porcine TTV viral nucleic acid sequence in the porcine or other mammalian species, comprise isolating viral DNA from samples of porcine TTV infected pigs or pigs suspected of infection of TTV, and performing SYBR green real-time quantitative PCR using PTTV1-specific (SEQ ID NO:29/SEQ ID NO:30) or PTTV2-specific (SEQ ID NO:31/SEQ ID NO:32) primers.

In another embodiment of the present invention, the diagnostic method may be adapted to simultaneously detect PTTV1 and PTTV2 by using PTTV1/PTTV2 duplex real-time PCR. More specifically, the method comprises isolating viral DNA from samples of porcine TTV infected pigs or pigs suspected of infection of TTV, performing real-time PCR using both PTTV1-specific (SEQ ID NO:29/SEQ ID NO:30) or PVVT2-specific (SEQ ID NO:31/SEQ ID NO:32) primers in the same real-time PCR reaction. Since the $T_m$ value between PTTV1 and PTTV2 can be distinguished by MCA, the presence of PTTV1 and PTTV2 DNA can be simultaneously detected.

In a further embodiment of the present invention, the diagnostic method may employ duplex nested PCR. The method comprises isolating viral DNA from samples of porcine TTV infected pigs or pigs suspected of infection of TTV, performing a first round of PCR using one pair of primers P1ab-mF (SEQ ID NO:33)/P1ab-mR (SEQ ID NO:34), and performing a second round of PCR using a mixture of two pairs of primers, P1a-nF (SEQ ID NO:35)/P1a-nR (SEQ ID NO:36) for detection of PTTV1a, and P1b-nF (SEQ ID NO:37)/P1b-nR (SEQ ID NO:38) for detection of PTTV1b, and visualizing the PCR products.

The above diagnostics methods maybe optimized by one skilled in the art according to well known methods in the art.

Accordingly, an embodiment of the present invention develops two novel singleplex SYBR green real-time PCR assays to quantify the viral loads of two porcine TTV species, respectively. PTTV1- and PTTV2-specific primers were designed to target the extremely conserved regions across six PTTV1 and four PTTV2 full-length genomes available to date, respectively. Another embodiment of the present invention combines the two singleplex assays into a duplex real-time PCR assay followed by MCA of the viral amplicons that can be identified by their distinct melting temperatures for simultaneous detection of the two porcine TTV species, PTTV1a and PTTV1b. In a third embodiment, a duplex nested PCR assay for simultaneous amplification of the viral DNAs from two types of PTTV1 in the first round PCR and differential detection of types 1a and 1b in the second round PCR was developed for the identification of two types of porcine TTV species, PTTV1a and PTTV1b, in a single sample. These assays represent simple and practical tools for diagnoses of species- or type-specific porcine TTVs.

Potential primers sequences were identified by multiple sequence alignments of 10 available porcine TTV full-length genomes. PTTV1-specific primers TTV1F (SEQ ID NO:29) and TTV1R (SEQ ID NO:30) were designed based upon two conserved genomic regions immediately before the putative ORF2 across six PTTV1 genomes, whereas PTTV2-specific primers TTV2F4 (SEQ ID NO:31) and TTV2R4 (SEQ ID NO:32) were designed based upon two conserved genomic regions immediately after the putative ORF2/2 across four PTTV2 genomes (Table 4). Primers showed no potentials for self- and cross-dimerization. The expected amplicon sizes were a 118-bp fragment from the PTTV1 primers corresponding to the PTTV1b-VA genome and a 200-bp fragment from the PTTV2 primers corresponding to the PTTV2c-VA genome, respectively.

TABLE 4

Oligonucleotide primers used for real-time PCR and duplex nested PCR detections of porcine TTVs.

| Primer ID | Sequence (5' to 3') | Purpose |
|---|---|---|
| TTV1F SEQ ID NO: 29 | TCCGAATGGCTGAGTTTATGC | PTTV1-specific real-time PCR |
| TTV1R SEQ ID NO: 30 | TCCGCTCAGCTGCTCCT | PTTV1-specific real-time PCR |
| TTV2F4 SEQ ID NO: 31 | GGTGGTAAAGAGGATGAA | PTTV2-specific real-time PCR |
| TTV2R4 SEQ ID NO: 32 | AATAGATTGGACACAGGAG | PTTV2-specific real-time PCR |

TABLE 4-continued Oligonucleotide primers used for real-time PCR and duplex nested PCR detections of porcine TTVs.

| Primer ID | Sequence (5' to 3') | Purpose |
|---|---|---|
| P1ab-mF SEQ ID NO: 33 | TATCGGGCAGGAGCAGCT | Duplex nested PCR |
| P1ab-mR SEQ ID NO: 34 | TAGGGGCGCGCTCTACGT | Duplex nested PCR |
| P1a-nF SEQ ID NO: 35 | CCTACATGAAGGAGAAAGACT | Duplex nested PCR |
| P1a-nR SEQ ID NO: 36 | CCAGCGTCTCCAGGGTC | Duplex nested PCR |
| P1b-nF SEQ ID NO: 37 | AAGCTACCAAGGGCTGG | Duplex nested PCR |
| P1b-nR SEQ ID NO: 38 | GCGGTC(T/G)GTAGCGGTAGT | Duplex nested PCR |

According to one specific embodiment of the present invention, SYBR green simplex real-time PCR using PTTV1- and PTTV2-specific primers can be used specifically to detect porcine TTV1 and TTV2 DNA, respectively. For PTTV1, a standard curve was established over a range of target DNA concentrations per 25 µl. The linear range was shown to span $4.4 \times 10^1$ to $4.4 \times 10^8$ copies. The minimum detection limit (44 copies) corresponded to a threshold cycle ($C_t$) of 37.57. For PTTV2, standard curve was also generated and used to detect DNA concentration ranging from $8.6 \times 10^0$ to $8.6 \times 10^8$ copies per 25 µl reaction. The corresponding $C_t$ of minimum detection limit (8.6 copies) was 36.53.

Figure 7A:
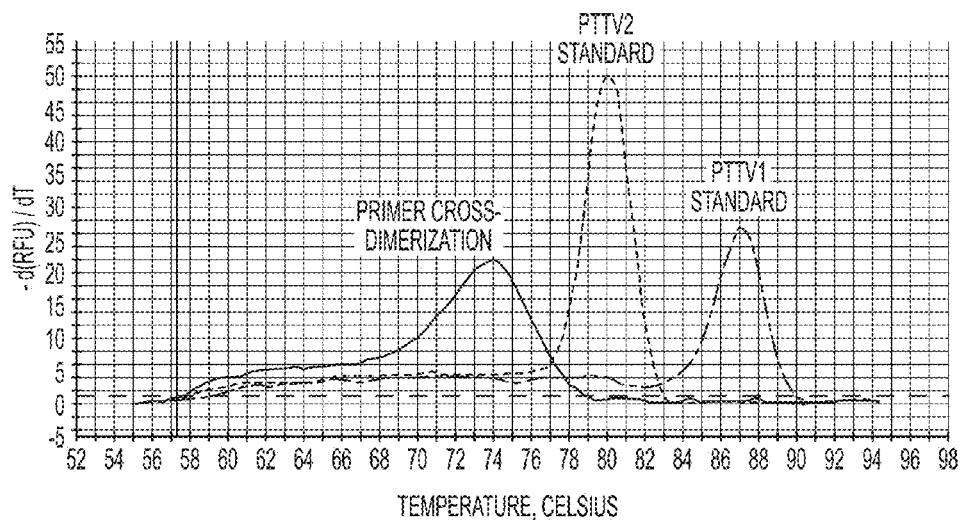
FIGS. 7A-7E illustrate melting curve analysis (MCA) of PTTV1/PTTV2 SYBR green-based duplex real-time PCR.
Figure 7B:
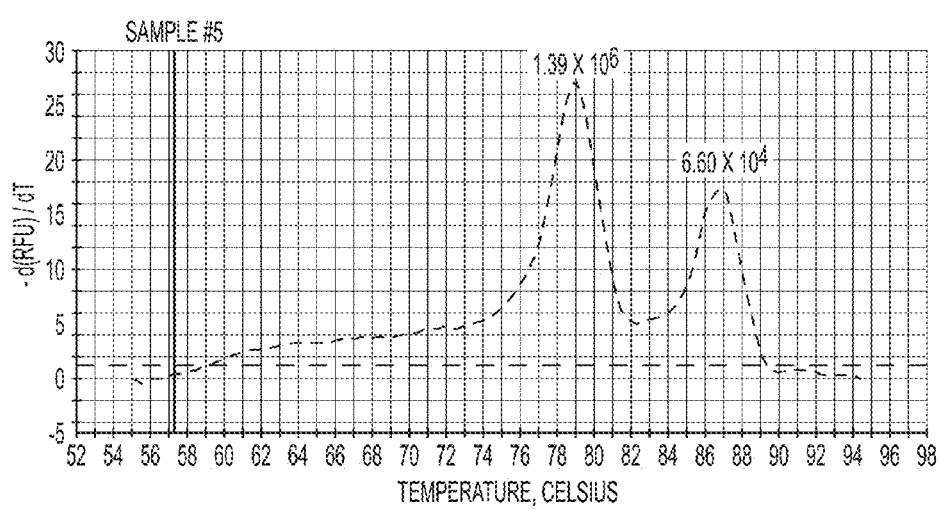
Figure 7C:
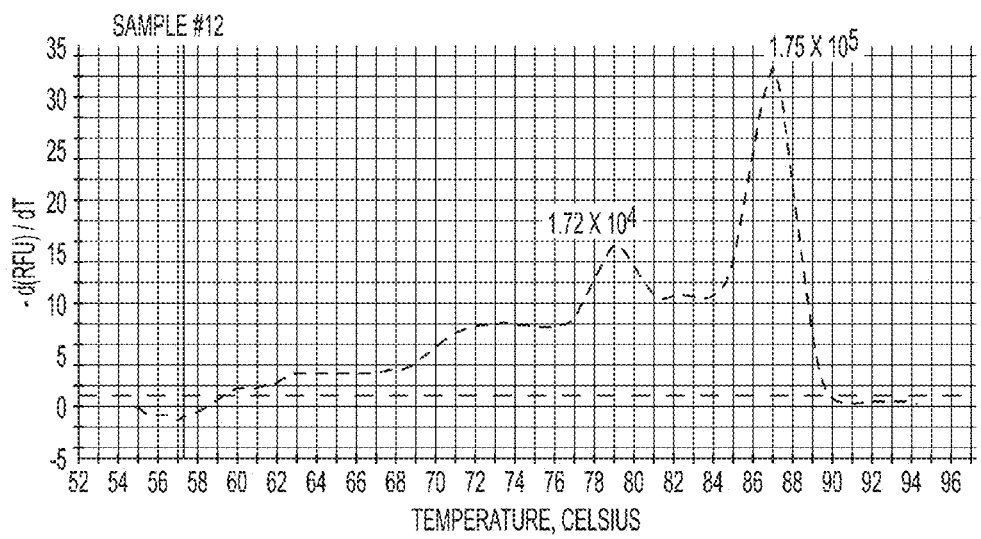
Figure 7D:
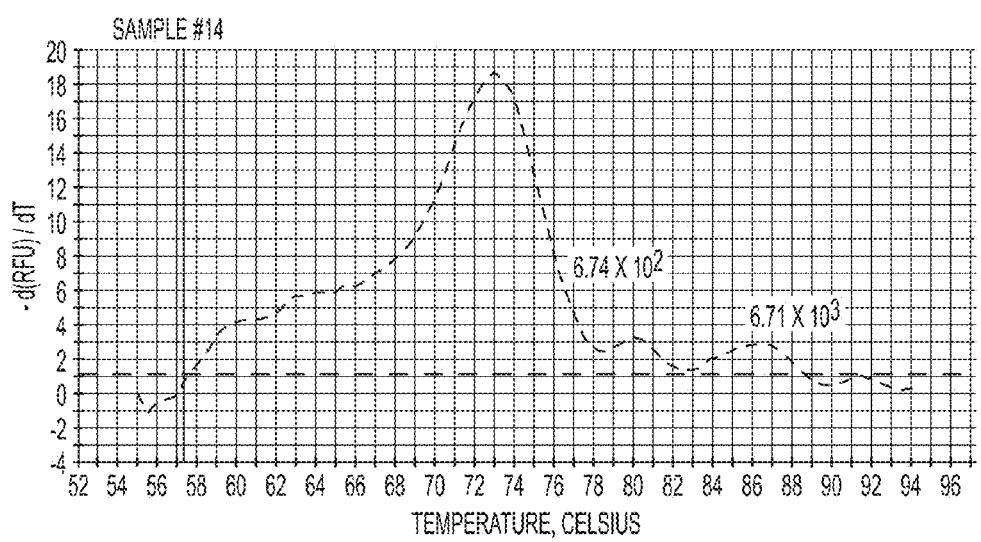
Figure 7E:
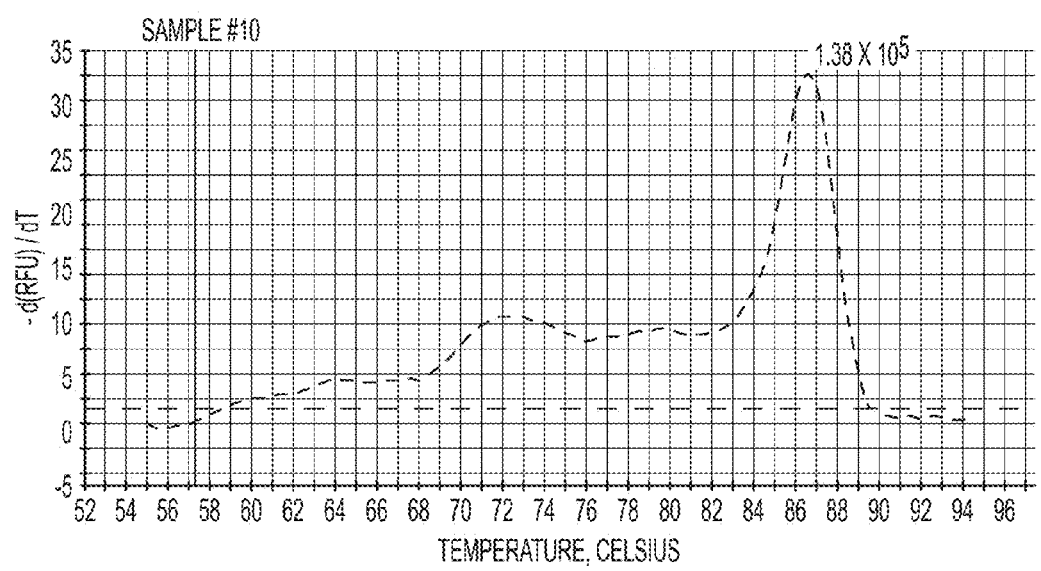

According to another specific embodiment of the present invention, SYBR green duplex real-time PCR is utilized for the simultaneous detection of porcine TTV1 and TTV2 DNA. The 7-degree difference of $T_m$ value between PTTV1 (87.0° C.) and PTTV2 (80.0° C.) made it feasible to distinguish them from one another by the MCA. Therefore, two singleplex assays can be coupled into a duplex real-time PCR assay for the simultaneous detection of PTTV1 and PTTV2. A positive sample was one that had a symmetrical melt peak within the known $T_m$ for that product. This new assay was first validated by using a 10-fold dilution of PTTV1 and PTTV2 standards mixture. The non-template negative control using sterile water as the template showed a non-specific amplification caused by cross-dimerization between the PTTV1 and PTTV2 primers not seen in the singleplex assays (FIG. 7a). This produced a distinct melt peak between 72.0° C. and 76.0° C. FIG. 7A shows melt peaks of PTTV1 standard (red; $T_m$=87.0° C.), PTTV2 standard (green; $T_m$=80.0° C.) and non-template negative control (caused by primer cross-dimerization; black). FIGS. 7B-7E show melt peaks of representative serum samples with distinct viral loads of PTTV1 and PTTV2. FIG. 7B shows boar serum sample no. 5: relatively high viral loads of both PTTV1 and PTTV2, but PTTV2>PTTV1; FIG. 7C shows boar serum sample no. 12: relatively high viral loads of both PTTV1 and PTTV2, but PTTV1>PTTV2; FIG. 7D shows boar serum sample no. 14: low viral loads of both PTTV1 and PTTV2; FIG. 7E shows boar serum sample no. 10: PTTV1 positive, but PTTV2 negative. The viral loads (unit: genomic copies/ml) of PTTV1 and PTTV2 in each sample that were determined by singleplex real-time PCR were indicated at the top of the corresponding melt peak.

In one example, when the duplex real-time assay was applied to the 20 serum samples of adult boars, samples with relatively high viral loads of both PTTV1 and PTTV2 displayed two distinct melt curves corresponding to PTTV1 and PTTV2 without a non-specific melt peak (FIGS. 7B & 7C), whereas samples with low viral load of either PTTV1 or PTTV2 showed virus-specific as well as non-specific melt curves (FIGS. 7D & 7E). Although the two melt peaks in sample #14 were very small, they were considered positive since they displayed a visually distinct and symmetrical rise and fall at the appropriate $T_m$ of PTTV1 and PTTV2 (FIG. 7D). In contrast, sample #10 was considered only PTTV1 positive because a symmetrical PTTV2 melt peak was not evidently present (FIG. 7E). These results were consistent with that of the two singleplex assays (Table 5). Moreover, the size and shape of melt peaks qualitatively reflected the corresponding viral load in the detected sample.

According to another aspect of the present invention, duplex nested PCR is used for differential detection of two porcine TTV types, PTTV1a and PTTV1b.

Figure 8:
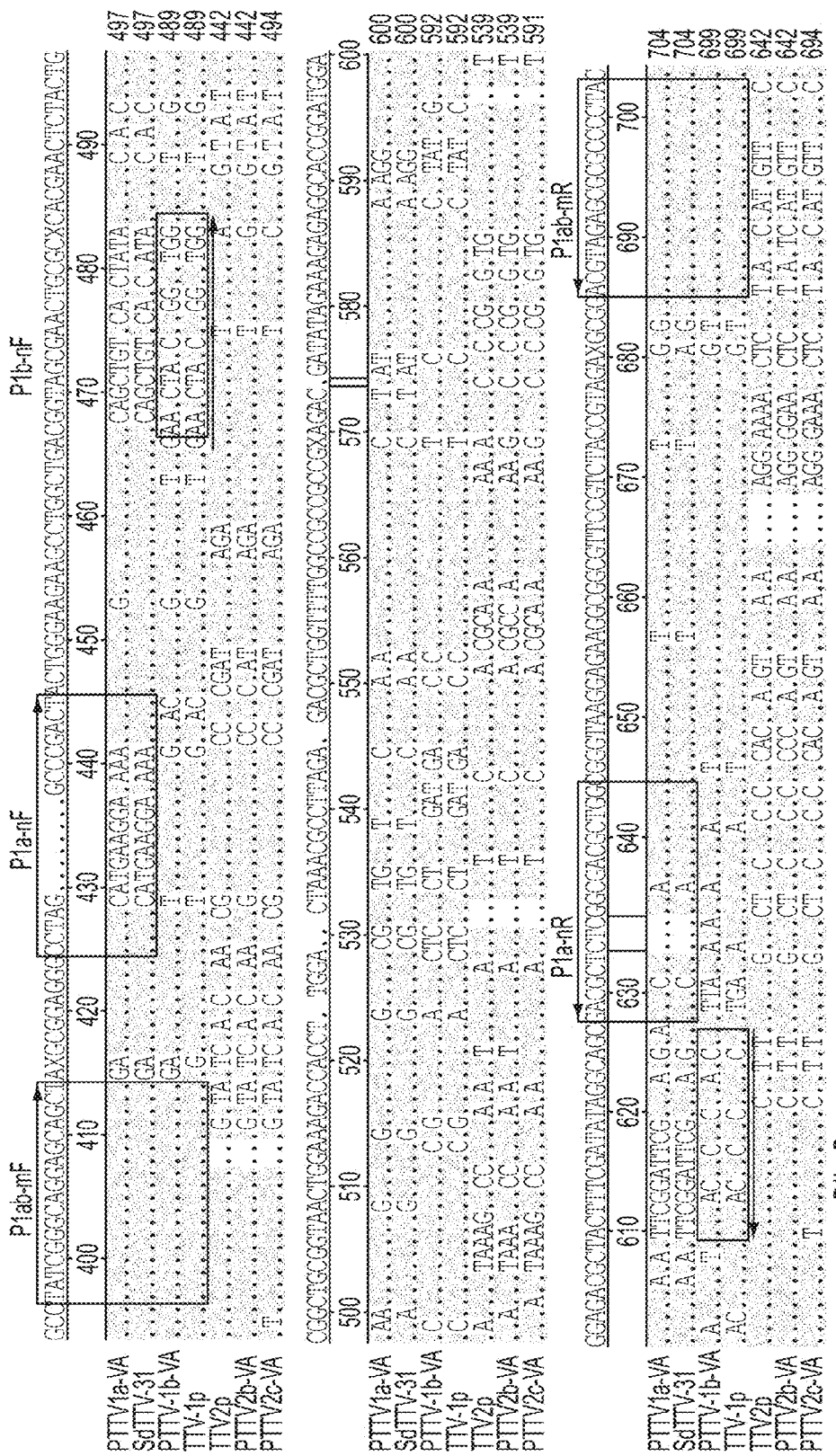
FIG. 8 represents an alignment of nucleotide sequences located at the N-terminal part of the putative ORF1 among seven PTTV strains (PTTV1a-VA=SEQ ID NO: 9, Sd-TTV31=SEQ ID NO: 53, PTTV1bVA=SEQ ID NO: 10, TTV-1p=SEQ ID NO: 56, TTV-2p=SEQ ID NO: 59, PTTV2b-VA=SEQ ID NO: 11, and PTTV2c-VA=SEQ ID NO: 12)

The inventor of the present invention demonstrated the existence of two distinct genotypes, tentatively named PTTV1a and PTTV1b, in porcine TTV species 1. To further determine whether the co-infection of PTTV1a and PTTV1b is common in pigs, a novel duplex nested PCR assay to quickly distinguish between the two was developed. Alignment of porcine TTV genomic DNA sequences identified a conserved genomic region located at the N-terminal part of the putative ORF1 encoding the viral capsid protein (FIG. 8). This region also contains the entire ORF2 and the partial UTR in the upstream. Primers P1ab-mF (SEQ ID NO:33)/P1ab-mR (SEQ ID NO:34) were designed to simultaneously amplify both PTTV1a and PTTV1b DNAs in the first-round PCR. A mixture of PTTV1a-specific primers P1a-nF (SEQ ID NO:35)/P1a-nR (SEQ ID NO:36) and PTTV1b-specific primers P1b-nF (SEQ ID NO:37)/P1b-nR (SEQ ID NO:38) was used to differentially amplify each genotype in the second-round PCR. The final PCR products of PTTV1a and PTTV1b were 162 bp and 96 bp in sizes, respectively, which could be easily distinguished by gel electrophoresis on a 1% agarose gel stained with ethidium bromide. This assay was not expected to detect PTTV2 DNA due to the specificity of primers (FIG. 8). In FIG. 8, conserved sequences were indicated by dots and shaded. Dashes indicated nucleotide deletions. The locations and directions of three pairs of primers used for duplex nested PCR were marked by arrows.

In one example, the 20 serum samples from adult boars that were subjected to the duplex nested PCR assay were all found to be positive for both PTTV1a and PTTV1b, as determined by visualizing two bands of the expected sizes and subsequent sequencing confirmation of PCR products (data not shown). No PCR products were amplified in the 19 semen samples, which was consistent with the results of PTTV1 conventional nested PCR and real-time PCR assays described above.

Infection of pigs with the two species of porcine TTV has been found back to 1985 in Spanish pig farms according to a retrospective investigation (Segales et al., 2009, supra). However, whether porcine TTVs are associated with any particular pig diseases remains elusive. Since both of porcine TTV species have a high prevalence in domestic pigs, determination of TTV viral loads is presumably more important than assessing the presence of TTV DNA. The level of viral loads in serum and semen samples has been indicated as an important marker for PCVAD in PCV2 infection (Opriessnig et al., 2007, supra). Therefore, establishment of quantitative PTTV-specific real-time PCR assays would help identify potential disease conditions associated with porcine TTVs.

Two TaqMan probe-based real-time PCR assays have recently been described. The singleplex assay developed by a Canadian group was not species-specific and was only designed to quantify the total viral loads of two PTTV species (Brassard et al., 2009, supra). The duplex assay established by a Germany group allowed the specific and simultaneous detection of both species (Gallei et al., 2009, supra). The target sequences of primers used in those two assays were determined by alignment of the three porcine TTV genomic sequences (Sd-TTV31, TTV-1p and TTV-2p) and were located in the UTR. In the present study, with 7 additional complete PTTV genomic sequences available (4 PTTV1 and 3 PTTV2 sequences), we analyzed and re-determined the conserved regions across the 10 full-length PTTV genomes. Based upon the updated alignment result from this study, two species-specific singleplex SYBR green-based real-time PCR assays were developed to quantify the viral loads of PTTV1 and PTTV2, respectively. The primers used in our assays were designed to bind to conserved genomic regions distinct from the previous studies, which may increase the accuracy of quantification. Our assays showed a considerable species-specificity and sensitivity of detection with 44 genomic copies for PTTV1 and 8.8 genomic copies for PTTV2 per 25-µl reaction, whereas the detection limit of 10 genomic copies per reaction was reported in the TaqMan probe-based duplex real-time PCR (Gallei et al., 2009, supra). In addition, the SYBR green-based real-time PCR assay is a flexible and inexpensive approach that can be directly carried out without the need to use fluorescently labeled probes. Finally, considering porcine TTVs exhibit a high degree of genetic diversity, the results from SYBR green-based assays are unlikely affected by the different genetic background of porcine TTV variants that likely contain mutations in the probe-binding sequences in the TaqMan probe-based assays.

In spite of the presence of TTV DNA, all serum samples from healthy pigs tested in this study had low amounts of PTTV1 and PTTV2 that were less than $2 \times 10^6$ copies/ml. Moreover, only an extremely low titer of PTTV2 DNA was detected in three semen samples. Most of the tested serum samples were also positive for PCV2 DNA as determined by conventional nested PCR (data not shown). Many PCV2-positive pigs with low viral load do not develop clinical PCVAD. A proposed threshold for developing PCVAD is $10^7$ or greater PCV2 genomic copies/ml of serum (Opriessnig et al., 2007, supra). In addition, semen PCV2 DNA-positivity is also a notable marker of diseased status (Opriessnig et al., 2007, supra; Pal, N., Huang, Y. W., Madson, D. M., Kuster, C., Meng, X. J., Halbur, P. G. and Opriessnig, T., 2008. Development and validation of a duplex real-time PCR assay for the simultaneous detection and quantification of porcine circovirus type 2 and an internal control on porcine semen samples. J Virol Methods 149, 217-25). The situation of species-specific PTTV may be analogous to that of PCV2 and a high PTTV titer greater than $10^7$ copies/ml may be required for the induction of porcine diseases. The species-specific real-time PCR assays developed in this study will offer simple and practical tools for future investigations of PTTV association with diseases using a large number of clinical samples from various disease conditions.

Furthermore, by coupling the two species-specific singleplex assays, we developed and validated a quick, inexpensive and reliable screening for the simultaneous detection and differentiation of the two porcine TTV species, PTTV1 and PTTV2, in a MCA-based duplex real-time PCR assay. Although this assay is not intended for accurate quantification of both PTTV species, it is a more convenient approach that could replace the conventional nested PCR for detection purpose. In comparison with real-time PCR, the conventional nested PCR assay for porcine TTVs detection is time-consuming (requiring total 4 rounds of PCR), laborious and prone to sample contamination occurring during multiple rounds of PCR processing. Due to the difference of $T_m$ value between PTTV1 and PTTV2 species, an MCA following duplex PCR amplification is able to ensure distinct reaction specificity. Another advantage of this duplex real-time assay is that inclusion of PTTV1 and PTTV2 standards is dispensable when performing the described protocol, which makes it easier for much wider use in any diagnostic labs equipped with an automated real-time PCR instrument.

Multiple infection of porcine TTVs with distinct genotypes or subtypes of the same species has been demonstrated (Gallei et al., 2009, supra). In particular, our previous study showed that porcine TTV species 1 consists of two distinct types, PTTV1a (including strains Sd-TTV31 and PTTV1a-VA) and PTTV1b (including strains TTV-1p and PTTV1b-VA). The two newly published PTTV1 isolates with full-length genomes, swSTHY-TT27 (GQ120664) from Canada and TTV1 #471819 (GU188045) from Germany, were both classified into type 1b based upon the phylogenetic analysis (data not shown). The duplex nested PCR described in this study confirmed that dual infection of two PTTV1 genotypes frequently occurred in pigs. This novel assay is the first diagnostic PCR approach developed to distinguish between PTTV1a and 1b so far. Since it is currently not known whether one or both of PTTV1a and PTTV1b infection represents a relevant factor associated with diseases, our differential PCR assay should be of great value for future potential disease associations of these two PTTV types.

According to another aspect of the invention, porcine TTV ORF proteins were expressed and used in immunodetection assays to detect the presence of porcine TTV specific antibodies. In one embodiment of the present invention, three truncated and Histidine-tagged ORF1 proteins of PTTV1a, PTTV1b and PTTV2, were expressed and purified in Escherichia coli (E. coli), respectively. Furthermore, both serum Western blot and ELISA assays based on these recombinant antigens were developed and validated using porcine serum samples from different sources. In particular, serological testing using the PTTV1a-, PTTV1b- and PTTV2-specific ELISA provides an accurate and simple tool for revealing the association of porcine TTV infection with diseases.

Figure 10A:
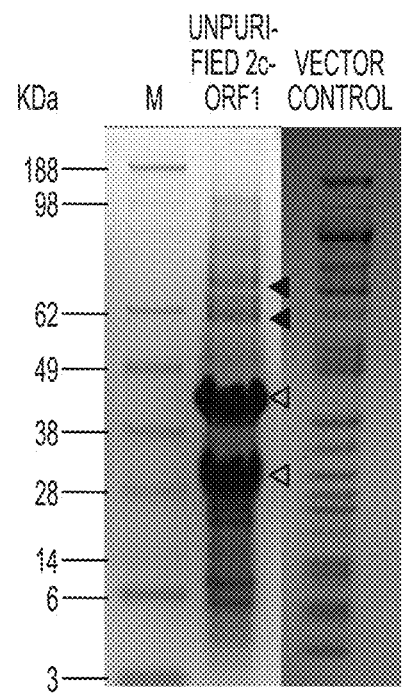
FIGS. 10A-10C illustrate the expression and purification of recombinant PTTV2c ORF1 capsid protein.
Figure 10B:
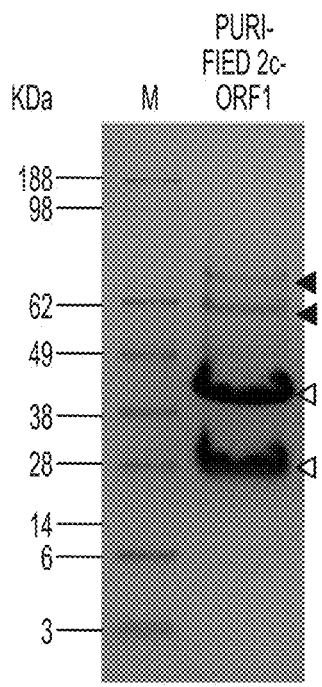
Figure 10C:
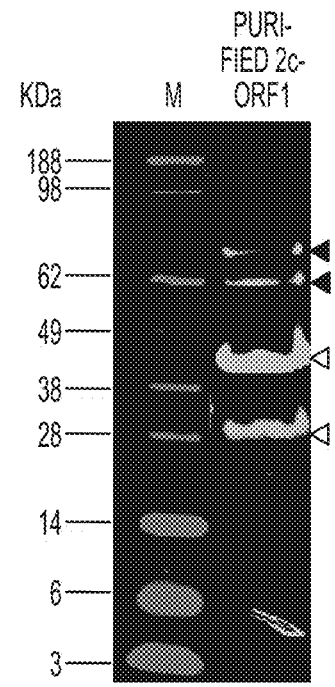
Figure 11A:
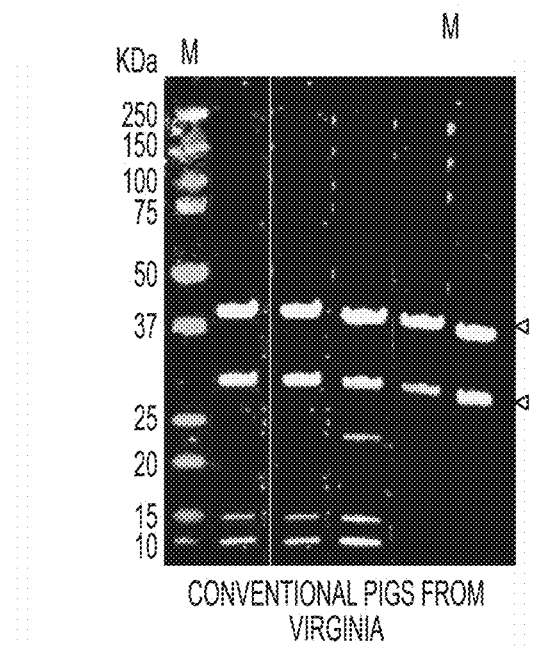
FIGS. 11A-11C show representative results of Western blot analyses of selected porcine serum samples.
Figure 11B:
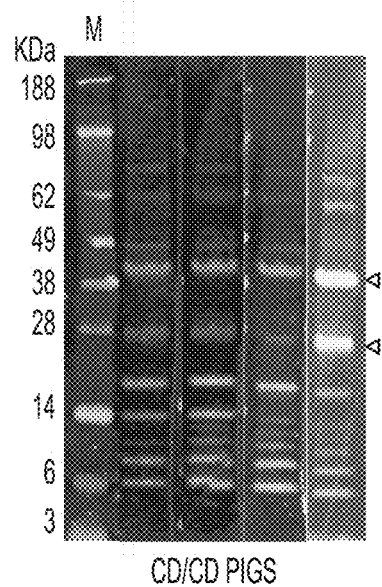
Figure 11C:
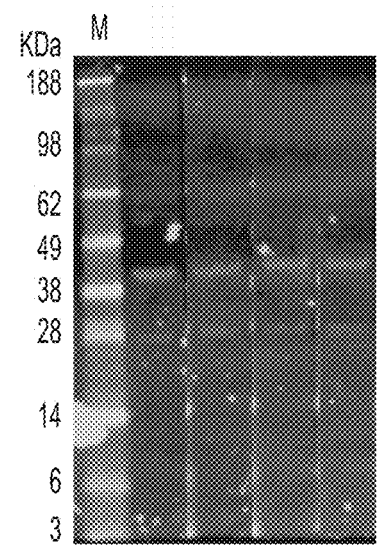
Figure 12:
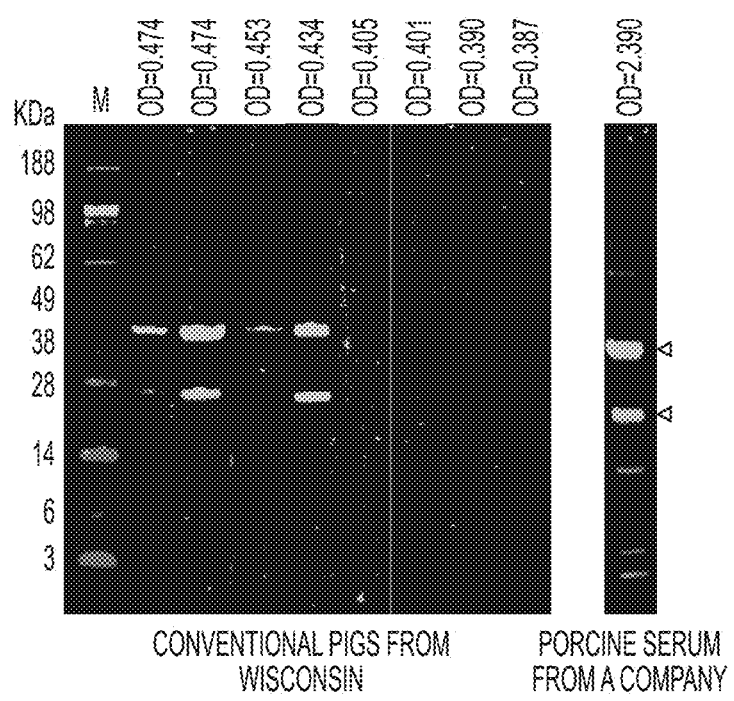
FIG. 12 illustrates the consistency of PTTV2c-ORF1-based Western blot and ELISA.
Figure 13:
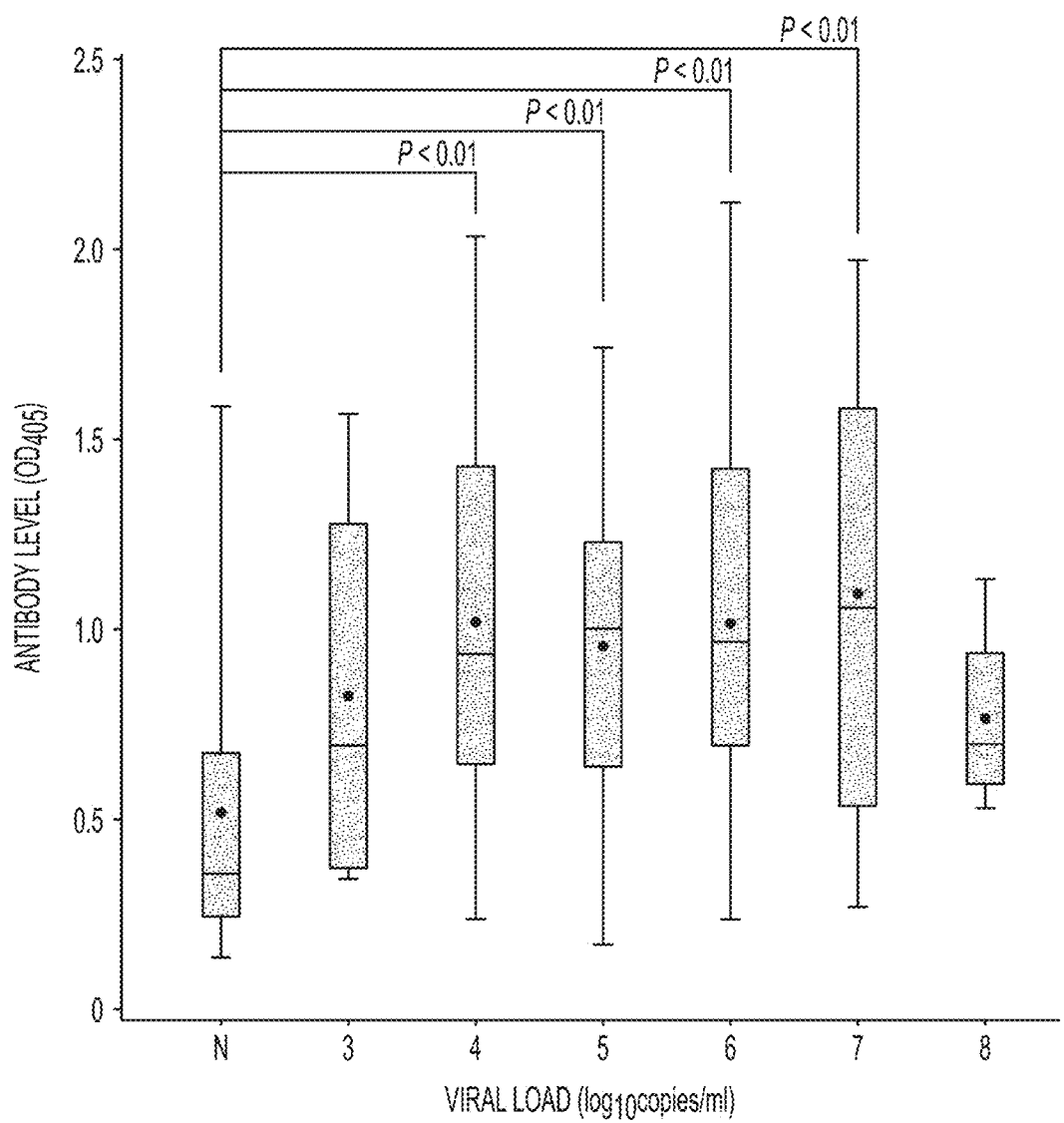
FIG. 13 shows Box-and-Whisker-plots of PTTV2 serum antibody level by viral load in 138 pigs from different sources.
Figure 14A:
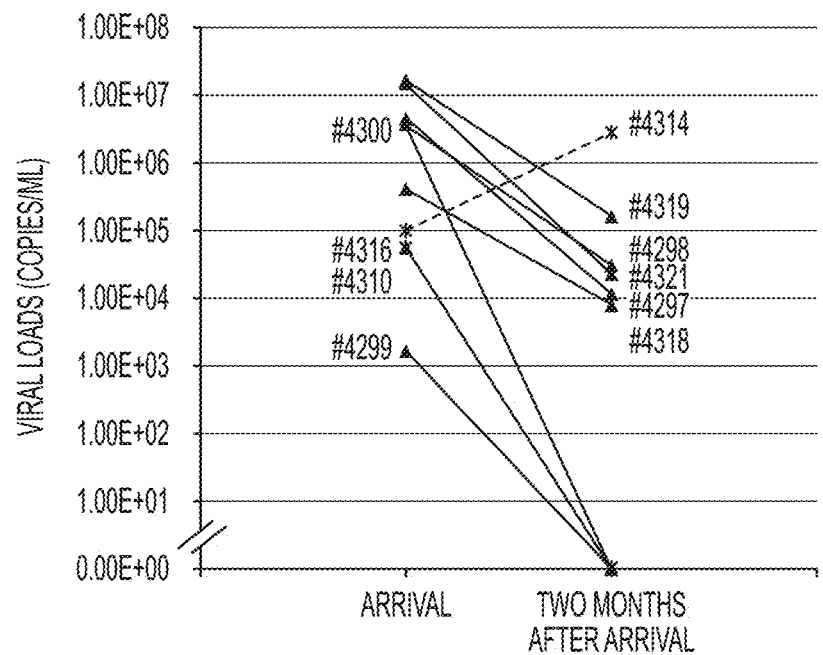
FIG. 14A illustrates a retrospective evaluation of the viral load of PTTV2.
Figure 14B:
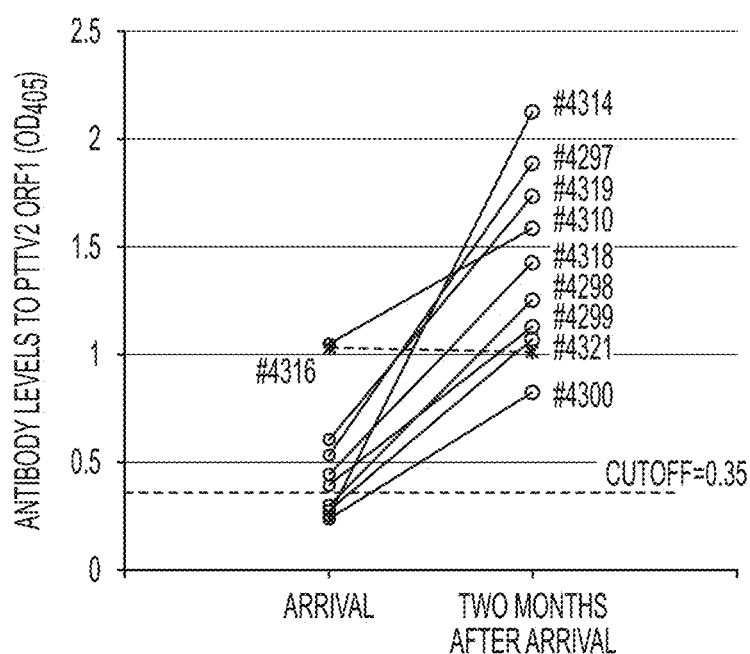
FIG. 14B illustrates antibody level to PTTV2 ORF1 capsid protein in 10 pigs growing from arrival to two months after arrival.
Figure 15A:
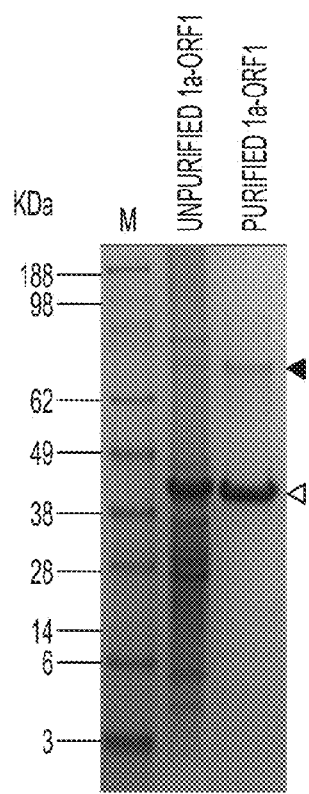
FIGS. 15A-15C illustrate the expression and purification of PTTV1a and PTTV1b recombinant ORF1 capsid protein.
Figure 15B:
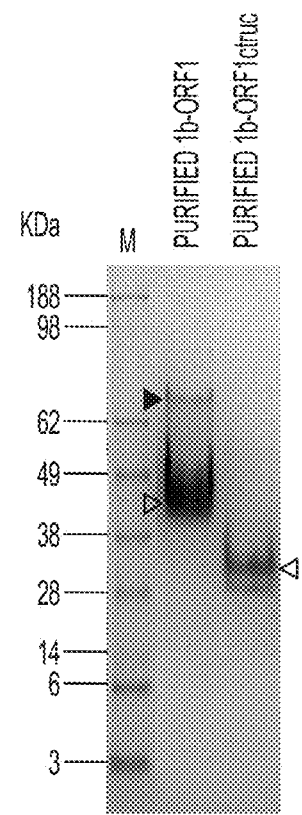
Figure 15C:
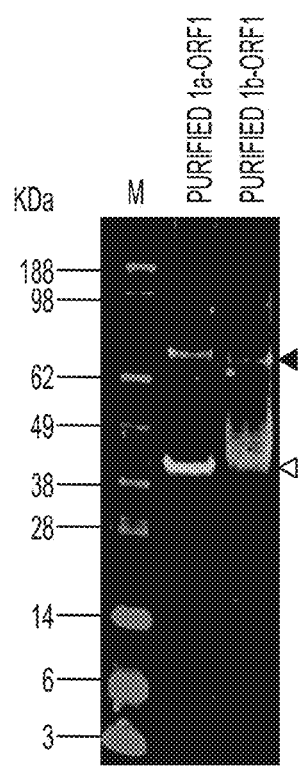

According to a further aspect of the invention, porcine TTV ORF proteins were expressed and purified as recombinant ORF1 capsid protein in E. coli expression system (FIG. 10, FIG. 15). Three truncated and His-tagged ORF1 capsid proteins of PTTV1a, PTTV1b and PTTV2, were expressed and purified in Escherichia coli (E. coli), respectively, and served as recombinant capsid subunit vaccines against PTTV infection.

Figure 9A:
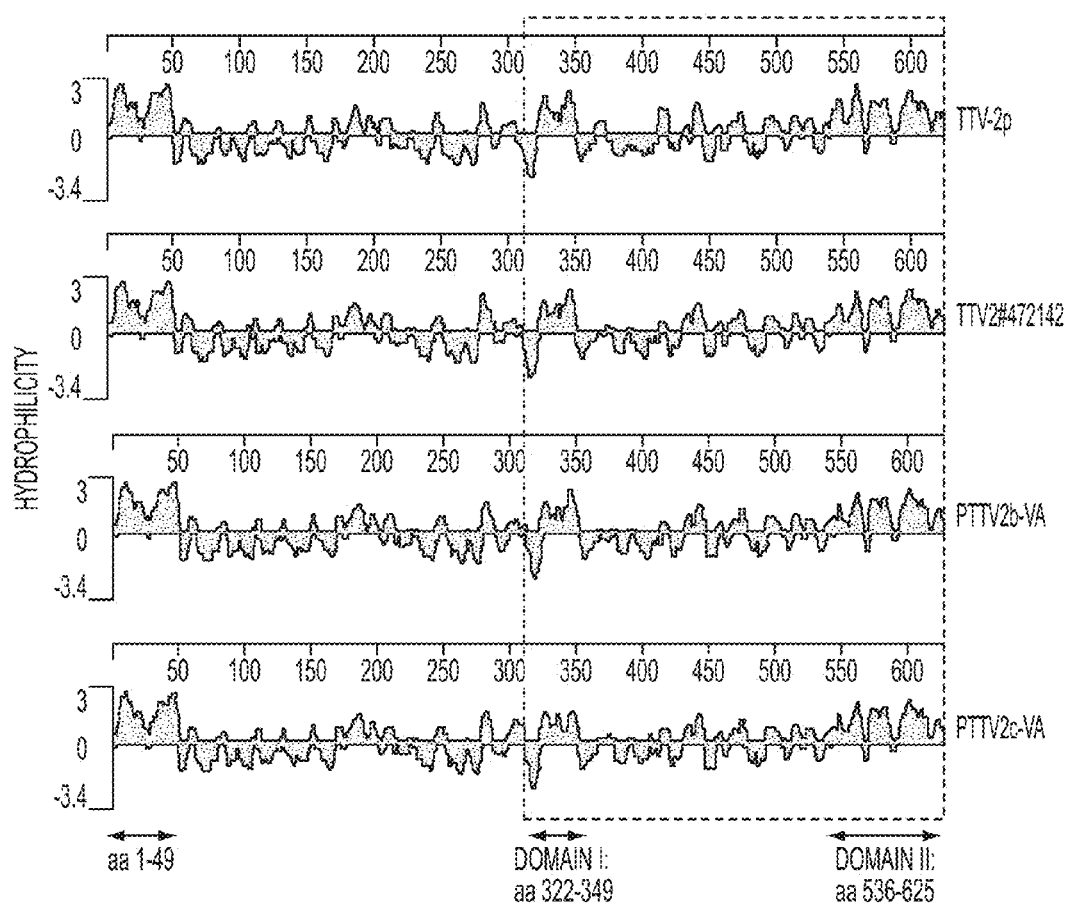

Four porcine TTV2 strains, TTV-2p, TTV2#472142, PTTV2b-VA and PTTV2c-VA, had available complete genomic sequences to date. Although they are phylogenetically classified into three putative subtypes, a comparative analysis of hydrophilicity profiles of the ORF1 encoding amino acids from four PTTV2 showed that they shared three hydrophilic regions, an arginine-rich region from aa 1-49 at the N-terminal and two particular domains (I and II) located at the middle and C-terminal part, respectively (FIG. 9A). The C-terminal region used for truncated PTTV2c-VA ORF1 expression and the corresponding regions shared in other three PTTV2 strains were indicated by a dashed box. Alignments of amino acid sequences demonstrated high levels of sequence conservation of domains I (aa 322-349) and II (aa 536-625) across the four PTTV2 strains (FIG. 9B).

Since hydrophilic domains are believed to be important for the antigenicity of many proteins, the C-terminal region (aa 310-625) of the PTTV2c-VA ORF1 SEQ ID NO:16 containing the two domains was chosen for protein expression, which would be used as antigen for PTTV2-specific antibody detection in porcine serum. According to one aspect of the invention, expression of the truncated PTTV2c ORF1 was sufficient for detection of all PTTV2 subtypes (2a, 2b and 2c; also see FIG. 3A).

According to one embodiment of the present invention, the C-terminal part of the PTTV2c ORF1 gene fused with 8×His-tags was constructed and expressed in *E. coli*. The recombinant protein was insoluble and expressed within the bacterial inclusion bodies. FIG. 10A shows SDS-PAGE of unpurified 2c-ORF1 products. FIG. 10B shows SDS-PAGE of purified 2c-ORF1 products. FIG. 10C shows Western blot analysis of purified 2c-ORF1 products using an anti-His-tagged mAb. White arrowheads indicated the ORF1 protein with the expected size and its truncated product whereas black arrowheads show the putative dimers of the expected and truncated proteins. M: protein markers. In FIG. 10A, two significant polypeptides (white arrowheads) were produced in the 2c-ORF1 unpurified sample in comparison with the control sample. The band of ~40 KDa was consistent with the expected size of 2c-ORF1 whereas the ~30 KDa polypeptide was probably an N-terminally truncated product from the former. After purification with a nickel-affinity column, four polypeptides including the two described significant bands were showed in SDS-PAGE (FIG. 10B). They were also detected by western blot using an anti-His-tagged mAb (FIG. 10C). Two high-molecular-mass bands (black arrowheads) were the homodimers formed by the two polypeptides of ~40 KDa and ~30 KDa, respectively, based on the predicted sizes (~80 KDa and ~60 KDa). The results demonstrated that the purified C-terminal PTTV2c-ORF1 was successfully produced and could be used for porcine TTV2 antibody detection in porcine sera.

According to another aspect of the present invention, porcine TTV2 antibodies in various porcine serum samples can be detected by Western blot using purified C-terminal PTTV2c-ORF1. White arrowheads indicated the ORF1 protein with the expected size and its truncated product. It should be noted that only the bands in green color were recognized as positive. A total of more than 200 serum samples of conventional pigs (healthy or diseased), CD/CD pigs and gnotobiotic pigs from different sources were collected. Samples were randomly selected for detection of anti-PTTV2c-ORF1 IgG antibodies using the purified C-terminal PTTV2c-ORF1 as antigen. FIG. 11A shows results of Western blot analyses of selected porcine serum samples of conventional pigs, FIG. 11B shows CD/CD pigs, and FIG. 11C shows gnotobiotic pigs. Purified PTTV2c-ORF1 products were used as the antigens. The two marked ~40 KDa and ~30 KDa bands were detected in most samples of the conventional pigs (FIG. 11A) and CD/CD pigs (FIG. 11B), indicating widely PTTV2 infection in these pigs. However, all the gnotobiotic pigs from two different sources (Blacksburg, V A and Ames, Iowa) had no detectable PTTV2 antibody (FIG. 11C). Additional low-molecular-mass bands were also observed (FIGS. 11A and 11B). They were likely from non-specific reactivity in the Western blot.

According to yet another aspect of the present invention, PTTV2-specific ELISA can be used as a porcine TTV2 serological test. Seronegative results were also shown in a few samples from conventional pigs of a Wisconsin farm (FIG. 12). These negative samples were pooled and used as a negative reference in development of a PTTV2-specific ELISA. The remaining samples from this source were positive (FIG. 12, the four lanes in the left). In addition, porcine sera from a commercial company used in cell culture (supposed to be OIE diseases-free) also displayed strong anti-PTTV2-ORF2 positivity (FIG. 12), which was used as a positive control for ELISA. The concentrations of purified 2c-ORF1 antigen, porcine sera and IgG conjugate were determined by checkboard titration to present low background signal and give the highest difference of $OD_{405}$ value between the positive and negative controls. The optimal antigen amount was 69 ng per well, and the optimal ELISA results were obtained by use of a 1:100 dilution of serum samples and a 1:4000 dilution of IgG conjugates. The ELISA cutoff values ranged from 0.25 to 0.5 in each trial. FIG. 4 shows a representative result reflecting the consistency of serum western blot and the developed ELISA.

138 conventional pig sera samples from 3 herds were chosen to analyze the correlation between PTTV2 viral load by real-time PCR and anti-PTTV2 IgG antibody level by ELISA. The results showed that pigs with undetectable or higher PTTV2 viral load ($10^8$ copies/ml) were more likely to have a lower serum PTTV2 antibody titer than pigs with middle values of PTTV2 viral load (FIG. 13).

In particular, sera from 10 pigs in the same herd were also analyzed by comparing the PTTV2 viral loads and anti-PTTV2 antibody levels of their sera from their arrival in the new facility to two months after arrival. Nine of the 10 pigs had decreased viral loads (three had no detectable virus) after 2 months whilst the anti-PTTV2 antibody titers increased in nine of 10 pigs (FIGS. 14A and 14B). The results suggested that the 10 pigs acquired PTTV2 infection at early stage, which induced humoral response and produced anti-ORF1 capsid IgG antibody progressively. The PTTV2-ORF1 IgG antibody was able to neutralize or even clear the virus, indicating the ORF1 indeed encode a viral capsid protein and may contain neutralizing epitopes against PTTV2.

According to one embodiment of the present invention, the C-terminal PTTV1a- and PTTV1b-ORF1 proteins were expressed and purified in *E. coli* system, respectively. SDS-PAGE and western blot analysis using an anti His-tagged mAb showed that both 1a- and 1b-ORF products had two polypeptides, one with expected size (~40 KDa) and another as the putative homodimer (~80 KDa) (FIG. 15A-C). FIG. 15A shows SDS-PAGE of unpurified and purified 1a-ORF1 products. FIG. 15B shows SDS-PAGE of purified 1b-ORF1 and 1b-ORF1ctruc products. FIG. 15C shows Western blot analysis of purified 1a- and 1b-ORF1 products using an anti-His-tagged mAb. White arrowheads indicate the ORF1 protein with the expected size whereas black arrowheads show the putative dimer of the ORF1 proteins. Compared to 2c-ORF1 expression, no truncated polypeptide was observed. As a comparative control, expression of a C-terminal-truncated 1b-ORF1 region (1b-ORF1ctruc) resulted in a lower-molecular-mass polypeptide compared to its C-terminal-non-truncated counterpart 1b-ORF1 (FIG. 15B).

Figure 16:
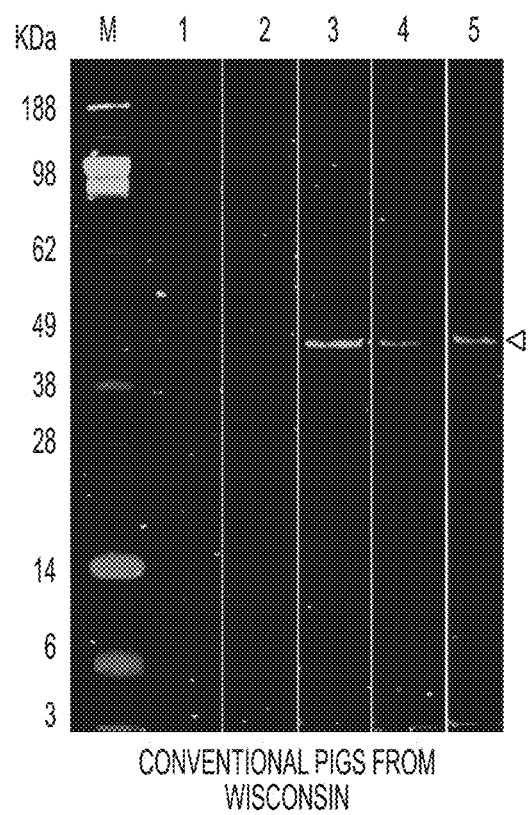
FIG. 16 shows examples of PTTV1a-ORF1-based Western blot analyses of selected porcine serum samples from a farm of Wisconsin.

According one embodiment of the present invention, the purified C-terminal PTTV1a- and PTTV1b-ORF1 proteins were used to develop genotype-specific serum Western blots and ELISA as described for PTTV2 above. FIG. 16 shows negative (lanes 1-2) and positive (lanes 3-5) examples of serum Western blot using 1a-ORF1 as antigen. The same antigen amount (69 ng), dilution of sera (1:100) and dilution of IgG conjugate (1:4000) as PTTV2-ORF1 were used in PTTV1a- and PTTV1b-specific ELISA (data not shown).

Additionally, the present invention provides a useful diagnostic reagent for detecting the porcine TTV infection which comprise a monoclonal or polyclonal antibody purified from a natural host such as, for example, by inoculating a pig with the porcine TTV or the immunogenic composition of the invention in an effective immunogenic quantity to produce a viral infection and recovering the antibody from the serum of the infected pig. Alternatively, the antibodies can be raised in experimental animals against the natural or synthetic polypeptides derived or expressed from the amino acid sequences or immunogenic fragments encoded by the nucleotide sequence of the isolated porcine TTV. For example, monoclonal antibodies can be produced from hybridoma cells which are obtained from mice such as, for example, Balb/c, immunized with a polypeptide antigen derived from the nucleotide sequence of the isolated porcine TTV. Selection of the hybridoma cells is made by growth in hyproxanthine, thymidine and aminopterin in a standard cell culture medium like Dulbecco's modified Eagle's medium (DMEM) or minimal essential medium. The hybridoma cells which produce antibodies can be cloned according to procedures known in the art. Then, the discrete colonies which are formed can be transferred into separate wells of culture plates for cultivation in a suitable culture medium. Identification of antibody secreting cells is done by conventional screening methods with the appropriate antigen or immunogen. Cultivating the hybridoma cells in vitro or in vivo by obtaining ascites fluid in mice after injecting the hybridoma produces the desired monoclonal antibody via well-known techniques.

For another alternative method, porcine TTV capsid protein can be expressed in a baculovirus expression system or E. coli expression system according to procedures known in the art. The expressed recombinant porcine TTV capsid protein can be used as the antigen for diagnosis in an enzyme-linked immunoabsorbent Assay (ELISA). The ELISA assay based on the porcine recombinant capsid antigen, for example, can be used to detect antibodies to porcine TTV in porcine and mammalian species. Although the ELISA assay is preferred, other known diagnostic tests can be employed such as immunofluorescence assay (IFA), immunoperoxidase assay (IPA), etc.

Desirably, a commercial ELISA diagnostic assay in accordance with the present invention can be used to diagnose porcine TTV infection in pigs. The examples illustrate using purified ORF1 and ORF2 proteins of porcine TTV to develop an ELISA assay to detect anti-TTV antibodies in pigs. Sera collected from pigs infected with porcine TTV, and negative sera from control pigs are used to validate the assay. PTTV2 specific, PTTV1a specific, and PTTV1b specific antibodies were demonstrated to specifically recognize PTTV ORF proteins. Further standardization of the test by techniques known to those skilled in the art may optimize the commercialization of a diagnostic assay for porcine TTV.

Another aspect of the present invention is the unique immunogenic composition comprising the isolated porcine TTV or an antigenic protein encoded by an isolated polynucleotide described hereinabove and its use for raising or producing antibodies. The composition contains a nontoxic, physiologically acceptable carrier and, optionally, one or more adjuvants. Suitable carriers, such as, for example, water, saline, ethanol, ethylene glycol, glycerol, etc., are easily selected from conventional excipients and co-formulants may be added. Routine tests can be performed to ensure physical compatibility and stability of the final composition.

In accordance with the present invention, there are further provided infectious molecular and nucleic acid molecules of porcine Torque teno (TTV), live viruses produced from the nucleic acid molecule and veterinary vaccines to protect pigs from porcine TTV viral infection or disease caused by porcine TTV co-infection with other viruses. The invention further provides immunogenic polypeptide expression products that may be used as vaccines.

The novel infectious DNA molecule of porcine TTV comprises a nucleic acid molecule encoding at least a portion of an infectious PTTV1a-VA (SEQ ID NO:9), PTTV1b-VA (SEQ ID NO:10), PTTV2c-VA (SEQ ID NO:11), or PTTV2c-VA (SEQ ID NO:12) genome. The infectious PTTV DNA clone preferably contains at least one of ORF1, ORF2, ORF1/1, and ORF2/2 gene of the PTTV1 or PTTV2. Multiple copies of the PTTV1a-VA (SEQ ID NO:9), PTTV1b-VA (SEQ ID NO:10), PTTV2c-VA (SEQ ID NO:11), or PTTV2c-VA (SEQ ID NO:12) genome may be inserted into a single DNA molecule to construct tandem infectious PTTV clones.

The cloned genomic DNA of PTTV, particularly PTTV1a-VA, PTTV1b-VA, PTTV2c-VA, and tandem PTTV2b-RR, PTTV2c-RR, described herein is shown to be in vitro or in vivo infectious when transfected into PK-15 cells and given to pigs. This new, readily reproducible pathogenic agent lends itself to the development of a suitable vaccination program to prevent PTTV infection in pigs.

Figure 17A:
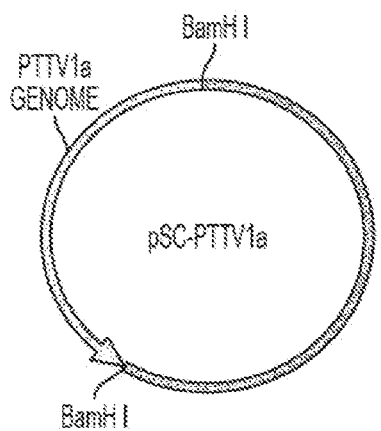
FIGS. 17A-17F represent the schematic diagrams of construction of full-length genomic DNA clones of porcine TTVs.
Figure 17B:
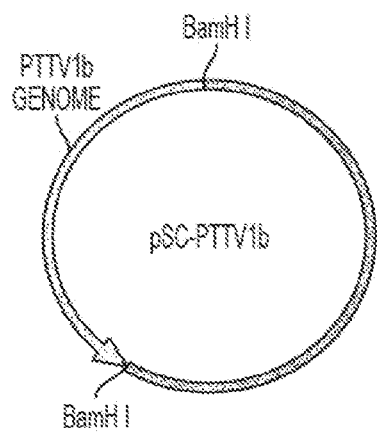
Figure 17C:
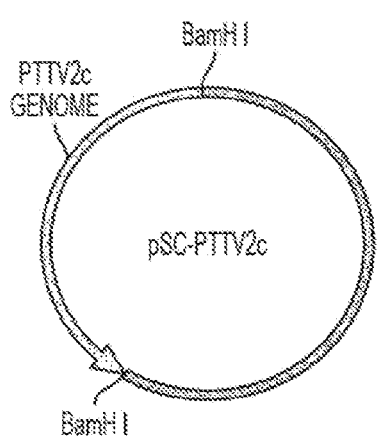

According to a further embodiment of the present invention, three one-genome-copy PTTV DNA clones were derived from the prototype US isolates PTTV1a-VA, PTTV1b-VA and PTTV2c-VA by fusion PCR, respectively. Each of the full-length genomic DNA was inserted into a cloning vector pSC-B-amp/kan by blunt-end ligation. The restriction site BamH I is the unique site on the three PTTV genomes, which was engineered at both ends of the three genomes to facilitate the generation of concatemers and thus mimic the TTV circular genome. BamH I single digestions of the selected plasmid DNA of each clone clearly resulted in two different fragments of 4.3-Kb and 2.8-Kb in size (FIG. 18A). The 4.3-Kb fragments represented the backbone vector whereas the 2.8-Kb fragments represented the inserted PTTV genomic DNA. The empty vector pSC-B-amp/kan digested with the same enzyme only showed a 4.3-Kb band (FIG. 18A). The resulting PTTV clones were designated pSC-PTTV1a, pSC-PTTV1b and pSC-PTTV2c, respectively (FIG. 17A-C).

Figure 17D:
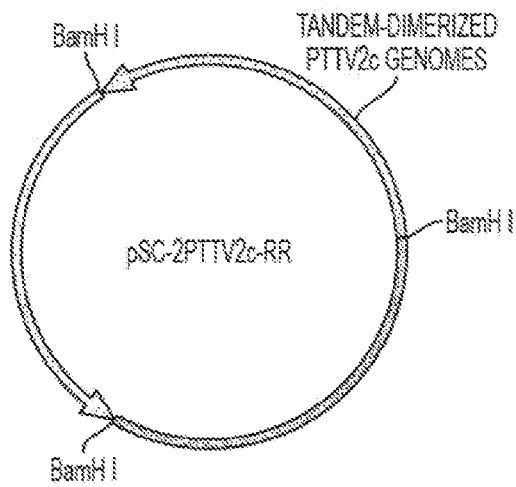
Figure 17E:
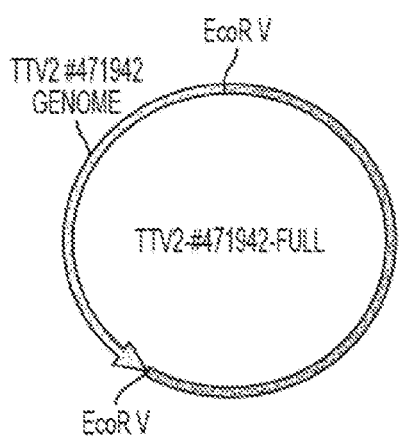
Figure 17F:
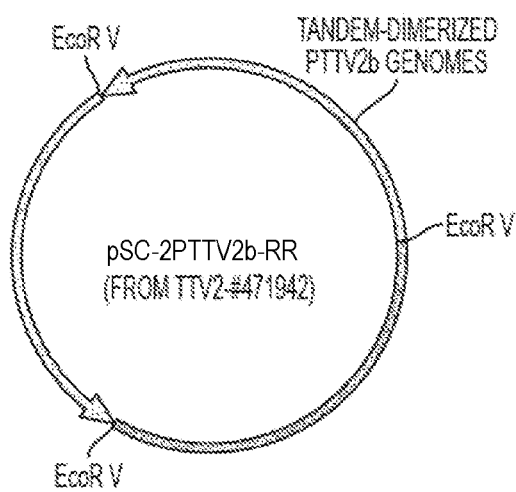

Furthermore, two copies of the full-length PTTV2c-VA genome derived from the clone pSC-PTTV2c were ligated in tandem into the pSC-B-amp/kan vector to generate the clone pSC-2PTTV2c-RR (FIG. 17D). Comparison of the Afl II single digestion patterns between pSC-PTTV2c and pSC-2PTTV2c-RR showed that the latter plasmid had an additional 2.8-Kb fragment representing the second copy of PTTV2c genome (FIG. 18B, right panel). Subsequently, we utilized the same cloning strategy to produce a tandem-dimerized PTTV2b DNA clone derived from the Germany TTV clone TTV2-#471942-full. An additional 2.8-Kb fragment representing the second copy of PTTV2b genome was presented in this construct, designated pSC-2PTTV2b-RR (FIG. 17F), which was digested with the Hind III alone when compared to its one-genome-copy counterpart (FIG. 18B, left panel), confirming the successful construction.

Figures 19A, 19B:
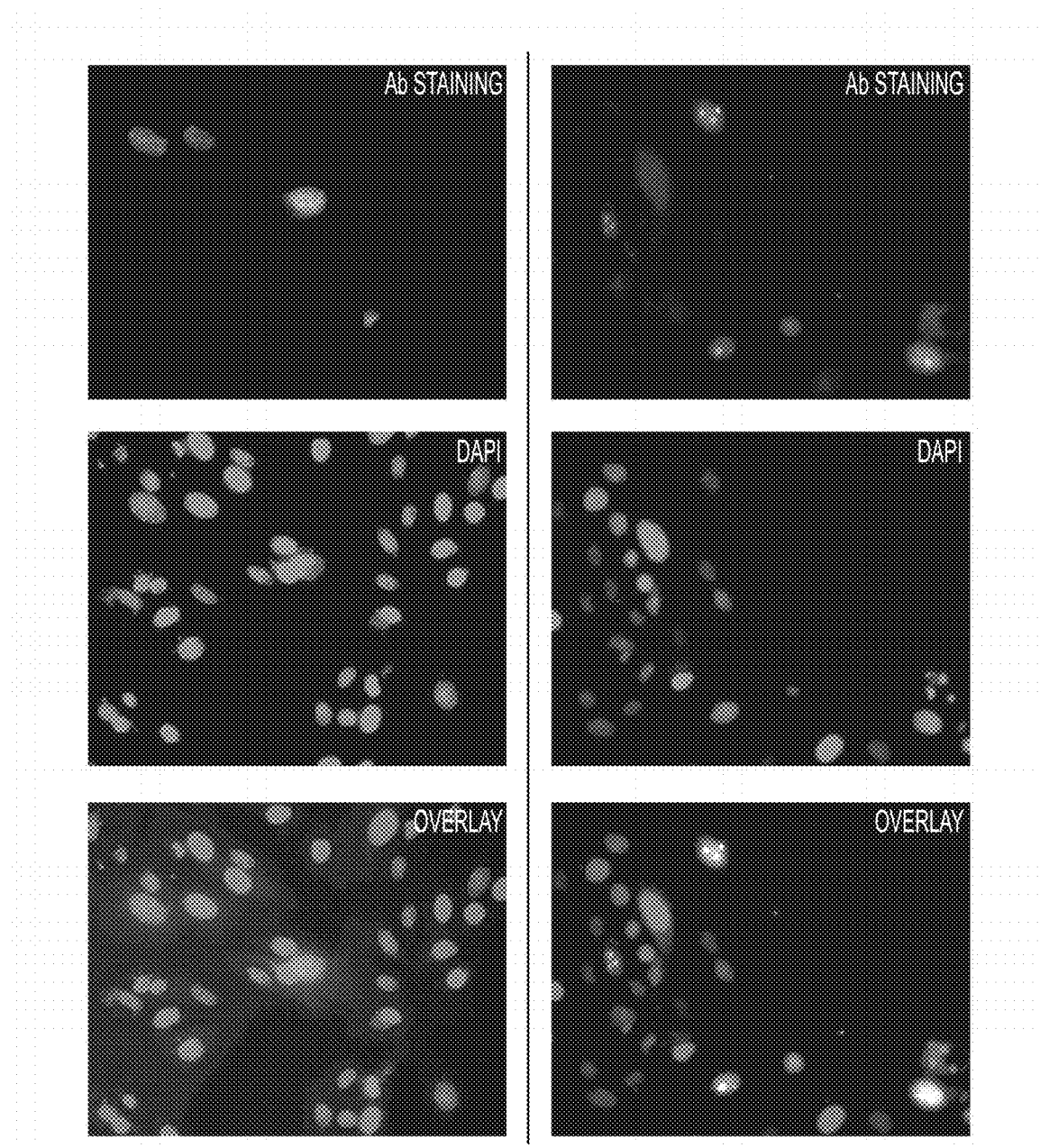
FIGS. 19A and 19B represent the immunofluorescence assay (IFA) results of transfection (19A) or transfected cell passaging (19B) of the concatemerized TTV2-#471942-full DNA in PK-15 cells using a PTTV2-specific anti-ORF1 polyclonal antibody (Ab).
Figure 21:
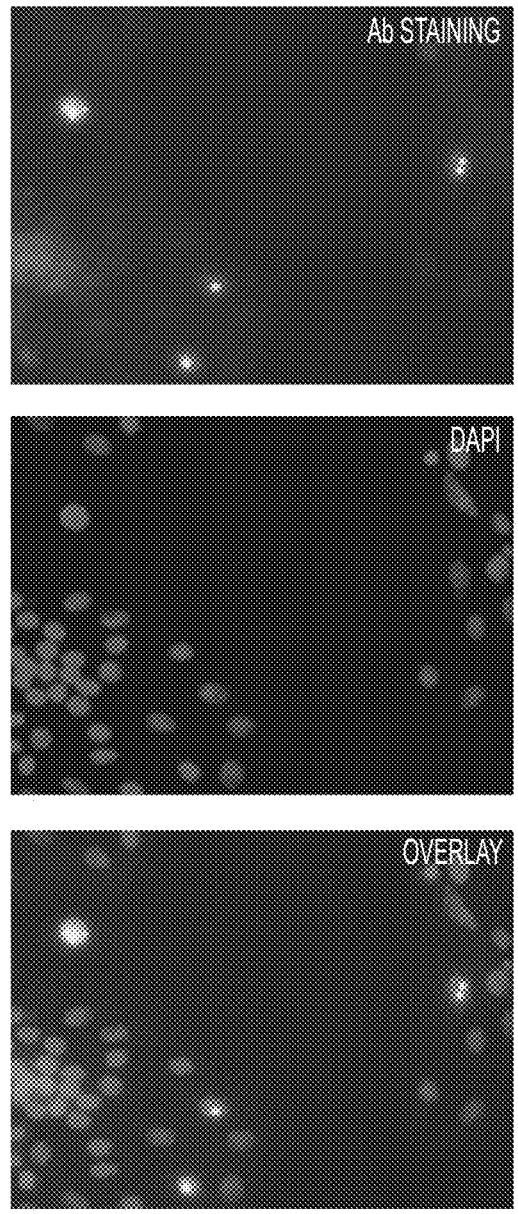
FIG. 21 represents the IFA results of transfection of the concatemerized PTTV1a DNA in PK-15 cells at 3 days post-transfection using a PTTV1a-specific anti-ORF1 Ab. Magnification=200×. DAPI was used to stain the cell nucleus.

The replication competencies of the constructed PTTV infectious clones were tested by in vitro transfection of PK-15 cells. IFA using the commercially generated rabbit polyclonal antibodies against PTTV2c ORF1 confirmed that both the concatemers of clones TTV2-#471942-full and pSC-PTTV2c were replication competent, respectively (FIG. 19A and FIG. 20A). Passaging of the transfected cells did not eliminate or reduce the fluorescent signals (FIG. 19B and FIG. 20B), suggesting that the expression of ORF1 proteins was resulted from the PTTV2 concatemers that mimicked the natural PTTV2b or PTTV2c circular molecules. No fluorescent signals was observed in mock-transfected cells or DNA-transfected cells using pre-immune rabbit serum as the antibody for IFA detection (data not shown). The concatemers of the clone pSC-PTTV1a also showed to be replication-competent using an anti-PTTV1a ORF1 antibody (FIG. 21). The positive fluorescent signals were located in the nucleus of transfected or passaged cells, indicating that porcine TTVs likely replicate in the cell nucleus. It is not unexpected because porcine circovirus (PCV) has a similar expression pattern in vitro.

Figure 22A:
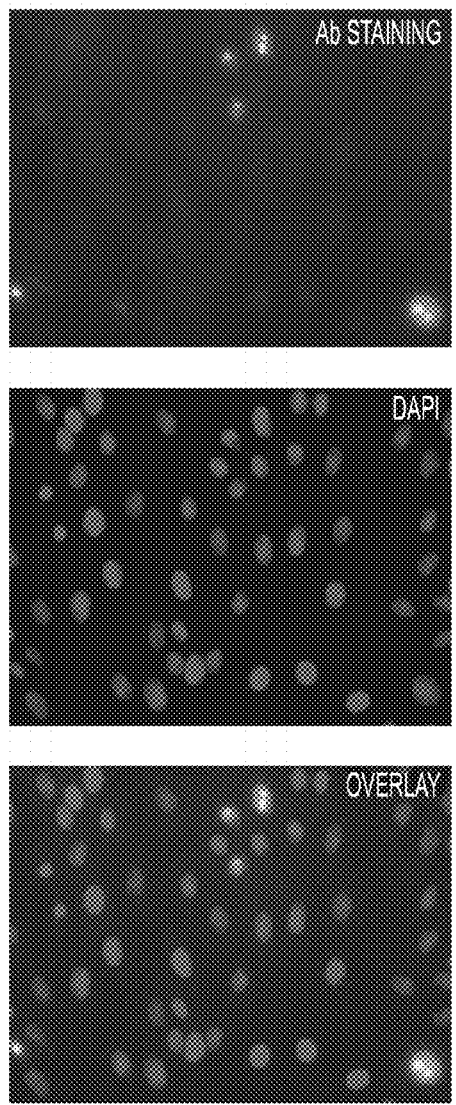
FIGS. 22A and 22B represent the IFA results of transfection of the pSC-2PTTV2b-RR plasmid (FIG. 22A) or pSC-2PTTV2c-RR plasmid (FIG. 22B) in PK-15 cells at 3 days post-transfection. Magnification=200×. DAPI was used to stain the cell nucleus.
Figure 22B:
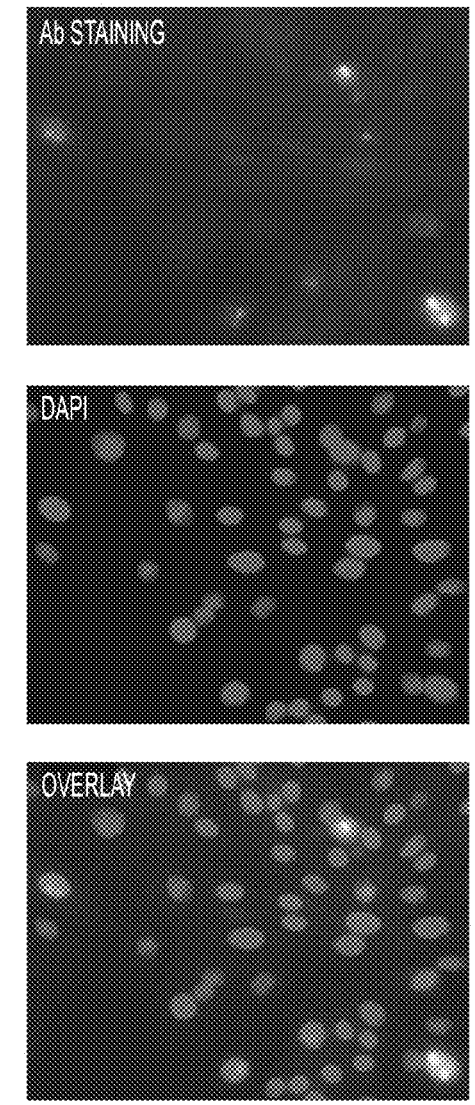
Figure 23A:
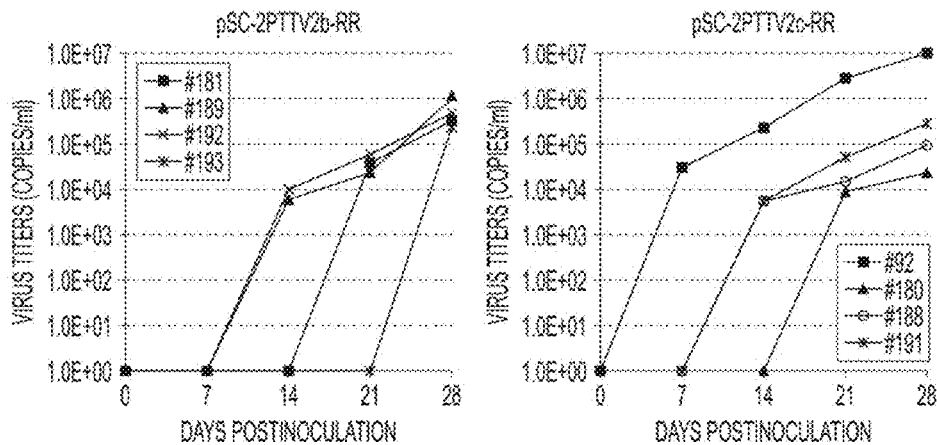
FIGS. 23A and 23B represent the determination of the in vivo infectivity of the two porcine TTV2 DNA clones, pSC-2PTTV2b-RR and pSC-2PTTV2c-RR, in conventional pigs, respectively.
Figure 23B:
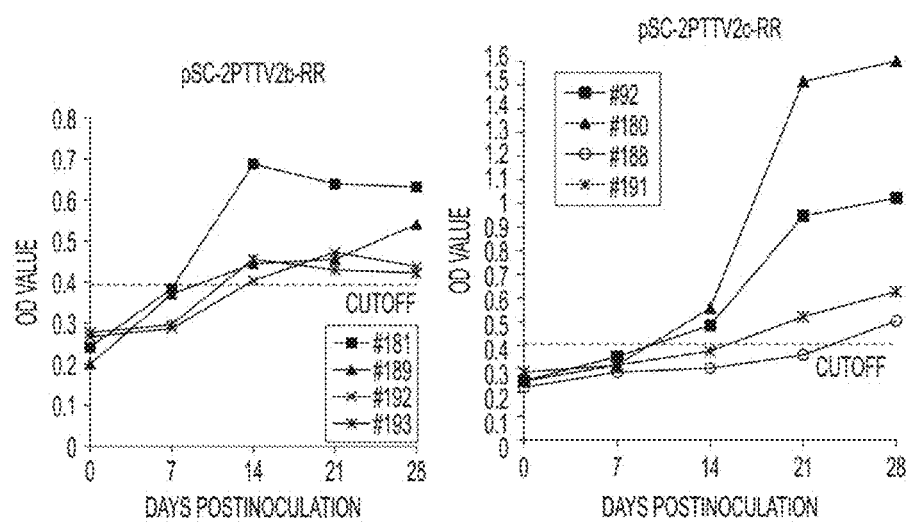

Direct transfection of the tandem-dimerized clone pSC-2PTTV2b-RR or pSC-2PTTV2c-RR in PK-15 cells results in viral replication and produces the ORF1 capsid antigen. IFA using antibodies against PTTV2 ORF1 confirmed that both clones were also replication-competent and the positive ORF1 antigens were localized in the nuclei (FIGS. 22A and B).

According to one embodiment of the present invention, infectious clones of porcine TTV can be used to inoculate pigs, which will then ellicit an immune response of the host animal and stimulate production of neutralizing antibodies. In one particular embodiment of the present invention, the two tandem-dimerized PTTV2 clones were infectious when injected into the lymph nodes and muscles of conventional pigs.

To test the in vivo infectivity of PTTV2 molecular clones, conventional pigs were inoculated with the clone pSC-2TTV2b-RR or pSC-2TTV2c-RR. Serum samples were collected from animals at 0, 7, 14, 21 and 28 days post-inoculation (DPI). PTTV2 DNA was detected in pSC-2TTV2c-RR-inoculated pigs beginning at 7 DPI (#92), 14 DPI (#188 and #191) and 21 DPI (#180), respectively (FIG. 23A, right panel). PTTV viremia appeared late for pigs inoculated with the clone pSC-2TTV2b-RR: two began at 14 DPI (#189 and #192), one at 21 DPI (#181) and one at 28 DPI (#193) (FIG. 23A, left panel). The viral loads increased during the course in all inoculated pigs that had the highest viral loads at 28 DPI before necropsy, as determined by PTTV2-specific real-time PCR (FIG. 23A). The real-time PCR products amplified from selected pigs were sequenced and found to have identical sequences to the corresponding regions of pSC-2TTV2b-RR or pSC-2TTV2c-RR (data not shown).

All inoculated pigs were negative for PTTV2 ORF1 antibodies at 0 and 7 DPI. At 14 DPI, all the four pSC-2TTV2b-RR-inoculated pigs seroconverted to anti-PTTV2 ORF1 IgG, whereas pigs in pSC-2TTV2c-RR-inoculated group seroconverted at 14 (#92 and #180), 21 (#191) and 28 (#188) DPI, respectively (FIG. 23B). The results indicated that active porcine TTV2b or TTV2c infection had occurred.

Vaccines of the infectious viral and infectious molecular DNA clones, and methods of using them, are also included within the scope of the present invention. Inoculated pigs are protected from viral infection and associated diseases caused by TTV2 infection or co-infection. The novel method protects pigs in need of protection against viral infection by administering to the pig an immunologically effective amount of a vaccine according to the invention, such as, for example, a vaccine comprising an immunogenic amount of the infectious PTTV DNA, a plasmid or viral vector containing the infectious DNA clone of PTTV, the recombinant PTTV DNA, the polypeptide expression products, the bacteria-expressed or baculovirus-expressed purified recombinant ORF1 capsid protein, etc. Other antigens such as PRRSV, PPV, other infectious swine agents and immune stimulants may be given concurrently to the pig to provide a broad spectrum of protection against viral infections.

The vaccines comprise, for example, the infectious viral and molecular DNA clones, the cloned PTTV infectious DNA genome in suitable plasmids or vectors such as, for example, the pSC-B vector, an avirulent, live virus, an inactivated virus, expressed recombinant capsid subunit vaccine, etc. in combination with a nontoxic, physiologically acceptable carrier and, optionally, one or more adjuvants. The vaccine may also comprise the infectious TTV2 molecular DNA clone described herein. The infectious PTTV DNA, the plasmid DNA containing the infectious viral genome and the live virus are preferred with the live virus being most preferred. The avirulent, live viral vaccine of the present invention provides an advantage over traditional viral vaccines that use either attenuated, live viruses which run the risk of reverting back to the virulent state or killed cell culture propagated whole virus which may not induce sufficient antibody immune response for protection against the viral disease.

Vaccines and methods of using them are also included within the scope of the present invention. Inoculated mammalian species are protected from serious viral infection, may also provide protection for disease related to co-infection of PTTV, such as porcine dermatitis and nephropathy syndrome (PDNS), postweaning multisystemic wasting syndrome (PMWS), and other related illness. The vaccines comprise, for example, an inactivated or attenuated porcine TTV virus, a nontoxic, physiologically acceptable carrier and, optionally, one or more adjuvants.

The adjuvant, which may be administered in conjunction with the vaccine of the present invention, is a substance that increases the immunological response of the pig to the vaccine. The adjuvant may be administered at the same time and at the same site as the vaccine, or at a different time, for example, as a booster. Adjuvants also may advantageously be administered to the pig in a manner or at a site different from the manner or site in which the vaccine is administered. Suitable adjuvants include, but are not limited to, aluminum hydroxide (alum), immunostimulating complexes (ISCOMS), non-ionic block polymers or copolymers, cytokines (like IL-1, IL-2, IL-7, IFN-α, IFN-γ, etc.), saponins, monophosphoryl lipid A (MLA), muramyl dipeptides (MDP) and the like. Other suitable adjuvants include, for example, aluminum potassium sulfate, heat-labile or heat-stable enterotoxin isolated from *Escherichia coli*, cholera toxin or the B subunit thereof, diphtheria toxin, tetanus toxin, pertussis toxin, Freund's incomplete or complete adjuvant, etc. Toxin-based adjuvants, such as diphtheria toxin, tetanus toxin and pertussis toxin may be inactivated prior to use, for example, by treatment with formaldehyde.

The vaccines may further contain additional antigens to promote the immunological activity of the infectious PTTV DNA clones such as, for example, porcine reproductive and respiratory syndrome virus (PRRSV), porcine parvovirus (PPV), other infectious swine agents and immune stimulants.

The new vaccines of this invention are not restricted to any particular type or method of preparation. The cloned viral vaccines include, but are not limited to, infectious DNA vaccines (i.e., using plasmids, vectors or other conventional carriers to directly inject DNA into pigs), live vaccines, modified live vaccines, inactivated vaccines, subunit vaccines, attenuated vaccines, genetically engineered vaccines, etc. These vaccines are prepared by standard methods known in the art.

As a further benefit, the preferred live virus of the present invention provides a genetically stable vaccine that is easier to make, store and deliver than other types of attenuated vaccines.

Another preferred vaccine of the present invention utilizes suitable plasmids for delivering the nonpathogenic DNA clone to pigs. In contrast to the traditional vaccine that uses live or killed cell culture propagated whole virus, this invention provides for the direct inoculation of pigs with the plasmid DNA containing the infectious viral genome.

Additional genetically engineered vaccines, which are desirable in the present invention, are produced by techniques known in the art. Such techniques involve, but are not limited to, further manipulation of recombinant DNA, modification of or substitutions to the amino acid sequences of the recombinant proteins and the like.

Genetically engineered vaccines based on recombinant DNA technology are made, for instance, by identifying alternative portions of the viral gene encoding proteins responsible for inducing a stronger immune or protective response in pigs (e.g., proteins derived from ORF1, ORF1/1, ORF2, ORF2/2, etc.). Such identified genes or immunodominant fragments can be cloned into standard protein expression vectors, such as the baculovirus vector, and used to infect appropriate host cells (see, for example, O'Reilly et al., "Baculovirus Expression Vectors: A Lab Manual," Freeman & Co., 1992). The host cells are cultured, thus expressing the desired vaccine proteins, which can be purified to the desired extent and formulated into a suitable vaccine product. The recombinant subunit vaccines are based on bacteria-expressed (FIG. 10, FIG. 15) or baculovirus-expressed ORF1 capsid proteins of PTTV1a, PTTV1b and PTTV2.

If the clones retain any undesirable natural abilities of causing disease, it is also possible to pinpoint the nucleotide sequences in the viral genome responsible for any residual virulence, and genetically engineer the virus avirulent through, for example, site-directed mutagenesis. Site-directed mutagenesis is able to add, delete or change one or more nucleotides (see, for instance, Zoller et al., DNA 3:479-488, 1984). An oligonucleotide is synthesized containing the desired mutation and annealed to a portion of single stranded viral DNA. The hybrid molecule, which results from that procedure, is employed to transform bacteria. Then double-stranded DNA, which is isolated containing the appropriate mutation, is used to produce full-length DNA by ligation to a restriction fragment of the latter that is subsequently transfected into a suitable cell culture. Ligation of the genome into the suitable vector for transfer may be accomplished through any standard technique known to those of ordinary skill in the art. Transfection of the vector into host cells for the production of viral progeny may be done using any of the conventional methods such as calcium-phosphate or DEAE-dextran mediated transfection, electroporation, protoplast fusion and other well-known techniques (e.g., Sambrook et al., "Molecular Cloning: A Laboratory Manual," Cold Spring Harbor Laboratory Press, 1989). The cloned virus then exhibits the desired mutation. Alternatively, two oligonucleotides can be synthesized which contain the appropriate mutation. These may be annealed to form double-stranded DNA that can be inserted in the viral DNA to produce full-length DNA.

An immunologically effective amount of the vaccines of the present invention is administered to a pig in need of protection against viral infection. The immunologically effective amount or the immunogenic amount that inoculates the pig can be easily determined or readily titrated by routine testing. An effective amount is one in which a sufficient immunological response to the vaccine is attained to protect the pig exposed to the PTTV virus. Preferably, the pig is protected to an extent in which one to all of the adverse physiological symptoms or effects of the viral disease are significantly reduced, ameliorated or totally prevented.

The vaccine can be administered in a single dose or in repeated doses. Dosages may range, for example, from about 1 microgram to about 1,000 micrograms of the plasmid DNA containing the infectious chimeric DNA genome (dependent upon the concentration of the immuno-active component of the vaccine), preferably 100 to 200 micrograms of the porcine TTV DNA clone, but should not contain an amount of virus-based antigen sufficient to result in an adverse reaction or physiological symptoms of viral infection. Methods are known in the art for determining or titrating suitable dosages of active antigenic agent to find minimal effective dosages based on the weight of the pig, concentration of the antigen and other typical factors. Preferably, the infectious viral DNA clone is used as a vaccine, or a live infectious virus can be generated in vitro and then the live virus is used as a vaccine. In that case, from about 50 to about 10,000 of the 50% tissue culture infective dose (TCID 50) of live virus, for example, can be given to a pig.

The new vaccines of this invention are not restricted to any particular type or method of preparation. The vaccines include, but are not limited to, modified live vaccines, inactivated vaccines, subunit vaccines, attenuated vaccines, genetically engineered vaccines, etc.

The advantages of live vaccines are that all possible immune responses are activated in the recipient of the vaccine, including systemic, local, humoral and cell-mediated immune responses. The disadvantages of live virus vaccines, which may outweigh the advantages, lie in the potential for contamination with live adventitious viral agents or the risk that the virus may revert to virulence in the field.

To prepare inactivated virus vaccines, for instance, the virus propagation and virus production can occur in cultured porcine cell lines such as, without limitation PK-15 cells. Serial virus inactivation is then optimized by protocols generally known to those of ordinary skill in the art or, preferably, by the methods described herein.

Inactivated virus vaccines may be prepared by treating the porcine TTV with inactivating agents such as formalin or hydrophobic solvents, acids, etc., by irradiation with ultraviolet light or X-rays, by heating, etc. Inactivation is conducted in a manner understood in the art. For example, in chemical inactivation, a suitable virus sample or serum sample containing the virus is treated for a sufficient length of time with a sufficient amount or concentration of inactivating agent at a sufficiently high (or low, depending on the inactivating agent) temperature or pH to inactivate the virus. Inactivation by heating is conducted at a temperature and for a length of time sufficient to inactivate the virus. Inactivation by irradiation is conducted using a wavelength of light or other energy source for a length of time sufficient to inactivate the virus. The virus is considered inactivated if it is unable to infect a cell susceptible to infection.

The preparation of subunit vaccines typically differs from the preparation of a modified live vaccine or an inactivated vaccine. Prior to preparation of a subunit vaccine, the protective or antigenic components of the vaccine must be identified. In the present invention, antigenic components of PTTV were identified as the ORF1 capsid proteins of PTTV1a, PTTV1b and PTTV2, which were expressed and purified in Escherichia coli (E. coli) in this invention, and other expression system, such as baculovirus expression system, for use as subunit recombinant capsid vaccines. Such protective or antigenic components include certain amino acid segments or fragments of the viral capsid proteins which raise a particularly strong protective or immunological response in pigs; single or multiple viral capsid proteins themselves, oligomers thereof, and higher-order associations of the viral capsid proteins which form virus substructures or identifiable parts or units of such substructures; oligoglycosides, glycolipids or glycoproteins present on or near the surface of the virus or in viral substructures such as the lipoproteins or lipid groups associated with the virus, etc. Preferably, the ORF1 protein is employed as the antigenic component of the subunit vaccine. Other proteins may also be used such as those encoded by the nucleotide sequence in the ORF2, ORF1/1, and ORF2/2 gene. These immunogenic components are readily identified by methods known in the art. Once identified, the protective or antigenic portions of the virus (i.e., the "subunit") are subsequently purified and/or cloned by procedures known in the art. The subunit vaccine provides an advantage over other vaccines based on the live virus since the subunit, such as highly purified subunits of the virus, is less toxic than the whole virus.

If the subunit vaccine is produced through recombinant genetic techniques, expression of the cloned subunit such as the ORF1, ORF2. ORF1/1, and ORF2/2 genes, for example, may be expressed by the method provided above, and may also be optimized by methods known to those in the art (see, for example, Maniatis et al., "Molecular Cloning: A Laboratory Manual," Cold Spring Harbor Laboratory, Cold Spring Harbor, Mass. (1989)). On the other hand, if the subunit being employed represents an intact structural feature of the virus, such as an entire capsid protein, the procedure for its isolation from the virus must then be optimized. In either case, after optimization of the inactivation protocol, the subunit purification protocol may be optimized prior to manufacture.

To prepare attenuated vaccines, the live, pathogenic virus is first attenuated (rendered nonpathogenic or harmless) by methods known in the art or, preferably, as described herein. For instance, attenuated viruses may be prepared by the technique of the present invention which involves the novel serial passage through embryonated pig eggs. Attenuated viruses can be found in nature and may have naturally-occurring gene deletions or, alternatively, the pathogenic viruses can be attenuated by making gene deletions or producing gene mutations. The attenuated and inactivated virus vaccines comprise the preferred vaccines of the present invention.

Genetically engineered vaccines, which are also desirable in the present invention, are produced by techniques known in the art. Such techniques involve, but are not limited to, the use of RNA, recombinant DNA, recombinant proteins, live viruses and the like.

For instance, after purification, the wild-type virus may be isolated from suitable clinical, biological samples such as serum, fecal, saliva, semen and tissue samples by methods known in the art, preferably by the method taught herein using infected pigs or infected suitable cell lines. The DNA is extracted from the biologically pure virus or infectious agent by methods known in the art, and purified by methods known in the art, preferably by ultracentrifugation in a CsCl gradient. The cDNA of viral genome is cloned into a suitable host by methods known in the art (see Maniatis et al., id.), and the virus genome is then analyzed to determine essential regions of the genome for producing antigenic portions of the virus. Thereafter, the procedure is generally the same as that for the modified live vaccine, an inactivated vaccine or a subunit vaccine.

Genetically engineered vaccines based on recombinant DNA technology are made, for instance, by identifying the portion of the viral gene which encodes for proteins responsible for inducing a stronger immune or protective response in pigs (e.g., proteins derived from ORF1, ORF2, ORF1/1, and ORF2/2, etc.). Such identified genes or immuno-dominant fragments can be cloned into standard protein expression vectors, such as the baculovirus vector, and used to infect appropriate host cells (see, for example, O'Reilly et al., "Baculovirus Expression Vectors: A Lab Manual," Freeman & Co. (1992)). The host cells are cultured, thus expressing the desired vaccine proteins, which can be purified to the desired extent and formulated into a suitable vaccine product.

Genetically engineered proteins, useful in vaccines, for instance, may be expressed in insect cells, yeast cells or mammalian cells. The genetically engineered proteins, which may be purified or isolated by conventional methods, can be directly inoculated into a porcine or mammalian species to confer protection against porcine TTV.

An insect cell line (like sf9, sf21, or HIGH-FIVE) can be transformed with a transfer vector containing polynucleic acids obtained from the virus or copied from the viral genome which encodes one or more of the immuno-dominant proteins of the virus. The transfer vector includes, for example, linearized baculovirus DNA and a plasmid containing the desired polynucleotides. The host cell line may be co-transfected with the linearized baculovirus DNA and a plasmid in order to make a recombinant baculovirus.

Alternatively, DNA from the isolated porcine TTV which encode one or more capsid proteins can be inserted into live vectors, such as a poxvirus or an adenovirus and used as a vaccine.

An immunologically effective amount of the vaccine of the present invention is administered to a porcine or mammalian species in need of protection against said infection or syndrome. The "immunologically effective amount" can be easily determined or readily titrated by routine testing. An effective amount is one in which a sufficient immunological response to the vaccine is attained to protect the pig or other mammal exposed to the porcine TTV virus, or porcine TTV co-infection, which may cause porcine dermatitis and nephropathy syndrome (PDNS), postweaning multisystemic wasting syndrome (PMWS) or related illness. Preferably, the pig or other mammalian species is protected to an extent in which one to all of the adverse physiological symptoms or effects of the viral disease are found to be significantly reduced, ameliorated or totally prevented.

The vaccine can be administered in a single dose or in repeated doses. Dosages may contain, for example, from 1 to 1,000 micrograms of virus-based antigen (dependent upon the concentration of the immuno-active component of the vaccine), but should not contain an amount of virus-based antigen sufficient to result in an adverse reaction or physiological symptoms of viral infection. Methods are known in the art for determining or titrating suitable dosages of active antigenic agent based on the weight of the bird or mammal, concentration of the antigen and other typical factors.

The vaccine can be administered to pigs. Also, the vaccine can be given to humans such as pig farmers who are at high risk of being infected by the viral agent. It is contemplated that a vaccine based on the porcine TTV can be designed to provide broad protection against both porcine and human TTV. In other words, the vaccine based on the porcine TTV can be preferentially designed to protect against human TTV infection through the so-called "Jennerian approach" (i.e., cowpox virus vaccine can be used against human smallpox by Edward Jenner). Desirably, the vaccine is administered directly to a porcine or other mammalian species not yet exposed to the TTV virus. The vaccine can conveniently be administered orally, intrabuccally, intranasally, transdermally, parenterally, etc. The parenteral route of administration includes, but is not limited to, intramuscular, intravenous, intraperitoneal and subcutaneous routes.

When administered as a liquid, the present vaccine may be prepared in the form of an aqueous solution, a syrup, an elixir, a tincture and the like. Such formulations are known in the art and are typically prepared by dissolution of the antigen and other typical additives in the appropriate carrier or solvent systems. Suitable carriers or solvents include, but are not limited to, water, saline, ethanol, ethylene glycol, glycerol, etc. Typical additives are, for example, certified dyes, flavors, sweeteners and antimicrobial preservatives such as thimerosal (sodium ethylmercurithiosalicylate). Such solutions may be stabilized, for example, by addition of partially hydrolyzed gelatin, sorbitol or cell culture medium, and may be buffered by conventional methods using reagents known in the art, such as sodium hydrogen phosphate, sodium dihydrogen phosphate, potassium hydrogen phosphate, potassium dihydrogen phosphate, a mixture thereof, and the like.

Liquid formulations also may include suspensions and emulsions which contain suspending or emulsifying agents in combination with other standard co-formulants. These types of liquid formulations may be prepared by conventional methods. Suspensions, for example, may be prepared using a colloid mill. Emulsions, for example, may be prepared using a homogenizer.

Parenteral formulations, designed for injection into body fluid systems, require proper isotonicity and pH buffering to the corresponding levels of mammalian body fluids. Isotonicity can be appropriately adjusted with sodium chloride and other salts as needed. Suitable solvents, such as ethanol or propylene glycol, can be used to increase the solubility of the ingredients in the formulation and the stability of the liquid preparation. Further additives which can be employed in the present vaccine include, but are not limited to, dextrose, conventional antioxidants and conventional chelating agents such as ethylenediamine tetraacetic acid (EDTA). Parenteral dosage forms must also be sterilized prior to use.

The following examples demonstrate certain aspects of the present invention. However, it is to be understood that these examples are for illustration only and do not purport to be wholly definitive as to conditions and scope of this invention. It should be appreciated that when typical reaction conditions (e.g., temperature, reaction times, etc.) have been given, the conditions both above and below the specified ranges can also be used, though generally less conveniently. The examples are conducted at room temperature (about 23° C. to about 28° C.) and at atmospheric pressure. All parts and percents referred to herein are on a weight basis and all temperatures are expressed in degrees centigrade unless otherwise specified.

Example 1

Viral DNA Extraction, Nested PCR and Genomic PCR

Convenient serum and semen samples from 20 conventional adult boars from a Virginia pig farm were used in the study. Total DNA was isolated from 20 serum and 19 semen samples using QIAamp DNA mini kit (Qiagen). To screen for the positive PTTV-containing samples, nested PCR amplifications of the conserved regions in the UTR of PTTV1 and PTTV2 were initially performed by using AmpliTag Gold polymerase (Applied Biosystems). The two primer pairs used to amplify the fragment A of PTTV1 were TTV1-mF (SEQ ID NO:45)/TTV1-mR (SEQ ID NO:46)(for the first-round PCR) and TTV1-nF (SEQ ID NO:47)/TTV1-nR (SEQ ID NO:48) (for the second-round PCR), whereas the two primer pairs used to amplify the fragment D of PTTV2 were TTV2-mF (SEQ ID NO:49)/TTV2-mR (SEQ ID NO:50) (for the first-round PCR) and TTV2-nF (SEQ ID NO:51)/TTV2-nR (SEQ ID NO:52) (for the second-round PCR; FIGS. 1A-1B and Table 1).

In order to amplify the full-length genomic sequences of both PTTV1 and PTTV2, we first performed an inverse genomic PCR using a pair of conserved gene-specific primers TTV1-IF (SEQ ID NO:1)/TTV1-IR (SEQ ID NO:4) located in region A for PTTV1 and another pair of gene-specific primers TTV2-IF (SEQ ID NO:5)/TTV2-IR (SEQ ID NO:8) located in region D for PTTV2, respectively, with Herculase II Fusion DNA Polymerase (Stratagene) according to the manufacturer's instructions. No PCR products with expected sizes were detected. Subsequently we designed new sets of primers to amplify two regions covering the complete PTTV1 and PTTV2 genomes in the second-round PCR, respectively (FIG. 1A-1B). The primer pairs used to amplify fragments B and C of PTTV1 were TTV1-IF (SEQ ID NO:1)/TTV1-2340R (SEQ ID NO:2) and TTV1-2311F (SEQ ID NO:3)/TTV1-IR (SEQ ID NO:4), respectively, whereas the primer pairs used to amplify fragments E and F of PTTV2 were TTV2-IF (SEQ ID NO:5)/TTV2-2316R (SEQ ID NO:6) and TTV2-GCF (SEQ ID NO:7)/TTV2-IR (SEQ ID NO:8), respectively (FIGS. 1A-1B and Table 1). Fragments C and F contain the GC-rich regions of PTTV1 and PTTV2, respectively. The amplified PCR products were individually excised, purified, and subsequently cloned into a pSC-B-amp/kan vector (Stratagene) by StrataClone Blunt PCR cloning strategy according to the manufacturer's instructions (Stratagene) followed by DNA sequencing.

Example 2

Screening for Porcine TTV Positive Samples Collected from Boars in a Farm from Virginia Porcine TTV DNA was previously detected from pigs in different geographic regions by nested-PCR based on the UTR sequence of a Japanese PTTV1 strain Sd-TTV31 (McKeown et al., 2004, supra). With the recent identification of PTTV2, two different sets of nested-PCR primers have been used to amplify region A of PTTV1 and region D of PTTV2, respectively (FIG. 1A-1B) (Ellis et al., 2008, supra; Kekarainen, T., Sibila, M., and Segales, J. (2006). Prevalence of swine Torque teno virus in post-weaning multisystemic wasting syndrome (PMWS)-affected and non-PMWS-affected pigs in Spain. *J Gen Virol* 87(Pt 4), 833-7; Krakowka et al., 2008, supra). A similar detection approach was also utilized in the present study to identify PTTV strains from pigs in the United States. In order to screen for indigenous PTTV1- or PTTV2-positive samples for subsequent use to determine the full-length genomic sequences, 20 sera (SR#1-20) and 19 semen samples (SM#1-18, and SM#20) collected from 20 boars in a farm of Virginia were subjected to nested-PCR analyses. Surprisingly, all the 20 serum samples were positive for PTTV1 and 19 were also positive for PTTV2 (except for SR#18). In contrast, only 1 semen sample (SM#6) was PTTV1-positive and 3 semen samples (SM#8, 9 and 20) were PTTV2-positive. The result was consistent with a recent study in that boar semen samples were shown to be positive for PTTV DNA in Spain (Kekarainen, T., Lopez-Soria, S., and Segales, J. (2007). Detection of swine Torque teno virus genogroups 1 and 2 in boar sera and semen. *Theriogenology* 68(7), 966-71), and thus suggesting a potential vertical transmission of PTTV. However, the prevalence rates of both PTTV1 and PTTV2 in semen were much lower than that in sera, suggesting that there is no direct association for the presence of PTTV DNAs in sera and semen of the same pig.

Example 3

Sequence and Phylogenetic Analyses

Generic analyses and alignment of DNA and amino acid sequences were performed using Lasergene package (DNASTAR Inc., Madison, Wis.). The genomic sequences of three known PTTV strains and their corresponding GenBank accession numbers used for the alignment and comparison are Sd-TTV31 (AB076001), TTV-1p (AY823990) and TTV-2p (AY823991). Pairwise sequence comparisons (PASC) were performed using 121 full-length genomic sequences of human and animal TTV-related strains available in GenBank with an online program PASC (Pairwise Sequence Comparison) developed for analysis of pairwise identity distribution within viral families and available from the National Center for Biotechnology Information (NCBI) (Bao Y., Kapustin Y. & Tatusova T. (2008). Virus Classification by Pairwise Sequence Comparison (PASC). Encyclopedia of Virology, 5 vols. (B.W.J. Mahy and M.H.V. Van Regenmortel, Editors). Oxford: Elsevier. Vol. 5, 342-348)

Phylogenetic trees were constructed by the neighbor-joining method in the PAUP 4.0 program (David Swofford, Smithsonian Institute, Washington, D.C., distributed by Sinauer Associate Inc.) based upon the full-length genomic sequences and the deduced amino acid sequences of 4 ORFs of seven PTTV strains. The data were obtained from 1000 re-sampling.

Example 4

Design of PCR Primers for Diagnosing Porcine PTTV Infection

Analyses and alignment of DNA sequences were performed using Lasergene package (DNASTAR Inc., Madison, Wis.). Full-length genomic sequences of ten porcine TTV strains and their corresponding GenBank accession numbers used for the alignment were as follows. Species PTTV1: Sd-TTV31 (AB076001), PTTV1a-VA (GU456383), TTV-1p (AY823990), PTTV1b-VA (GU456384), swSTHY-TT27 (GQ120664) and TTV1 #471819 (GU188045). Species PTTV2: PTTV2b-VA (GU456385), PTTV2c-VA (GU456386), TTV-2p (AY823991) and TTV2 #472142 (GU188046). The conserved sequences among the 6 PTTV1 and 4 PTTV2 genomes were identified, respectively, and subsequently used to guide real-time PCR primer selections using the Beacon Designer program (PREMIER Biosoft International, Palo Alto, Calif.). Primers used for the duplex nested PCR of PTTV1 were designed by the Lasergene package.

Example 5

Standard Curves of PTTV1 and PTTV2 Real-Time PCR

A region of 2091 by corresponding to the PCR fragment B of PTTV1b-VA genome was re-amplified from the same PCR fragment using primers TTV1-1F (5'-CATAGGGTG-TAACCAATCAGATTTAAGGCGTT-3') and TTV1-2340R (5'-GGTCATCAGACGATCCATCTCCCTCAG-3') as described previously (Huang et al., 2010). The resulting amplicon was gel-purified by QIAquick Gel Extraction Kit (Qiagen) and quantified by a NanoDrop spectrophotometer that was used for the real-time PCR standard template of porcine TTV species 1. A full-length DNA clone of PTTV2c-VA strain, pSC-PTTV2c, was constructed by assembling PCR fragments E and F from PTTV2c-VA in the vector pSC-B-amp/kan (Huang et al., unpublished data). Plasmid pSC-PTTV2c (7082 bp) was used for the real-time PCR standard template of porcine TTV species 2 and the plasmid DNA concentration was measured by a NanoDrop spectrophotometer. A 10-fold dilution series of the two templates was used to generate the real-time PCR standard curves, respectively.

Example 6

Extraction of Viral DNA for PCR Assays

Total DNA was isolated from 20 serum and 19 semen samples collected from 20 conventional adult boars (with no clinical syndromes) from a Virginia pig farm using QIAamp DNA mini kit (Qiagen) as described previously (Huang et al., 2010). A sample volume of 400 µl for sera and semen was used to extract DNA with a final eluate of 50 µl sterile water. All extracted DNA samples were stored at −20° C. until real-time PCR testing. Detection of porcine TTVs in these samples by conventional nested PCR had been described previously (Huang et al., 2010). Total DNA extracted from a goat serum sample with the same procedure was used as the negative control.

Example 7

SYBR Green Real-Time Quantitative PCR Assays

PTTV1- and PTTV2-specific real-time PCR were performed, respectively, using SensiMix SYBR & Fluorescein kit (Quantace Ltd) and the MyiQ iCYCLER Real Time PCR instrument (BIO-RAD Laboratories). Each 25-µl reaction contained 12.5 µl of SYBR green Master Mix, 4 µl of extracted DNA, 0.5 μl of each primer (10 nM) and 7.5 μl of sterile water. The PCR condition for PTTV1 was 10 min at 95° C. followed by 40 cycles of amplification (15 sec at 95° C., 30 sec at 59.4° C., 10 sec at 72° C.). This was immediately followed by a melting point analysis obtained by gradually increasing the temperature form 55° C. to 95° C. with the fluorescence signal being measured every 0.5° C. The PCR condition for PTTV2 was the same as PTTV1 except that the annealing temperature was 56° C. PTTV1 and PTTV2 standard templates were included as positive controls in every run. Amplification and data analysis were carried out using MyiQ System software (BIO-RAD Laboratories). All samples were run in duplicate on the same plate.

Example 8

Specificity and Sensitivity of Two Singleplex Assays

The optimal annealing temperatures for amplification of PTTV1- and PTTV2-specific assays were 59.4° C. and 56° C., respectively, as determined by a 10-fold dilution of amplifications using a gradient of annealing temperatures. Amplification of the 118-bp product using primers TTV1F/TTV1R was obtained only with PTTV1 template whereas amplification of the 200-bp product with PTTV2 template was only observed when primers TTVF4/TTVR4 were used. Neither assay yielded any cross-amplification from the other, confirming the specificity of the primers and targets (data not shown).

Figure 6A:
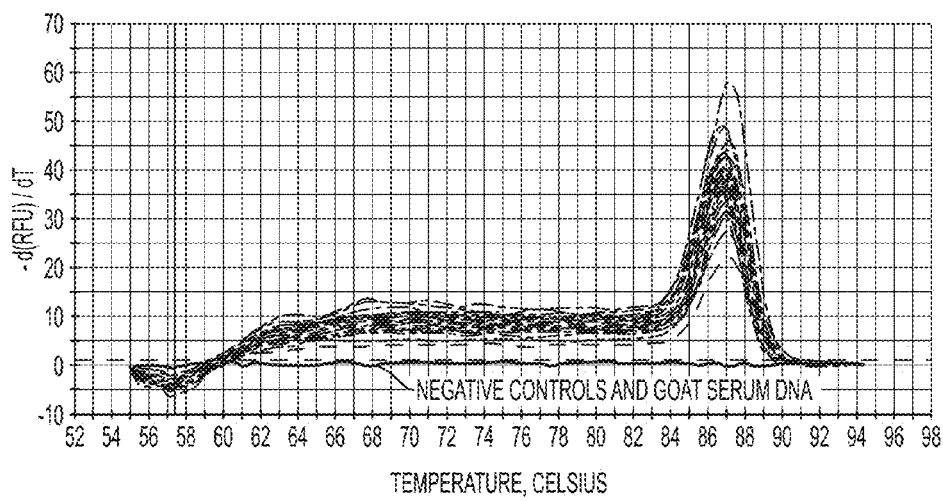
FIG. 6A illustrates melting curves of PTTV1 real-time PCR products after 40 cycles of amplifications of respective standard template (indicated in blue) and 20 porcine serum samples.
Figure 6B:
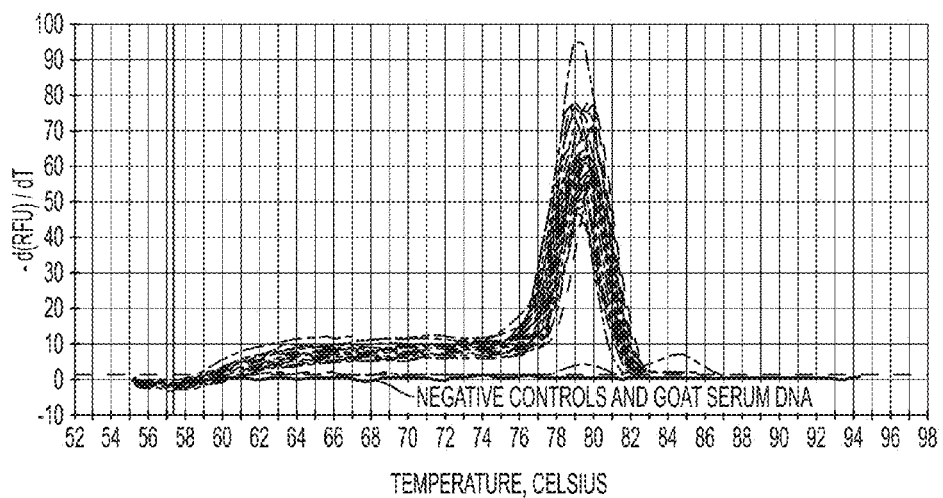
FIG. 6B illustrates melting curves of PTTV2 real-time PCR products after 40 cycles of amplifications of respective standard template and 20 porcine serum samples.

A PTTV1 standard curve was established over a range of target DNA concentrations per 25 μl. The linear range was shown to span $4.4 \times 10^1$ to $4.4 \times 10^8$ copies. The minimum detection limit (44 copies) corresponded to a threshold cycle ($C_t$) of 37.57. Tested samples with $C_t > 37.57$ were considered as below the detection limit and were not quantifiable. Similarly, a PTTV2 standard curve was generated and used to detect DNA concentration ranging from $8.6 \times 10^0$ to $8.6 \times 10^8$ copies per 25 μl reaction. The corresponding $C_t$ of minimum detection limit (8.6 copies) was 36.53. All samples that were considered as PTTV1- or PTTV2-positive had copy numbers lower than the respective maximum detection limit. Melting curves using a 10-fold dilution of PTTV1 or PTTV2 standard template (FIGS. 6a & 6b; blue curves), as well as 20 boar serum samples, displayed melting temperatures ($T_m$) of 87.0° C. for PTTV1 and 80.0° C. for PTTV2, respectively (FIGS. 6a & 6b; red curves). No peaks were observed for the negative controls using sterile water or goat serum DNA as templates (FIGS. 6a & 7b; black lines).

Example 9

Quantification of Porcine TTV1 and TTV2 in Boar Serum and Semen Samples

Viral load was expressed as copy numbers of PTTV1 or PTTV2 genomes per ml of original boar serum samples. PTTV1 DNA were detected in all 20 serum samples ranging from $1.91 \times 10^3$ to $3.25 \times 10^5$ copies/ml whereas PTTV2 DNA were detected in 19 serum samples (except #10) ranging from $3.59 \times 10^2$ to $1.39 \times 10^6$ copies/ml. The result was consistent to our previous study by using conventional nested PCR (Table 5). None of the semen samples were PTTV1-positive whereas three semen samples were PTTV2-positive with very low viral loads (230, 244 and 357 copies/ml, respectively).

TABLE 5

Comparison of porcine TTVs detection by different assays in 20 serum and 19 semen samples from adult boars in a Virginia Farm.

| | No. of positive/total no. tested by different assay | | | | |
|---|---|---|---|---|---|
| Samples | PTTV1 real-time PCR | PTTV1 nested PCR | PTTV2 real-time PCR | PTTV2 nested PCR | PTTV1/PTTV2 duplex real-time PCR |
| Serum PTTV1 | 20/20 | 20/20 | — | — | 20/20 |
| Serum PTTV2 | — | — | 19/20 | 19/20 | 19/20 |
| Semen PTTV1 | 0/19 | 1/19 | — | — | — |
| Semen PTTV2 | — | — | 3/19 | 3/19 | — |

Example 10

PTTV1/PTTV2 Duplex Real-Time PCR Assay

PTTV1/PTTV2 duplex real-time PCR assay was performed in a 25-μl PCR system containing 12.5 μl of SYBR green Master Mix, 0.5 μl of each PTTV1 primers, 0.5 μl of each PTTV2 primers, 4 μl of DNA and 6.5 μl of sterile water. The duplex PCR condition and melting point analysis were the same as PTTV1 except that the annealing temperature was 58° C. The melting peaks were analyzed to distinguish the PTTV1- and PTTV2-specific amplicons.

Example 11

Duplex Nested PCR

The first-round PCR was performed with a Platinum PCR HiFi Supermix (Invitrogen) using 4 μl of extracted DNA in a total volume of 50 μl. The PCR condition was 30 cycles of 94° C. for 30 sec, 55° C. for 30 sec, 72° C. for 30 sec with an initial denaturation of the template DNA at 94° C. for 2 min. A 4-μl aliquot of the first-round PCR product was used for the second-round PCR with the same PCR reagents and condition. One pair of primers P1ab-mF/P1ab-mR was used in the first-round PCR whereas a mixture of two pairs of primers, P1a-nF/P1a-nR for detection of PTTV1a, and P1b-nF/P1b-nR for detection of PTTV1b, were used in the second-round PCR (Table 1). The amplification products were visualized by gel electrophoresis on a 1% agarose gel stained with ethidium bromide and two bands specific for each type were differentiated by UV light.

Example 12

Construction of PTTV1 and PTTV2 ORF Expression Plasmids

The C-terminal parts of ORF1 of PTTV1a, PTTV1b and PTTV2c were amplified from the respective full-length DNA clones (pSC-PTTV1a, pSC-PTTV1b and pSC-PTTV2c; described elsewhere). The amplified fragments were expected to encode protein products with 319 aa for PTTV1a (ORF1 aa positions 317-635 (SEQ ID NO:13); GenBank accession no. GU456383), 318 aa for PTTV1b (ORF1 aa positions 322-639 (SEQ ID NO:14); GenBank accession no. GU456384), and 316 aa for PTTV2c (ORF1 aa positions 310-625 (SEQ ID NO:16); GenBank accession no. GU456386), respectively. A C-terminal truncated fragment of PTTV1b encoding 248 aa (ORF1 aa positions 322-569 (SEQ ID NO:14)) was also amplified and used as a comparison control for SDS-PAGE analysis. All the plasmids were constructed by cloning of the PCR products into an E. coli/baculovirus/mammalian cells triple expression vector pTriEx1.1-Neo (Novagen) between the NcoI and XhoI restriction sites to generate C-terminally 8×His-tagged fusion proteins. The four recombinant plasmids were designated pTri-PTTV1a-ORF1, pTri-PTTV1b-ORF1, pTri-PTTV1b-ORF1ctruc and pTri-PTTV2c-ORF1. All cloned sequences were confirmed by DNA sequencing.

Example 13

Expression of Recombinant PTTV1 and PTTV2 Proteins

The four expression plasmids were transformed into Rosetta 2 (DE3) pLacI competent cells (Novagen), respectively, and the bacteria were plated on LB agar plates containing 100 µg/ml ampicillin overnight at 37° C. A single transformation colony for each construct was used to inoculate 3 ml of LB medium containing 100 µg/ml of ampicillin (LB/amp), and grown 6-8 hours at 37° C. The turbid 3 ml culture for each construct was then used to make bacterial stocks by adding 25% filter sterilized glycerol, and freezing the culture down at −80° C. Prior to purification, 10 µl of the frozen bacterial stock for each construct was used to inoculate a 3 ml starter culture of LB/amp, and grown for 6-8 hours at 37° C. A 100-ml of Overnight Express TB Media (Novagen) was inoculated with the starter culture to induce protein expression, and was grown 16-18 hours at 37° C. After incubation, the autoinduction culture underwent centrifugation at 3400 rpm for 15 minutes at 4° C. The resulting supernatant for each construct was discarded, and each of the bacterial pellets was reserved at −20° C. until use.

Example 14

Purification and Dialysis of Recombinant Proteins

The recombinant proteins were insoluble and expressed within the bacterial inclusion bodies. Each of the bacterial pellets was treated with BugBuster and rLysozyme according to the manufacture's protocol (Novagen), and Benzonase Nuclease (Novagen) was added for degradation of DNA and RNA. Each of the inclusion body pellets was subsequently resuspended with 840 µl of lysis buffer (6M Guanidine Hydrochloride, 0.1M sodium phosphate, 0.01M Tris-Chloride, 0.01M imidazole, pH 8.0), and frozen at −80° C. for at least 30 minutes. It was then thawed, diluted with an additional 2.5 ml of lysis buffer and gently rotated for 30 minutes at room temperature. The lysate supernatants were collected by centrifugation at 15,000×g for 30 minutes at room temperature. A 50%-Ni-NTA His-bind slurry (Novagen) was added to each of the decanted supernatants, and the mixtures were shaken for 60 minutes at room temperature to promote his-tag binding. The lysate/resin mixtures were loaded into an empty chromatography column. After the initial flow-through, a 7-ml of lysis buffer was added to the column and allowed to flow through. Each column was then washed 2 times with 7 mL of wash buffer (8M Urea, 0.1M Sodium Phosphate, 0.15M Sodium Chloride, 0.02M imidazole, pH 8.0). Elution of the target protein was achieved by adding 4 separate 1 ml aliquots of elution buffer (8M Urea, 0.05M Sodium Phosphate, 1M Sodium Chloride, 0.5M Imidazole, pH 8.0) to the column. The four elution fractions were analyzed by SDS Page and Coomasie Blue Staining.

The elutions containing significant concentrations of the target protein were injected into a 0.5 ml-3 ml dialysis cassette with a 20,000 molecular weight cut-off (Pierce). A series of 4 dialysis buffers were used for dialysis; dialysis buffer 1 (6M Urea, 0.05M Sodium Phosphate, 0.8M Sodium Chloride, 0.3M Imidazole, pH 8.0), dialysis buffer 2 (4M Urea, 0.033M Sodium Phosphate, 0.533M Sodium Chloride, 0.2M Imidazole, pH 8.0), dialysis buffer 3 (2.67M Urea, 0.022M Sodium Phosphate, 0.356M Sodium Chloride, 0.133M Imidazole, pH 8.0) and dialysis buffer 4 (1.5M Urea, 0.0148 Sodium Phosphate, 0.237M Sodium Chloride, 0.089M Imidazole, pH 8.0). The dialysis cassette was sequentially submerged and rotated in each dialysis buffer for over 6 hours at 4° C. When dialysis was complete, the recombinant His-tagged fusion proteins were each removed from the cassettes, quantified using a NanoDrop and frozen at −80° C.

Example 15

SDS-PAGE and Anti-His-Tagged Western Blot

A western blot was developed to detect purified recombinant proteins by using an anti-6×His-tagged monoclonal antibody (Rockland). Equal volumes of each of the purified truncated ORF1 proteins and LDS/10% β-ME were mixed, and boiled at 95° C. for 10 minutes. A 10-µl of the boiled sample was added to each appropriate well of a 4-12% Bis-Tris Polyacrylamide Gel (Invitrogen), and was run at 200 volts for 43 minutes in 1×MES running buffer (Invitrogen). The proteins were transferred to a PVDF membrane (Bio-Rad) using a Trans blot semi dry transfer apparatus and 1× transfer buffer (Invitrogen). Once transfer was complete, the PVDF membrane was incubated in Odyssey blocking buffer (Li-Cor) at room temperature for 1 hour. The anti-6× His-tagged MAb was diluted at 1:1000 in Odyssey blocking buffer/0.2% tween 20, and transferred to the membrane after the previous Odyssey blocking buffer was removed. The MAb was left on a rocker to incubate with the membrane for either 2 hours at room temperature or 4° C. overnight, and then the membrane was washed 3 times with tris buffered saline/0.05% tween 20 (TBS-T, Sigma). A Goat anti-rabbit IgG IRDye 800 (Li-Cor) antibody was diluted at 1:5000 in Odyssey blocking buffer/0.2% tween 20/0.1% SDS. It was transferred to the freshly washed PVDF membrane, and allowed to incubate for 1 hour at room temperature while gently rocking. The membrane was washed 3 times with TBS-T, 1 time with TBS and imaged with the Li-Cor Odyssey.

Example 16

Serum Western Blot

A serum western blot was developed, and used to identify positive and negative serum controls for ELISA development. After SDS-PAGE as described above, the proteins were transferred to a PVDF membrane that was subsequently incubated in Odyssey blocking buffer (Li-Cor) at room temperature for 1 hour. A selected serum sample was diluted at 1:100 in Odyssey blocking buffer/0.2% tween 20, and transferred to the membrane after the previous Odyssey blocking buffer was removed. The serum sample was left on a rocker to incubate with the membrane for 2 hours at room temperature, and then the membrane was washed 3 times with tris buffered saline/0.05% tween 20 (TBS-T, Sigma). A goat anti-swine IgG IRDye 800 antibody (Rockland) was diluted at 1:2500 in Odyssey blocking buffer/0.2% tween 20/0.1% SDS. It was transferred to the freshly washed PVDF membrane, and allowed to incubate for 1 hour at room temperature while gently rocking. The membrane was washed 3 times with TBS-T, 1 time with TBS and imaged with the Li-Cor Odyssey.

Example 17

Indirect PTTV1a-, PTTV1b- and PTTV2-Specific ELISA

The optimal concentrations of the antigens used to coat the plates and dilutions of antisera and conjugates were determined by checkboard titration. The ELISA was initiated by diluting each of the purified recombinant His-tagged fusion proteins (PTTV1a, PTTV1b and PTTV2c, respectively) to 680 ng/ml in 1× Carbonate Coating Buffer (CCB) at a pH of 9.6, and coating medium binding ELISA plates (Greiner) with 100 μl/well. The plates were covered, and allowed to incubate at 37° C. for 2 hours. After coating, the diluted proteins were removed, and each well was washed 3 times with 300 μl of 1×TBS-T. Protein Free Blocking Buffer (Pierce) was then added at a volume of 300 μl/well, and the plates were allowed to incubate at 37° C. for 1 hour. Meanwhile, in a 96-well dilution block, the serum samples were diluted at 1:100 in 150 μl of protein free blocking buffer. The block was then removed, and 100 μl of each diluted serum sample was transferred to each corresponding well on the ELISA plates. The plates were allowed to incubate at 37° C. for 2 hours, after which each well was washed 3 times with 300 μl of TBS-T. Next, the HRP-conjugated anti-swine IgG antibody (Rockland) was diluted at 1:4000 in 12 ml of protein free block, and 100 μl was added to each well of the plates. This was incubated at 37° C. for 1 hour, and then each well was washed 3 times with 300 μl of TBS-T. In order to develop the ELISA, 100 μl of Sure Blue Reserve 1-Component (KPL) was added to each well of the plates. After 20 minutes, 100 μl of 1N HCL was added to each well to stop development. The plates were then read at 450 nm.

Example 18

Data Analyses

Porcine sera used in cell culture research from a commercial company (manufactured in New Zealand and considered free from all OIE diseases) were used as a positive control for the three ELISA protocols because the sera were all PTTV1a-, PTTV1b- and PTTV2-positive as detected by serum western blot and displayed high OD values (>2.0). We initially used pooled gnotobiotic pig sera as a negative control as they were negative in western blot detection. Subsequently, in comparison of the negative gnotobiotic pig sera, we screened some porcine sera collected from a conventional pig farm in Wisconsin. They were also negative in western blot detection and their OD values corresponded to that of negative gnotobiotic pig sera. These conventional porcine sera were pooled and used as a negative control. The cutoff value for each ELISA was calculated as the mean OD value of the negative control group (n=4) plus 3 times of the standard deviation.

Example 19

Construction of Full-Length Genomic DNA Clones of Porcine TTV1a, 1b and 2c

PCR fragments B and C from the US isolate PTTV1a-VA (GenBank accession no. GU456383) were re-amplified from the constructs described previously, and were subsequently assembled into a full-length genomic DNA with a BamH I site at the both ends of the genome by overlapping PCR using the Herculase II Fusion DNA Polymerase (Stratagene) on the vector pSC-B-amp/kan (Stratagene). The resulting construct was designated pSC-PTTV1a (FIG. 17A). Using the same strategy, the clone pSC-PTTV1b (FIG. 17B) originated from the US isolate PTTV1b-VA (GenBank accession no. GU456384) and the clone pSC-PTTV2c (FIG. 17C) originated from the US isolate PTTV2c-VA (GenBank accession no. GU456386) were constructed with the same restriction sites (BamH I) on the same backbone vector. Plasmid TTV2-#471942-full (FIG. 17E) containing a full-length genomic DNA originated from a Germany pathogenic porcine TTV2 isolate. TTV2-#471942 was a gift from Dr. Andreas Gallei (BIVI, Germany). TTV2-#471942 was classified into the porcine TTV subtype 2b together with the US isolate PTTV1b-VA based upon the phylogenetic analysis (data not shown).

Example 20

Construction of Tandem-Dimerized DNA Clones of Porcine TTV2b and 2c

The full-length PTTV2c genome was excised from the clone pSC-PTTV2c by BamH I digestion, purified and ligated to form concatemers. Ligated concatemers were cloned into the BamH I-pre-digested pSC-B-amp/kan vector to produce a tandem-dimerized DNA clone, pSC-2PTTV2c-RR (FIG. 17D). Similarly, a tandem-dimerized DNA clone, pSC-2PTTV2b-RR, was generated from the clone TTV2-#471942-full using EcoR V restriction sites (FIG. 17F).

Example 21

Generation of PTTV1a-, PTTV1b- and PTTV2-Specific Anti-ORF1 Polyclonal Antibodies The ORF1-encoding product is the putative capsid protein of TTV. To generate PTTV1a-, PTTV1b- and PTTV2-specific anti-ORF1 polyclonal antibodies to detect the expression of PTTV ORF1 proteins and to determine the infectivity of PTTV DNA clones, the three ORF1 proteins from PTTV1a, PTTV1b and PTTV2c were expressed in *E. coli*, purified and were subsequently used to immunize New Zealand white rabbits, respectively, as a custom antibody production service at Rockland Immunochemicals (Gilbertsville, Pa.). Each anti-ORF1 polyclonal antibody was produced from serum of immunized rabbits.

Example 22

In Vitro Transfection of PTTV Infectious Clones

PK-15 cells were seeded at $2\times10^5$ cells per well onto a 6-well plate and grown until 60%-70% confluency before transfection. The DNA clones pSC-2PTTV2b-RR and pSC-2PTTV2c-RR were directly transfected into PK-15 cells, respectively, using Lipofectamine LTX (Invitrogen) according to the manufacturer's protocol. For clones pSC-PTTV1a, pSC-PTTV2c and TTV2-#471942-full, their ligated concatemers, produced as described above, were used for transfection, respectively. Cells were cultured for 3 to 5 days, and were then applied to an immunofluorescence assay (IFA) to detect the expression of ORF1 of porcine TTVs. Alternatively, transfected cells were passaged into new 6-well plates and continued to culture for 3 days before the IFA detection.

Example 23

Immunofluorescence Assay (IFA)

Transfected or passaged cells were washed 2 times with PBS and fixed with acetone. Five hundred microliters of the antibodies, specific to PTTV1a or PTTV2 at 1:500 dilution in PBS, was added over the cells and incubated for 1 hour at room temperature. Cells were washed 3 times with PBS and 500 μl Texas red- or Alexa Fluor 488-labeled goat anti-rabbit IgG (Invitrogen) at 1:200 dilution was then added. After 1-hour incubation at room temperature and washed with PBS, the cells were stained with 500 μl DAPI (KPL, Inc.) at 1:1000 dilution and visualized under a fluorescence microscope.

Example 24

In Vivo Inoculation of Conventional Pigs with the Tandem-Dimerized Porcine TTV2 Clones A pig inoculation study was performed to determine the infectivities of the two tandem-dimerized porcine TTV2 clones: pSC-2TTV2b-RR and pSC-2TTV2c-RR. Briefly, eight 4-week-old conventional pigs that were seronegative and viral DNA negative for porcine TTV2 were randomly assigned into two groups of four each. Each group of pigs was housed separately and maintained under conditions that met all requirements of the Institutional Committee on Animal Care and Use.

All pigs in each group were injected by a combination of both the intra-lymph node route and intramuscular route. The four pigs (nos. 181, 189, 192 and 193) were each injected with 200 μg of the pSC-2TTV2b-RR plasmid DNA whereas another four pigs (nos. 92, 180, 188 and 191) were each inoculated with 200 μg of the pSC-2TTV2c-RR clone. Pigs were monitored daily for clinical signs of disease for a total of 28 days. All pigs were necropsied at 28 days postinoculation.

While the present invention has been illustrated by description of several embodiments and while the illustrative embodiments have been described in detail, it is not the intention of the applicants to restrict or in any way limit the scope of the appended claims to such detail. Additional modifications will readily appear to those skilled in the art. The invention in its broader aspects is therefore not limited to the specific details, representative apparatus and methods, and illustrative examples shown and described. Accordingly, departures may be made from such details without departing from the spirit or scope of applicants' general inventive concept.

SEQUENCE LISTING

```
<160> NUMBER OF SEQ ID NOS: 62

<210> SEQ ID NO 1
<211> LENGTH: 32
<212> TYPE: DNA
<213> ORGANISM: Torque teno virus

<400> SEQUENCE: 1
catagggtgt aaccaatcag atttaaggcg tt                                32

<210> SEQ ID NO 2
<211> LENGTH: 27
<212> TYPE: DNA
<213> ORGANISM: Torque teno virus

<400> SEQUENCE: 2
ggtcatcaga cgatccatct ccctcag                                      27

<210> SEQ ID NO 3
<211> LENGTH: 28
<212> TYPE: DNA
<213> ORGANISM: Torque teno virus

<400> SEQUENCE: 3
cttctgaggg agatggatcg tctgatga                                     28
```

<210> SEQ ID NO 4
<211> LENGTH: 28
<212> TYPE: DNA
<213> ORGANISM: Torque teno virus

<400> SEQUENCE: 4
ttgagctccc gaccaatcag aattgact                                              28

<210> SEQ ID NO 5
<211> LENGTH: 22
<212> TYPE: DNA
<213> ORGANISM: Torque teno virus

<400> SEQUENCE: 5
ttgtgccgga gctcctgaga gc                                                    22

<210> SEQ ID NO 6
<211> LENGTH: 24
<212> TYPE: DNA
<213> ORGANISM: Torque teno virus

<400> SEQUENCE: 6
aggtgcttga ggagtcgtcg cttg                                                  24

<210> SEQ ID NO 7
<211> LENGTH: 27
<212> TYPE: DNA
<213> ORGANISM: Torque teno virus

<400> SEQUENCE: 7
tacccaggcg gttagacact cagctct                                               27

<210> SEQ ID NO 8
<211> LENGTH: 27
<212> TYPE: DNA
<213> ORGANISM: Torque teno virus

<400> SEQUENCE: 8
ctcaagcacg agcagtggat cctctca                                               27

<210> SEQ ID NO 9
<211> LENGTH: 2878
<212> TYPE: DNA
<213> ORGANISM: Torque teno virus

<400> SEQUENCE: 9
tacacttccg ggttcaggag gctcaatttg gctagcttcg ctcgcaccac gtttgctgcc           60
aggcggacct gattgaagac tgaaaaccgt taaattcaaa tttgaaaatg gcgggcaaaa          120
tggcggaagg ggggcggagt ttatgcaaat taatttatgc aaagtaggag gagctcgatt          180
ttaatttatg caaagtagga ggagtcaatt ctgattggtc gggagctcaa gtcctcattt          240
gcatagggtg taaccaatca gatttaaggc gttcccccaa aagtgaatat aagtaagcgc          300
agttccgaat ggctgagttt atgccgccag cggtagacag aactgtctag cgactgggcg          360
ggtgccggag gatccctgat ccggagtcaa ggggcctatc gggcaggagc agctgagcgg          420
agggcctaca tgaaggagaa agactactgg gaggaagcct ggctgaccag ctgtacatct          480
atacacgacc accactgcaa ctgcggtagc tggagagacc acctgtggac gctatgcgct          540
ttagacgacg cagatttggc cgccgccgca gatattatag aaagagaaga ggcggatgga          600

| | |
|---|---|
| ggagaagatt tcggattcgt agacggagac cctggagacg ctggcgggta aggagatggc | 660 |
| ggcgttccgt cttccgtaga gggggacgta gagcgcgccc ctaccgcatt agcgcttgga | 720 |
| accctaaggt tctcagaaac tgccgcatca cgggatggtg gccagttata cagtgtatgg | 780 |
| acgggatgga gtggataaaa tacaagccta tggacttaag agtcgaggca aactggatat | 840 |
| tcaataaaca ggacagtaaa atagagacag aacagatggg atacctgatg cagtatggag | 900 |
| gagggtggtc aagcggagta atcagcttag agggactatt caatgaaaac agactgtgga | 960 |
| gaaatatatg gtcaaaaagc aatgacggga tggacttggt cagatacttt ggctgtagaa | 1020 |
| ttagactata tccaacagag aatcaggact acttgttctg gtatgacaca gaatttgacg | 1080 |
| aacagcaaag gagaatgcta gatgaataca cacaacctag tgtgatgctg caggctaaaa | 1140 |
| actcgcgtct aatagtgtgt aaacagaaga tgccaattag acgcagagta aaaagtattt | 1200 |
| ttataccgcc gcctgcacag ttaacaactc agtggaaatt tcaacaggaa ctatgtcagt | 1260 |
| ttccactgtt taactgggcc tgtatctgca tagacatgga cacgccgttc gactacaacg | 1320 |
| gcgcatggcg aaatgcctgg tggctaatga aaggctgcaa aaacgaaaac atggagtaca | 1380 |
| tagaaagatg gggcagaata ccaatgacag gagacacaga actaccacca gcagacgact | 1440 |
| tcaaggcagg aggggtgaac aaaaaacttca aaccgacagg tattcaaaga atatacccga | 1500 |
| tagtagcggt atgccttgta gaagggaaca aaagagtagt caaatgggcc acagtacaca | 1560 |
| atggtcccat agacagatgg agaaaaaaac agacaggaac tttaaagctc tctaacctga | 1620 |
| gaggcctagt actgagagta tgctcagaga gtgaaacata ctataagtgg acaggatcag | 1680 |
| aatttacagg ggcatttcaa caagactggt ggccagtagg cggaacagaa tacccgcttt | 1740 |
| gtaccattaa aatggaccca gaatatgaaa accctacagt agaggtatgg tcctggaaag | 1800 |
| caaatatacc gacatcaggg actcttaaag actacttcgg actgagtaca gggcaacagt | 1860 |
| ggaaagacac tgactttgcg aggctgcaac tacctagaag cagccacaat gtggactttg | 1920 |
| gacataaagc tagatttggg ccattttgcg ttaaaaagcc tccagtagag ttcagagata | 1980 |
| cagccccaaa cccactaaat atatgggtaa aatacacgtt ctattttcag ttcggcggca | 2040 |
| tgtaccagcc tcccaccgga atccaagatc cctgcacttc taacccgacc tatcctgtca | 2100 |
| gaatggtcgg agcagttaca caccccaaat acgccgggca aggcggaatc acgacccaaa | 2160 |
| ttggagatca aggtatcacc gctgcctcta tccgtgccat cagtgcagct ccaccagata | 2220 |
| cctacacgca gtcggcgttc ctcaaagccc cggaaaccga gaagaagag gaaagagaga | 2280 |
| gtgagaccag tttcacgagt gccgaaagct cttctgaggg agatggatcg tctgatgacc | 2340 |
| aagcagagag acgcgctgcc agaaagcgag tcatcaagtt acttctcaag cgactcgctg | 2400 |
| acagacccgt ggcaacaag cgacgacgat tttcagagtg accctgaccc cctcaccaat | 2460 |
| aaacgcaaaa aacgcttgca attctaactc tgtctctgtg acttcattgg ggggtccgg | 2520 |
| gggggcttgc cccccgtta gttgggttct cgcactcccg cctgccaagt gaaactcggg | 2580 |
| gaggagtgag tgcgggacat cccgtgtaat ggctacataa ctacccggct ttgcttcgac | 2640 |
| agtggccgtg gctcgaccct cacacaacac tgcagatagg gggcgcaatt gggatcgtta | 2700 |
| gaaaactatg gccgagcatg gggggggctc cgccccccc aacccccccg gtggggggc | 2760 |
| caaggccccc cctacacccc cccatggggg gctgccgccc ccaaacccc ccgcgtcgga | 2820 |
| tggggggggc tgcgcccccc ccaaacccccc cttgcccggg gctgtgcccc ggaccccc | 2878 |

<210> SEQ ID NO 10
<211> LENGTH: 2875

<212> TYPE: DNA
<213> ORGANISM: Torque teno virus

<400> SEQUENCE: 10

```
tacacttccg ggttcaggag gctcaatttg gctcgcttcg ctcgcaccac gtttgctgcc        60
aagcggacct gattgaagac tgacaaccgt tacattcaaa tttgaaaatg gcgcccaaac       120
atggcggcgg ggggcggagt ttatgcaaat taatttatgc aaagtaggag gagctccatt       180
ttaatttatg caaagtagga ggagtcaatt ctgattggtc gggagctcaa gtcctcattt       240
gcatagggtg taaccaatca gatttaaggc gttcccatta aagcgaatat aagtaagtga       300
ggttccgaat ggctgagttt atgccgccag cggtagacag aactgtctag cgactgggcg       360
ggtgccggag gatccctgat ccggagtcaa ggggcctatc gggcaggagc agctgagcgg       420
agggcctatg ccggaacact gggaggaagc ctggttggaa gctaccaagg gctggcacga       480
tctcgactgc cgctgcggta actggcagga ccacctatgg ctcctactcg ccgatggaga       540
cgccgctttg gccgccgccg tagacgctat agaaagagac gctatgggtg gagaagacgt       600
tactaccgct acagaccgcg ttactatagg agacgatggc tggtaaggag aaggcggcgt       660
tccgtctacc gtagaggtgg acgtagagcg cgcccctacc gaataagtgc ttttaaccca       720
aaagtaatgc ggagggtggt gattagaggt tggtggccaa tattacagtg tctaaaagga       780
caggaatcac taagatatag accactgcag tgggacactg aaaaacagtg gagagtaaag       840
aaagactatg aggacaacta cggctacttg gtgcagtacg gaggaggttg ggggagtggt       900
gaagtgacat tggagggatt atatcaggaa cacttactct ggagaaactc ttggtcaaag       960
ggaaatgatg gcatggacct agtgagatac tttggctgca tagtatacct gtacccactg      1020
caggaccaag actactggtt ttggtgggat acagacttta agaactata cgcagagagc       1080
atcaaagaat actcccagcc aagtgttatg atgatggcca aacgcactag actagtaata      1140
gctagagaca gagcaccaca cagaagaaga gtaagaaaaa ttttcatacc cccgccaagc      1200
agagacacca cacaatggca atttcagaca gacttctgca aaaggccact attcacatgg      1260
gcggcaggat taatagacat gcagaaacca tttgatgcaa acggagcgtt tagaaacgcc      1320
tggtggctag aaacaaggaa tgaccaggga gaaatgaaat acattgaact atggggaagg      1380
gtgccaccac agggtgacac agaactgcca aaacagagtg agtttaagaa gggagataat      1440
aaccctaact ataacataac ggaaggacat gaaaaaaata tttacccaat aatcatatac      1500
gttgaccaga aagaccagaa aacaagaaaa aaatactgtg tatgctacaa caaaacttta      1560
aatagatgga gaaaagccca ggcgagtaca ttagcaatag gagatcttca aggactagta      1620
ctgcgtcagc ttatgaatca ggagatgaca tactactgga atcgggaga gttttcctca       1680
ccattcctgc aaagatggaa aggaactagg ctaataacca tagacgcaag aaaggcagac      1740
acagaaaacc caaagtaag ttcgtgggaa tgggggcaaa actggaacac aagcggaaca       1800
gtgctacagg aggtattcaa catttcactg aacaacactc aaataagaca ggatgacttt      1860
gcaaaattga cactgccaaa gtcaccacat gacatagact ttggacatca cagcagattt      1920
ggaccattct gtgttaaaaa cgaaccacta gaattccaac tactgcctcc aacaccaact      1980
aacctatggt ttcagtacaa atttctcttt cagtttggcg gtgaatacca gccaccaaca      2040
ggtatccgcg atccctgcat tgatacacca gcctatcctg tgccgcagtc aggaagtgtt      2100
acacacccca aattcgccgg aaagggcgga atgctcacgg aaacagaccg ttggggtatc      2160
actgctgcct cttccagaac cctcagtgca gatacaccca ccgaagcagc gcaaagtgca      2220
```

```
cttctcagag gggacgcgga aaagaaagga gaggaaaccg aggaaaccgc gtcatcgtcc    2280
agtatcacga gtgccgaaag ctctactgag ggagatggat cgtctgatga tgaagagaca    2340
atcagacgca gaaggaggac ctggaagcga ctcagacgga tggtcagaca gcagcttgac    2400
cgacgaatgg accacaagcg acagcgactt cattgatacc cccataagag aaagatgcct    2460
caataaaaaa caaaaaaaac gctaaacagt gtccgcctat tagtgggggg gtccgggggg    2520
gcttgccccc ccgtaagcgg ggttaccgca ctaactccct gccaagtgaa actcggggac    2580
gagtgagtgc gggacatccc gtgtaatggc tacataacta cccggctttg cttcgacagt    2640
ggccgtggct cgaccctcgc acaacactgc aggtaggggg cgcaattggg atcgttagaa    2700
aactatggcc gagcatgggg ggggctccgc cccccccaac ccccccggtg gggggggccaa   2760 ggcccctccct acaccccccc atgggggggct gccgccccccc aaaccccccg cgtcggatgg   2820 gggggggctgc gccccccccca aaccccccctt gcccggggct gtgccccgga cccccc       2875

<210> SEQ ID NO 11
<211> LENGTH: 2750
<212> TYPE: DNA
<213> ORGANISM: Torque teno virus

<400> SEQUENCE: 11
taatgacagg gttcaccgga aaggctgcaa aattacagct aaaaccacaa tcataacaca      60 ataaccaca aactattaca ggaaactgca ataaattaag aaataaatta cacataacca     120
cctaaccaca ggaaactttg caaaaaggg gaaataaatc tcattggctg gccagaagt      180 cctcattaga ataagaaaag aaccaatcag aaacacttcc tcttttagag tatataagta    240
agtgcgcaga cgaatggctg agtttatgcc gctggtggta gacacgaaca gagctgagtg    300
tctaaccgcc tgggcgggtg ccggagctcc tgagagcgga gtcaagggcc ctatcgggca    360
ggcggtaatc cagcggaact gggcccccct ccatggaaga aagatggctg acggtagcgt    420
actgcgcgca cggattattc tgcgactgta aaacccgaa aaaacatctt gaaaaatgcc     480
ttacagacgc tatcgccgac gccgaaggag accgacacgg agatggaggc accggaggtg    540
gagacgctac tttcgatatc ggtatcgacg cgctcctcgc cgccgccgcc caaaggtaag    600
gagacggagg aggaaagctc cggtcattca atggttccct cctagccgga gaacctgcct    660
catagagggc ttctggccgt tgagctacgg acactggttc cgtacctgtc tcccctatgag   720 aaggctaaac ggactgattt tcacgggtgg aggatgtgac tggactcaat ggagtttaca    780
aaatttattc catgaaaaat taaactggag aaatatatgg acagcttcta atgtaggcat    840
ggagtttgct agattttttaa gaggaaaatt ttacttcttc agacacccct ggagaagcta   900
tatagtaaca tgggaccaag acatacccctg taaaccgctc ccatatcaaa acttacaacc    960
tctattaatg ctccctcaaaa aacagcataa attagtcctc tctcaaaaag attgcaaccc   1020
gaacagaaaa caaaaaccag ttacattaaa attcaggcct ccaccaaaat taacatcaca   1080
gtggagacta agcagagaac tctcaaaaat acccttaata agactaggaa taagtctcat   1140
agacctgtca gaaccatggt tagaaggctg gggaaatgct ttttacagtg tactaggata   1200
tgaagctagt aaaacagtg gcagatggtc caactgggaca caaatgaaat attttttggat 1260 ctatgacaca ggcgtgggaa acgcagtcta cgttatttta ctgaaaaaag acgtgagtga    1320
caatccagga gacatggcta cacagtttgt aacaggctca ggacaacacc cagacgcaat    1380
agatcatata gaaatggtaa acgaaggatg gccttactgg ctatttttttt atggacaatc   1440 agaacaagat ataaaaaaac tagcacatga ccaagatata gtcagagaat atgccagaga   1500
```

```
ccctaaatca aaaaaattaa aaataggagt cataggatgg gccagcagta actacacaac    1560
agcagggagc aaccaaaaca gtgtacttca acgccagaa gcaatacaag gtggatatgt    1620
agcttatgca ggatccagaa taccaggcgc aggatctatc acaaatttat ttcaaatggg    1680
atggccagga gatcaaaact ggccacccac aaaccaagac caaaccaatt ttaactgggg    1740
actcagagga ctttgtgtat aagagataa catgaaacta ggagcacaag agctagacga     1800
tgaatgcaca atgctctcct tatttggacc atttgttgaa aaagcaaaca cagcttttgc    1860
tacaaacgac ccaaaatatt ttaggcctga actaaaggac tacaacgtag taatgaaata    1920
tgcttttaaa tttcagtggg gaggacatgg caccgaaaga tttaaaacaa ccatcggaga    1980
tcccagcacc ataccatgtc cctttgaacc cggggaacgg taccaccacg ggtacaaga    2040 ccccgccaag gtacaaaaca cagtcctcaa cccttgggac tatgactgtg acgggattgt    2100
tagaacagat actctcaaaa gacttctcga actccccaca gagacggagg agacggagaa    2160
ggcgtaccca ctccttggac aaaaaacaga gaaagagcca ttatcagact ccgacgaaga    2220
gagcgttatc tcaagcacga gcagtggatc ctctcaagaa gaagagacgc agagacgaaa    2280
gcaccacaag ccaagcaagc gacgactcct caagcacctc cagcgggtgg taaagaggat    2340
gaaaacactg tgatagataa atacagaaac ctagcagacc cctcactcaa tgtcacagga    2400
cacatggaaa aattcatgca actacacata caaaacatac aagaaataag agctaaaaat    2460
gctaaaaaat ccctcaataa actttacttt tctgattaat agcggcctcc tgtgtccaat    2520 ctattttttcc tacacccctt caaaatggcg ggaggaacac aaaatggcgg agggactaag    2580
gggggggcaa gccccccccc gggggttgag gggggttttc cccccctccc cccggtgcag    2640
ggggcggagc ccccgcaccc cccatgcggg ggctccgccc cctgcacccc cgggaggggg    2700
ggaaaccccc cctcaacccc ccgcgggggg caagcccccc tgcacccccc               2750
```

<210> SEQ ID NO 12
<211> LENGTH: 2803
<212> TYPE: DNA
<213> ORGANISM: Torque teno virus

<400> SEQUENCE: 12

```
tcatgacagg gttcaccgga agggctgcaa aattacagct aaaaccacaa gtctaacaca     60 ataaccaca aagtattaca ggaaactgca ataaatttag aaatagatta cacataacca    120
ccaaaccaca ggaaacctac acataaccac caaaccacag gaaacataac caccaaacca    180
caggaaactg tgcaaaaaag gggaaataaa ttctattggc tgggcctgaa gtcctcatta    240
gaataataaa agaaccaatc agaagaactt cctcttttag agtatataag taagtgcgca    300
gacgaatggc tgagtttatg ccgctggtgg tagacacgaa cagagctgag tgtctaaccg    360
cctgggcggg tgccggagct cctgagagcg gagtcaaggg gcttatcggg caggcggtaa    420
tccagcggaa ccgggcccc ctcgatgaa gaaagatggc tgacggtagc gtactgcgcc     480
cacggattat tctgcggatg taaagacccg aaaaaacacc ttgaaaaatg ccttacagac    540
gctatcgcag acgccgaagg agaccgacac ggagatggag gcaccggagg tggagacgct    600
tctttcgata tcggtatcga cgcgctcctc gccgccgccg cacaaaggta aggagacgga    660
ggagaaaagc tccggtcata caatggttcc ctcctagccg gaggacctgc ctcatagagg    720
gcttctggcc gttgagctac ggacactggt tccgtacctg tctccctatg agaaggctga    780
acggactcat tttcacgggt ggcggttgtg actggacaca gtggagttta caaaacttat    840
```

```
accatgaaaa acttaactgg agaaatatat ggacagcttc taatgttggc atggaatttg    900
ctagattttt aagaggaaaa ttttacttct tcagacaccc ctggagaagc tatattatta    960
cttgggacca agacattcct tgcaaacctt taccatacca aaacttacat ccactactta   1020
tgctattaaa aaaacaacat aaacttgtac tatctcaaaa agactgtaat ccaaacagaa   1080
gacaaaaacc agtaacttta aaaataagac ctccaccaaa attaacatca cagtggagat   1140
taagcagaga actagcaaaa atgccacttg tcagactagg agtcagtcta atagacctct   1200
cagaaccatg gttagaaggc tggggaaatg cttttttacag cgtactggga tatgaagcta   1260
gtaaacactc agggagatgg tcaaactgga cacaaataaa atacttctgg atatatgaca   1320
caggagtagg aaatgcagtt tatgtcattt tattaaaaca agaggtggat gataatccag   1380
gggcaatggc aacaaaattt gtaactggac caggacaaca cccagatgcc atagacagga   1440
tcgaacaaat aaatgaagga tggccttact ggcttttctt ttacggacag tcagaacaag   1500
acataaaaaa attagcacac gatcaagaaa tagcaaggga atatgcaaac aatccaaaat   1560
ctaaaaaatt aaaaatagga gtgataggat gggctagcag taactttaca acagcaggca   1620
gctcacaaaa tcaaacacca caaacaccag aagccataca aggaggatac gtagcatatg   1680
caggctcaaa atacaagga gcaggagcaa ttacaaactt atacacagat gcatggccgg   1740
gagaccaaaa ttggccaccct ctaaatagag aacaaacaaa ctttaactgg ggcttaagag   1800
gactctgtat aatgagagat aatatgaaac tgggagctca agaactagat gatgaatgta   1860
caatgctcac acttttttgga ccttttgtgg aaaaagcaaa cacagctttt gctacaaatg   1920
accctaaata cttcagacca gaactcaaag actataacat agtaatgaaa tatgccttta   1980
aatttcagtg ggggaggccac ggaaccgaaa gattcaaaac aaccatcgga gatcccagca   2040
ccataccatg tccctttgaa cccggggaac ggtaccacca cggggtacaa gaccccgcca   2100
aggtacaaaa cacagtcctc aacccttggg actatgactg tgacgggatt gttagaacag   2160
atactctcaa aagacttctc gaactcccca cagagacgga ggagacggag aaggcgtacc   2220
cactccttgg acaaaaaaca gagaaagagc cattatcaga ctccgacgaa gagagcgtta   2280
tctcaagcac gagcagtgga tcctctcaag aagaagagac gcagagaaga agacagcaca   2340
agccaagcaa gcgacgactc ctcaagcacc tccagcgggt ggtaaagaga atgaagacac   2400
tgtgatagat aaaatatagaa acctagcaga ccccctcactc aatgtcacag acacatgga   2460
aaaattcatg caactgcaca tacaaaacgt acaagaaata agagctaaaa atgctaaaaa   2520
atccctcaat aaacttttact tttctgatta ataccggcct cctgtgtcca atctattttt   2580
cctacaccc ttcaaaatgg cgggcgggac acaaatggc ggaggaaact aagggggggg   2640
caagccccc ccggggggtt gagggggggt ttcccccct ccccccggtg caggggggcgg   2700
agccccgca cccccctgc ggggggctccg ccccctgcac cccgggagg ggggaaacc    2760
cccctcaac ccccgcggg gggcaagccc ccctgcaccc ccc                      2803
```

<210> SEQ ID NO 13
<211> LENGTH: 635
<212> TYPE: PRT
<213> ORGANISM: Torque teno virus

<400> SEQUENCE: 13

```
Met Arg Phe Arg Arg Arg Arg Phe Gly Arg Arg Arg Tyr Tyr Arg
1               5                   10                  15

Lys Arg Arg Gly Gly Trp Arg Arg Arg Phe Arg Ile Arg Arg Arg
            20                  25                  30
```

-continued

Pro Trp Arg Arg Trp Arg Val Arg Arg Trp Arg Ser Val Phe Arg
        35                  40                  45

Arg Gly Gly Arg Arg Ala Arg Pro Tyr Arg Ile Ser Ala Trp Asn Pro
 50                  55                  60

Lys Val Leu Arg Asn Cys Arg Ile Thr Gly Trp Trp Pro Val Ile Gln
 65                  70                  75                  80

Cys Met Asp Gly Met Glu Trp Ile Lys Tyr Lys Pro Met Asp Leu Arg
                85                  90                  95

Val Glu Ala Asn Trp Ile Phe Asn Lys Gln Asp Ser Lys Ile Glu Thr
            100                 105                 110

Glu Gln Met Gly Tyr Leu Met Gln Tyr Gly Gly Trp Ser Ser Gly
        115                 120                 125

Val Ile Ser Leu Glu Gly Leu Phe Asn Glu Asn Arg Leu Trp Arg Asn
    130                 135                 140

Ile Trp Ser Lys Ser Asn Asp Gly Met Asp Leu Val Arg Tyr Phe Gly
145                 150                 155                 160

Cys Arg Ile Arg Leu Tyr Pro Thr Glu Asn Gln Asp Tyr Leu Phe Trp
                165                 170                 175

Tyr Asp Thr Glu Phe Asp Glu Gln Gln Arg Arg Met Leu Asp Glu Tyr
            180                 185                 190

Thr Gln Pro Ser Val Met Leu Gln Ala Lys Asn Ser Arg Leu Ile Val
        195                 200                 205

Cys Lys Gln Lys Met Pro Ile Arg Arg Arg Val Lys Ser Ile Phe Ile
    210                 215                 220

Pro Pro Pro Ala Gln Leu Thr Thr Gln Trp Lys Phe Gln Gln Glu Leu
225                 230                 235                 240

Cys Gln Phe Pro Leu Phe Asn Trp Ala Cys Ile Cys Ile Asp Met Asp
                245                 250                 255

Thr Pro Phe Asp Tyr Asn Gly Ala Trp Arg Asn Ala Trp Trp Leu Met
            260                 265                 270

Arg Arg Leu Gln Asn Gly Asn Met Glu Tyr Ile Glu Arg Trp Gly Arg
        275                 280                 285

Ile Pro Met Thr Gly Asp Thr Glu Leu Pro Pro Ala Asp Phe Lys
    290                 295                 300

Ala Gly Gly Val Asn Lys Asn Phe Lys Pro Thr Gly Ile Gln Arg Ile
305                 310                 315                 320

Tyr Pro Ile Val Ala Val Cys Leu Val Glu Gly Asn Lys Arg Val Val
                325                 330                 335

Lys Trp Ala Thr Val His Asn Gly Pro Ile Asp Arg Trp Arg Lys Lys
            340                 345                 350

Gln Thr Gly Thr Leu Lys Leu Ser Asn Leu Arg Gly Leu Val Leu Arg
        355                 360                 365

Val Cys Ser Glu Ser Glu Thr Tyr Tyr Lys Trp Thr Gly Ser Glu Phe
    370                 375                 380

Thr Gly Ala Phe Gln Gln Asp Trp Trp Pro Val Gly Gly Thr Glu Tyr
385                 390                 395                 400

Pro Leu Cys Thr Ile Lys Met Asp Pro Glu Tyr Glu Asn Pro Thr Val
                405                 410                 415

Glu Val Trp Ser Trp Lys Ala Asn Ile Pro Thr Ser Gly Thr Leu Lys
            420                 425                 430

Asp Tyr Phe Gly Leu Ser Thr Gly Gln Gln Trp Lys Asp Thr Asp Phe
        435                 440                 445

Ala Arg Leu Gln Leu Pro Arg Ser Ser His Asn Val Asp Phe Gly His
450                 455                 460

Lys Ala Arg Phe Gly Pro Phe Cys Val Lys Lys Pro Pro Val Glu Phe
465                 470                 475                 480

Arg Asp Thr Ala Pro Asn Pro Leu Asn Ile Trp Val Lys Tyr Thr Phe
            485                 490                 495

Tyr Phe Gln Phe Gly Met Tyr Gln Pro Thr Gly Ile Gln Asp
            500                 505                 510

Pro Cys Thr Ser Asn Pro Thr Tyr Pro Val Arg Met Val Gly Ala Val
            515                 520                 525

Thr His Pro Lys Tyr Ala Gly Gln Gly Gly Ile Thr Thr Gln Ile Gly
            530                 535                 540

Asp Gln Gly Ile Thr Ala Ala Ser Ile Arg Ala Ile Ser Ala Ala Pro
545                 550                 555                 560

Pro Asp Thr Tyr Thr Gln Ser Ala Phe Leu Lys Ala Pro Glu Thr Glu
            565                 570                 575

Lys Glu Glu Arg Glu Ser Glu Thr Ser Phe Thr Ser Ala Glu Ser
            580                 585                 590

Ser Ser Glu Gly Asp Gly Ser Ser Asp Asp Gln Ala Glu Arg Arg Ala
            595                 600                 605

Ala Arg Lys Arg Val Ile Lys Leu Leu Leu Lys Arg Leu Ala Asp Arg
610                 615                 620

Pro Val Asp Asn Lys Arg Arg Phe Ser Glu
625                 630                 635

<210> SEQ ID NO 14
<211> LENGTH: 639
<212> TYPE: PRT
<213> ORGANISM: Torque teno virus

<400> SEQUENCE: 14

Met Ala Pro Thr Arg Arg Trp Arg Arg Phe Gly Arg Arg Arg
1               5                   10                  15

Arg Tyr Arg Lys Arg Arg Tyr Gly Trp Arg Arg Tyr Tyr Arg Tyr
                20                  25                  30

Arg Pro Arg Tyr Tyr Arg Arg Trp Leu Val Arg Arg Arg Arg
            35                  40                  45

Ser Val Tyr Arg Gly Gly Arg Arg Ala Arg Pro Tyr Arg Ile Ser
50                  55                  60

Ala Phe Asn Pro Lys Val Met Arg Arg Val Val Ile Arg Gly Trp Trp
65                  70                  75                  80

Pro Ile Leu Gln Cys Leu Lys Gly Gln Glu Ser Leu Arg Tyr Arg Pro
                85                  90                  95

Leu Gln Trp Asp Thr Glu Lys Gln Trp Arg Val Lys Lys Asp Tyr Glu
            100                 105                 110

Asp Asn Tyr Gly Tyr Leu Val Gln Tyr Gly Gly Gly Trp Ser Gly
            115                 120                 125

Glu Val Thr Leu Glu Gly Leu Tyr Gln Glu His Leu Leu Trp Arg Asn
130                 135                 140

Ser Trp Ser Lys Gly Asn Asp Gly Met Asp Leu Val Arg Tyr Phe Gly
145                 150                 155                 160

Cys Ile Val Tyr Leu Tyr Pro Leu Gln Asp Gln Asp Tyr Trp Phe Trp
                165                 170                 175

Trp Asp Thr Asp Phe Lys Glu Leu Tyr Ala Glu Ser Ile Lys Glu Tyr
            180                 185                 190

```
Ser Gln Pro Ser Val Met Met Ala Lys Arg Thr Arg Leu Val Ile
            195                 200                 205

Ala Arg Asp Arg Ala Pro His Arg Arg Val Arg Lys Ile Phe Ile
    210                 215                 220

Pro Pro Pro Ser Arg Asp Thr Thr Gln Trp Gln Phe Gln Thr Asp Phe
225                 230                 235                 240

Cys Lys Arg Pro Leu Phe Thr Trp Ala Ala Gly Leu Ile Asp Met Gln
                245                 250                 255

Lys Pro Phe Asp Ala Asn Gly Ala Phe Arg Asn Ala Trp Trp Leu Glu
            260                 265                 270

Thr Arg Asn Asp Gln Gly Glu Met Lys Tyr Ile Glu Leu Trp Gly Arg
        275                 280                 285

Val Pro Pro Gln Gly Asp Thr Glu Leu Pro Lys Gln Ser Glu Phe Lys
    290                 295                 300

Lys Gly Asp Asn Asn Pro Asn Tyr Asn Ile Thr Glu Gly His Glu Lys
305                 310                 315                 320

Asn Ile Tyr Pro Ile Ile Tyr Val Asp Gln Lys Asp Gln Lys Thr
                325                 330                 335

Arg Lys Lys Tyr Cys Val Cys Tyr Asn Lys Thr Leu Asn Arg Trp Arg
                340                 345                 350

Lys Ala Gln Ala Ser Thr Leu Ala Ile Gly Asp Leu Gln Gly Leu Val
            355                 360                 365

Leu Arg Gln Leu Met Asn Gln Glu Met Thr Tyr Tyr Trp Lys Ser Gly
        370                 375                 380

Glu Phe Ser Ser Pro Phe Leu Gln Arg Trp Lys Gly Thr Arg Leu Ile
385                 390                 395                 400

Thr Ile Asp Ala Arg Lys Ala Asp Thr Glu Asn Pro Lys Val Ser Ser
                405                 410                 415

Trp Glu Trp Gly Gln Asn Trp Asn Thr Ser Gly Thr Val Leu Gln Glu
            420                 425                 430

Val Phe Asn Ile Ser Leu Asn Asn Thr Gln Ile Arg Gln Asp Asp Phe
        435                 440                 445

Ala Lys Leu Thr Leu Pro Lys Ser Pro His Asp Ile Asp Phe Gly His
    450                 455                 460

His Ser Arg Phe Gly Pro Phe Cys Val Lys Asn Glu Pro Leu Glu Phe
465                 470                 475                 480

Gln Leu Leu Pro Pro Thr Pro Thr Asn Leu Trp Phe Gln Tyr Lys Phe
                485                 490                 495

Leu Phe Gln Phe Gly Gly Glu Tyr Gln Pro Pro Thr Gly Ile Arg Asp
            500                 505                 510

Pro Cys Ile Asp Thr Pro Ala Tyr Pro Val Pro Gln Ser Gly Ser Val
        515                 520                 525

Thr His Pro Lys Phe Ala Gly Lys Gly Gly Met Leu Thr Glu Thr Asp
    530                 535                 540

Arg Trp Gly Ile Thr Ala Ala Ser Ser Arg Thr Leu Ser Ala Asp Thr
545                 550                 555                 560

Pro Thr Glu Ala Ala Gln Ser Ala Leu Leu Arg Gly Asp Ala Glu Lys
                565                 570                 575

Lys Gly Glu Glu Thr Glu Glu Thr Ala Ser Ser Ser Ile Thr Ser
            580                 585                 590

Ala Glu Ser Ser Thr Glu Gly Asp Gly Ser Ser Asp Glu Glu Thr
        595                 600                 605
```

Ile Arg Arg Arg Arg Thr Trp Lys Arg Leu Arg Met Val Arg
610             615                 620

Gln Gln Leu Asp Arg Arg Met Asp His Lys Arg Gln Arg Leu His
625             630                 635

<210> SEQ ID NO 15
<211> LENGTH: 625
<212> TYPE: PRT
<213> ORGANISM: Torque teno virus

<400> SEQUENCE: 15

Met Pro Tyr Arg Arg Tyr Arg Arg Arg Arg Pro Thr Arg Arg
1               5                   10                  15

Trp Arg His Arg Arg Trp Arg Arg Tyr Phe Arg Tyr Tyr Arg Arg
                20                  25                  30

Ala Pro Arg Arg Arg Pro Lys Val Arg Arg Arg Arg Lys Ala
            35                  40                  45

Pro Val Ile Gln Trp Phe Pro Pro Ser Arg Arg Thr Cys Leu Ile Glu
50                  55                  60

Gly Phe Trp Pro Leu Ser Tyr Gly His Trp Phe Arg Thr Cys Leu Pro
65                  70                  75                  80

Met Arg Arg Leu Asn Gly Leu Ile Phe Thr Gly Gly Cys Asp Trp
                85                  90                  95

Thr Gln Trp Ser Leu Gln Asn Leu Phe His Glu Lys Leu Asn Trp Arg
                100                 105                 110

Asn Ile Trp Thr Ala Ser Asn Val Gly Met Glu Phe Ala Arg Phe Leu
            115                 120                 125

Arg Gly Lys Phe Tyr Phe Phe Arg His Pro Trp Arg Ser Tyr Ile Val
130                 135                 140

Thr Trp Asp Gln Asp Ile Pro Cys Lys Pro Leu Pro Tyr Gln Asn Leu
145                 150                 155                 160

Gln Pro Leu Leu Met Leu Leu Lys Lys Gln His Lys Leu Val Leu Ser
                165                 170                 175

Gln Lys Asp Cys Asn Pro Asn Arg Lys Gln Lys Pro Val Thr Leu Lys
            180                 185                 190

Phe Arg Pro Pro Lys Leu Thr Ser Gln Trp Arg Leu Ser Arg Glu
        195                 200                 205

Leu Ser Lys Ile Pro Leu Ile Arg Leu Gly Ile Ser Leu Ile Asp Leu
        210                 215                 220

Ser Glu Pro Trp Leu Glu Gly Trp Gly Asn Ala Phe Tyr Ser Val Leu
225                 230                 235                 240

Gly Tyr Glu Ala Ser Lys His Ser Gly Arg Trp Ser Asn Trp Thr Gln
                245                 250                 255

Met Lys Tyr Phe Trp Ile Tyr Asp Thr Gly Val Gly Asn Ala Val Tyr
            260                 265                 270

Val Ile Leu Leu Lys Lys Asp Val Ser Asp Asn Pro Gly Asp Met Ala
        275                 280                 285

Thr Gln Phe Val Thr Gly Ser Gly Gln His Pro Asp Ala Ile Asp His
    290                 295                 300

Ile Glu Met Val Asn Glu Gly Trp Pro Tyr Trp Leu Phe Phe Tyr Gly
305                 310                 315                 320

Gln Ser Glu Gln Asp Ile Lys Lys Leu Ala His Asp Gln Asp Ile Val
                325                 330                 335

Arg Glu Tyr Ala Arg Asp Pro Lys Ser Lys Lys Leu Lys Ile Gly Val
            340                 345                 350

-continued

Ile Gly Trp Ala Ser Ser Asn Tyr Thr Thr Ala Gly Ser Asn Gln Asn
        355                 360                 365

Ser Val Leu Gln Thr Pro Glu Ala Ile Gln Gly Gly Tyr Val Ala Tyr
    370                 375                 380

Ala Gly Ser Arg Ile Pro Gly Ala Gly Ser Ile Thr Asn Leu Phe Gln
385                 390                 395                 400

Met Gly Trp Pro Gly Asp Gln Asn Trp Pro Pro Thr Asn Gln Asp Gln
                405                 410                 415

Thr Asn Phe Asn Trp Gly Leu Arg Gly Leu Cys Val Leu Arg Asp Asn
            420                 425                 430

Met Lys Leu Gly Ala Gln Glu Leu Asp Asp Glu Cys Thr Met Leu Ser
        435                 440                 445

Leu Phe Gly Pro Phe Val Glu Lys Ala Asn Thr Ala Phe Ala Thr Asn
    450                 455                 460

Asp Pro Lys Tyr Phe Arg Pro Glu Leu Lys Asp Tyr Asn Val Val Met
465                 470                 475                 480

Lys Tyr Ala Phe Lys Phe Gln Trp Gly Gly His Gly Thr Glu Arg Phe
                485                 490                 495

Lys Thr Thr Ile Gly Asp Pro Ser Thr Ile Pro Cys Pro Phe Glu Pro
            500                 505                 510

Gly Glu Arg Tyr His His Gly Val Gln Asp Pro Ala Lys Val Gln Asn
        515                 520                 525

Thr Val Leu Asn Pro Trp Asp Tyr Asp Cys Asp Gly Ile Val Arg Thr
    530                 535                 540

Asp Thr Leu Lys Arg Leu Leu Glu Leu Pro Thr Glu Thr Glu Glu Thr
545                 550                 555                 560

Glu Lys Ala Tyr Pro Leu Leu Gly Gln Lys Thr Glu Lys Glu Pro Leu
                565                 570                 575

Ser Asp Ser Asp Glu Glu Ser Val Ile Ser Ser Thr Ser Ser Gly Ser
            580                 585                 590

Ser Gln Glu Glu Glu Thr Gln Arg Arg Lys His His Lys Pro Ser Lys
        595                 600                 605

Arg Arg Leu Leu Lys His Leu Gln Arg Val Val Lys Arg Met Lys Thr
    610                 615                 620

Leu
625

<210> SEQ ID NO 16
<211> LENGTH: 625
<212> TYPE: PRT
<213> ORGANISM: Torque teno virus

<400> SEQUENCE: 16

Met Pro Tyr Arg Arg Tyr Arg Arg Arg Arg Pro Thr Arg Arg
1               5                   10                  15

Trp Arg His Arg Arg Trp Arg Arg Phe Phe Arg Tyr Tyr Arg Arg
                20                  25                  30

Ala Pro Arg Arg Arg Thr Lys Val Arg Arg Arg Arg Lys Ala
            35                  40                  45

Pro Val Ile Gln Trp Phe Pro Pro Ser Arg Arg Thr Cys Leu Ile Glu
        50                  55                  60

Gly Phe Trp Pro Leu Ser Tyr Gly His Trp Phe Arg Thr Cys Leu Pro
65                  70                  75                  80

Met Arg Arg Leu Asn Gly Leu Ile Phe Thr Gly Gly Gly Cys Asp Trp

```
                      85                  90                  95
Thr Gln Trp Ser Leu Gln Asn Leu Tyr His Glu Lys Leu Asn Trp Arg
                100                 105                 110

Asn Ile Trp Thr Ala Ser Asn Val Gly Met Glu Phe Ala Arg Phe Leu
            115                 120                 125

Arg Gly Lys Phe Tyr Phe Phe Arg His Pro Trp Arg Ser Tyr Ile Ile
        130                 135                 140

Thr Trp Asp Gln Asp Ile Pro Cys Lys Pro Leu Pro Tyr Gln Asn Leu
145                 150                 155                 160

His Pro Leu Leu Met Leu Leu Lys Lys Gln His Lys Leu Val Leu Ser
                165                 170                 175

Gln Lys Asp Cys Asn Pro Asn Arg Arg Gln Lys Pro Val Thr Leu Lys
            180                 185                 190

Ile Arg Pro Pro Lys Leu Thr Ser Gln Trp Arg Leu Ser Arg Glu
        195                 200                 205

Leu Ala Lys Met Pro Leu Val Arg Leu Gly Val Ser Leu Ile Asp Leu
        210                 215                 220

Ser Glu Pro Trp Leu Glu Gly Trp Gly Asn Ala Phe Tyr Ser Val Leu
225                 230                 235                 240

Gly Tyr Glu Ala Ser Lys His Ser Gly Arg Trp Ser Asn Trp Thr Gln
                245                 250                 255

Ile Lys Tyr Phe Trp Ile Tyr Asp Thr Gly Val Gly Asn Ala Val Tyr
            260                 265                 270

Val Ile Leu Leu Lys Gln Glu Val Asp Asp Asn Pro Gly Ala Met Ala
        275                 280                 285

Thr Lys Phe Val Thr Gly Pro Gly Gln His Pro Asp Ala Ile Asp Arg
        290                 295                 300

Ile Glu Gln Ile Asn Glu Gly Trp Pro Tyr Trp Leu Phe Phe Tyr Gly
305                 310                 315                 320

Gln Ser Glu Gln Asp Ile Lys Lys Leu Ala His Asp Gln Glu Ile Ala
                325                 330                 335

Arg Glu Tyr Ala Asn Asn Pro Lys Ser Lys Lys Leu Lys Ile Gly Val
            340                 345                 350

Ile Gly Trp Ala Ser Ser Asn Phe Thr Thr Ala Gly Ser Ser Gln Asn
        355                 360                 365

Gln Thr Pro Gln Thr Pro Glu Ala Ile Gln Gly Gly Tyr Val Ala Tyr
        370                 375                 380

Ala Gly Ser Lys Ile Gln Gly Ala Gly Ala Ile Thr Asn Leu Tyr Thr
385                 390                 395                 400

Asp Ala Trp Pro Gly Asp Gln Asn Trp Pro Pro Leu Asn Arg Glu Gln
                405                 410                 415

Thr Asn Phe Asn Trp Gly Leu Arg Gly Leu Cys Ile Met Arg Asp Asn
            420                 425                 430

Met Lys Leu Gly Ala Gln Glu Leu Asp Asp Glu Cys Thr Met Leu Thr
        435                 440                 445

Leu Phe Gly Pro Phe Val Glu Lys Ala Asn Thr Ala Phe Ala Thr Asn
        450                 455                 460

Asp Pro Lys Tyr Phe Arg Pro Glu Leu Lys Asp Tyr Asn Ile Val Met
465                 470                 475                 480

Lys Tyr Ala Phe Lys Phe Gln Trp Gly Gly His Gly Thr Glu Arg Phe
                485                 490                 495

Lys Thr Thr Ile Gly Asp Pro Ser Thr Ile Pro Cys Pro Phe Glu Pro
            500                 505                 510
```

Gly Glu Arg Tyr His His Gly Val Gln Asp Pro Ala Lys Val Gln Asn
            515                 520                 525

Thr Val Leu Asn Pro Trp Asp Tyr Asp Cys Asp Gly Ile Val Arg Thr
    530                 535                 540

Asp Thr Leu Lys Arg Leu Leu Glu Leu Pro Thr Glu Thr Glu Thr
545                 550                 555                 560

Glu Lys Ala Tyr Pro Leu Leu Gly Gln Lys Thr Glu Lys Glu Pro Leu
                565                 570                 575

Ser Asp Ser Asp Glu Glu Ser Val Ile Ser Ser Thr Ser Ser Gly Ser
            580                 585                 590

Ser Gln Glu Glu Glu Thr Gln Arg Arg Gln His Lys Pro Ser Lys
            595                 600                 605

Arg Arg Leu Leu Lys His Leu Gln Arg Val Val Lys Arg Met Lys Thr
    610                 615                 620

Leu
625

<210> SEQ ID NO 17
<211> LENGTH: 73
<212> TYPE: PRT
<213> ORGANISM: Torque teno virus

<400> SEQUENCE: 17

Met Lys Glu Lys Asp Tyr Trp Glu Glu Ala Trp Leu Thr Ser Cys Thr
1               5                   10                  15

Ser Ile His Asp His His Cys Asn Cys Gly Ser Trp Arg Asp His Leu
            20                  25                  30

Trp Thr Leu Cys Ala Leu Asp Asp Ala Asp Leu Ala Ala Ala Ala Asp
        35                  40                  45

Ile Ile Glu Arg Glu Glu Ala Asp Gly Gly Glu Asp Phe Gly Phe Val
    50                  55                  60

Asp Gly Asp Pro Gly Asp Ala Gly Gly
65                  70

<210> SEQ ID NO 18
<211> LENGTH: 72
<212> TYPE: PRT
<213> ORGANISM: Torque teno virus

<400> SEQUENCE: 18

Met Pro Glu His Trp Glu Glu Ala Trp Leu Glu Ala Thr Lys Gly Trp
1               5                   10                  15

His Asp Leu Asp Cys Arg Cys Gly Asn Trp Gln Asp His Leu Trp Leu
            20                  25                  30

Leu Leu Ala Asp Gly Asp Ala Ala Leu Ala Ala Ala Val Asp Ala Ile
        35                  40                  45

Glu Arg Asp Ala Met Gly Gly Glu Asp Val Thr Thr Ala Thr Asp Arg
    50                  55                  60

Val Thr Ile Gly Asp Asp Gly Trp
65                  70

<210> SEQ ID NO 19
<211> LENGTH: 68
<212> TYPE: PRT
<213> ORGANISM: Torque teno virus

<400> SEQUENCE: 19

Met Glu Glu Arg Trp Leu Thr Val Ala Tyr Cys Ala His Gly Leu Phe
1               5                   10                  15

Cys Asp Cys Lys Asn Pro Lys Lys His Leu Glu Lys Cys Leu Thr Asp
                20                  25                  30

Ala Ile Ala Asp Ala Glu Gly Asp Arg His Gly Asp Gly Gly Thr Gly
            35                  40                  45

Gly Gly Asp Ala Thr Phe Asp Ile Gly Ile Asp Ala Leu Leu Ala Ala
    50                  55                  60

Ala Ala Gln Arg
65

<210> SEQ ID NO 20
<211> LENGTH: 68
<212> TYPE: PRT
<213> ORGANISM: Torque teno virus

<400> SEQUENCE: 20

Met Glu Glu Arg Trp Leu Thr Val Ala Tyr Cys Ala His Gly Leu Phe
1               5                   10                  15

Cys Gly Cys Lys Asp Pro Lys Lys His Leu Glu Lys Cys Leu Thr Asp
                20                  25                  30

Ala Ile Ala Asp Ala Glu Gly Asp Arg His Gly Asp Gly Gly Thr Gly
            35                  40                  45

Gly Gly Asp Ala Ser Phe Asp Ile Gly Ile Asp Ala Leu Leu Ala Ala
    50                  55                  60

Ala Ala Gln Arg
65

<210> SEQ ID NO 21
<211> LENGTH: 174
<212> TYPE: PRT
<213> ORGANISM: Torque teno virus

<400> SEQUENCE: 21

Met Arg Phe Arg Arg Arg Arg Phe Gly Arg Arg Arg Arg Tyr Tyr Arg
1               5                   10                  15

Lys Arg Arg Gly Gly Trp Arg Arg Phe Arg Ile Arg Arg Arg
                20                  25                  30

Pro Trp Arg Arg Trp Arg Phe Gly Gly Met Tyr Gln Pro Pro Thr Gly
            35                  40                  45

Ile Gln Asp Pro Cys Thr Ser Asn Pro Thr Tyr Pro Val Arg Met Val
    50                  55                  60

Gly Ala Val Thr His Pro Lys Tyr Ala Gly Gln Gly Ile Thr Thr
65                  70                  75                  80

Gln Ile Gly Asp Gln Gly Ile Thr Ala Ala Ser Ile Arg Ala Ile Ser
                85                  90                  95

Ala Ala Pro Pro Asp Thr Tyr Thr Gln Ser Ala Phe Leu Lys Ala Pro
            100                 105                 110

Glu Thr Glu Lys Glu Glu Glu Arg Glu Ser Glu Thr Ser Phe Thr Ser
        115                 120                 125

Ala Glu Ser Ser Ser Glu Gly Asp Gly Ser Ser Asp Asp Gln Ala Glu
    130                 135                 140

Arg Arg Ala Ala Arg Lys Arg Val Ile Lys Leu Leu Leu Lys Arg Leu
145                 150                 155                 160

Ala Asp Arg Pro Val Asp Asn Lys Arg Arg Phe Ser Glu
                165                 170

<210> SEQ ID NO 22
<211> LENGTH: 182
<212> TYPE: PRT
<213> ORGANISM: Torque teno virus

<400> SEQUENCE: 22

```
Met Ala Pro Thr Arg Arg Trp Arg Arg Arg Phe Gly Arg Arg Arg Arg
1               5                   10                  15

Arg Tyr Arg Lys Arg Arg Tyr Gly Trp Arg Arg Tyr Tyr Arg Tyr
            20                  25                  30

Arg Pro Arg Tyr Tyr Arg Arg Trp Leu Phe Gly Gly Glu Tyr Gln
        35                  40                  45

Pro Pro Thr Gly Ile Arg Asp Pro Cys Ile Asp Thr Pro Ala Tyr Pro
50                  55                  60

Val Pro Gln Ser Gly Ser Val Thr His Pro Lys Phe Ala Gly Lys Gly
65                  70                  75                  80

Gly Met Leu Thr Glu Thr Asp Arg Trp Gly Ile Thr Ala Ala Ser Ser
                85                  90                  95

Arg Thr Leu Ser Ala Asp Thr Pro Thr Glu Ala Ala Gln Ser Ala Leu
            100                 105                 110

Leu Arg Gly Asp Ala Glu Lys Lys Gly Glu Thr Glu Glu Thr Ala
        115                 120                 125

Ser Ser Ser Ser Ile Thr Ser Ala Glu Ser Ser Thr Glu Gly Asp Gly
130                 135                 140

Ser Ser Asp Asp Glu Glu Thr Ile Arg Arg Arg Arg Thr Trp Lys
145                 150                 155                 160

Arg Leu Arg Arg Met Val Arg Gln Gln Leu Asp Arg Arg Met Asp His
                165                 170                 175

Lys Arg Gln Arg Leu His
            180
```

<210> SEQ ID NO 23
<211> LENGTH: 178
<212> TYPE: PRT
<213> ORGANISM: Torque teno virus

<400> SEQUENCE: 23

```
Met Pro Tyr Arg Arg Tyr Arg Arg Arg Arg Arg Pro Thr Arg Arg
1               5                   10                  15

Trp Arg His Arg Arg Trp Arg Arg Tyr Phe Arg Tyr Arg Tyr Arg Arg
            20                  25                  30

Ala Pro Arg Arg Arg Pro Lys Trp Gly Gly His Gly Thr Glu Arg
        35                  40                  45

Phe Lys Thr Thr Ile Gly Asp Pro Ser Thr Ile Pro Cys Pro Phe Glu
50                  55                  60

Pro Gly Glu Arg Tyr His His Gly Val Gln Asp Pro Ala Lys Val Gln
65                  70                  75                  80

Asn Thr Val Leu Asn Pro Trp Asp Tyr Asp Cys Asp Gly Ile Val Arg
                85                  90                  95

Thr Asp Thr Leu Lys Arg Leu Leu Glu Leu Pro Thr Glu Thr Glu Glu
            100                 105                 110

Thr Glu Lys Ala Tyr Pro Leu Leu Gly Gln Lys Thr Glu Lys Glu Pro
        115                 120                 125

Leu Ser Asp Ser Asp Glu Glu Ser Val Ile Ser Ser Thr Ser Ser Gly
        130                 135                 140
```

Ser Ser Gln Glu Glu Glu Thr Gln Arg Arg Lys His His Lys Pro Ser
145                 150                 155                 160

Lys Arg Arg Leu Leu Lys His Leu Gln Arg Val Val Lys Arg Met Lys
                165                 170                 175

Thr Leu

<210> SEQ ID NO 24
<211> LENGTH: 178
<212> TYPE: PRT
<213> ORGANISM: Torque teno virus

<400> SEQUENCE: 24

Met Pro Tyr Arg Arg Tyr Arg Arg Arg Arg Pro Thr Arg Arg
1               5                   10                  15

Trp Arg His Arg Arg Trp Arg Arg Phe Phe Arg Tyr Arg Tyr Arg Arg
                20                  25                  30

Ala Pro Arg Arg Arg Arg Thr Lys Trp Gly Gly His Gly Thr Glu Arg
                35                  40                  45

Phe Lys Thr Thr Ile Gly Asp Pro Ser Thr Ile Pro Cys Pro Phe Glu
            50                  55                  60

Pro Gly Glu Arg Tyr His His Gly Val Gln Asp Pro Ala Lys Val Gln
65                  70                  75                  80

Asn Thr Val Leu Asn Pro Trp Asp Tyr Asp Cys Asp Gly Ile Val Arg
                85                  90                  95

Thr Asp Thr Leu Lys Arg Leu Leu Glu Leu Pro Thr Glu Thr Glu Glu
            100                 105                 110

Thr Glu Lys Ala Tyr Pro Leu Leu Gly Gln Lys Thr Glu Lys Glu Pro
        115                 120                 125

Leu Ser Asp Ser Asp Glu Glu Ser Val Ile Ser Ser Thr Ser Ser Gly
130                 135                 140

Ser Ser Gln Glu Glu Glu Thr Gln Arg Arg Arg Gln His Lys Pro Ser
145                 150                 155                 160

Lys Arg Arg Leu Leu Lys His Leu Gln Arg Val Val Lys Arg Met Lys
                165                 170                 175

Thr Leu

<210> SEQ ID NO 25
<211> LENGTH: 224
<212> TYPE: PRT
<213> ORGANISM: Torque teno virus

<400> SEQUENCE: 25

Met Lys Glu Lys Asp Tyr Trp Glu Glu Ala Trp Leu Thr Ser Cys Thr
1               5                   10                  15

Ser Ile His Asp His His Cys Asn Cys Gly Ser Trp Arg Asp His Leu
                20                  25                  30

Trp Thr Leu Cys Ala Leu Asp Asp Ala Asp Leu Ala Ala Ala Ala Asp
            35                  40                  45

Ile Ile Glu Arg Glu Glu Ala Asp Gly Gly Glu Asp Phe Gly Phe Val
        50                  55                  60

Asp Gly Asp Pro Gly Asp Ala Gly Gly Ser Ala Ala Cys Thr Ser Leu
65                  70                  75                  80

Pro Pro Glu Ser Lys Ile Pro Ala Leu Leu Thr Arg Pro Ile Leu Ser
                85                  90                  95

Glu Trp Ser Glu Gln Leu His Thr Pro Asn Thr Pro Gly Lys Ala Glu
            100                 105                 110

Ser Arg Pro Lys Leu Glu Ile Lys Val Ser Pro Leu Pro Leu Ser Val
        115                 120                 125

Pro Ser Val Gln Leu His Gln Ile Pro Thr Arg Ser Arg Arg Ser Ser
    130                 135                 140

Lys Pro Arg Lys Pro Arg Lys Lys Arg Lys Glu Arg Val Arg Pro Val
145                 150                 155                 160

Ser Arg Val Pro Lys Ala Leu Leu Arg Glu Met Asp Arg Leu Met Thr
                165                 170                 175

Lys Gln Arg Asp Ala Leu Pro Glu Ser Glu Ser Ser Tyr Phe Ser
            180                 185                 190

Ser Asp Ser Leu Thr Asp Pro Trp Thr Ser Asp Asp Phe Gln
    195                 200                 205

Ser Asp Pro Asp Pro Leu Thr Asn Lys Arg Lys Lys Arg Leu Gln Phe
    210                 215                 220

<210> SEQ ID NO 26
<211> LENGTH: 228
<212> TYPE: PRT
<213> ORGANISM: Torque teno virus

<400> SEQUENCE: 26

Met Pro Glu His Trp Glu Glu Ala Trp Leu Glu Ala Thr Lys Gly Trp
1               5                   10                  15

His Asp Leu Asp Cys Arg Cys Gly Asn Trp Gln Asp His Leu Trp Leu
                20                  25                  30

Leu Leu Ala Asp Gly Asp Ala Ala Leu Ala Ala Val Asp Ala Ile
            35                  40                  45

Glu Arg Asp Ala Met Gly Gly Glu Asp Val Thr Thr Ala Thr Asp Arg
50                  55                  60

Val Thr Ile Gly Asp Asp Gly Cys Leu Ala Val Asn Thr Ser His Gln
65                  70                  75                  80

Gln Val Ser Ala Ile Pro Ala Leu Ile His Gln Pro Ile Leu Cys Arg
                85                  90                  95

Ser Gln Glu Val Leu His Thr Pro Asn Ser Pro Glu Arg Ala Glu Cys
            100                 105                 110

Ser Arg Lys Gln Thr Val Gly Val Ser Leu Leu Pro Leu Pro Glu Pro
        115                 120                 125

Ser Val Gln Ile His Pro Pro Lys Gln Arg Lys Val His Phe Ser Glu
    130                 135                 140

Gly Thr Arg Lys Arg Lys Glu Arg Lys Pro Arg Lys Pro Arg His Arg
145                 150                 155                 160

Pro Val Ser Arg Val Pro Lys Ala Leu Leu Arg Glu Met Asp Arg Leu
                165                 170                 175

Met Met Lys Arg Gln Ser Asp Ala Glu Gly Gly Pro Gly Ser Asp Ser
            180                 185                 190

Asp Gly Trp Ser Asp Ser Ser Leu Thr Asp Glu Trp Thr Thr Ser Asp
        195                 200                 205

Ser Asp Phe Ile Asp Thr Pro Ile Arg Glu Arg Cys Leu Asn Lys Lys
    210                 215                 220

Gln Lys Lys Arg
225

<210> SEQ ID NO 27
<211> LENGTH: 199
<212> TYPE: PRT

<213> ORGANISM: Torque teno virus

<400> SEQUENCE: 27

Met Glu Glu Arg Trp Leu Thr Val Ala Tyr Cys Ala His Gly Leu Phe
1               5                   10                  15

Cys Asp Cys Lys Asn Pro Lys Lys His Leu Glu Lys Cys Leu Thr Asp
            20                  25                  30

Ala Ile Ala Asp Ala Glu Gly Asp Arg His Gly Asp Gly Gly Thr Gly
        35                  40                  45

Gly Gly Asp Ala Thr Phe Asp Ile Gly Ile Asp Ala Leu Leu Ala Ala
    50                  55                  60

Ala Ala Gln Ser Gly Glu Asp Met Ala Pro Lys Asp Leu Lys Gln Pro
65                  70                  75                  80

Ser Glu Ile Pro Ala Pro Tyr His Val Pro Leu Asn Pro Gly Asn Gly
                85                  90                  95

Thr Thr Thr Gly Tyr Lys Thr Pro Pro Arg Tyr Lys Thr Gln Ser Ser
            100                 105                 110

Thr Leu Gly Thr Met Thr Val Thr Gly Leu Leu Glu Gln Ile Leu Ser
        115                 120                 125

Lys Asp Phe Ser Asn Ser Pro Gln Arg Arg Arg Arg Arg Arg Arg Arg
    130                 135                 140

Thr His Ser Leu Asp Lys Lys Gln Arg Lys Ser His Tyr Gln Thr Pro
145                 150                 155                 160

Thr Lys Arg Ala Leu Ser Gln Ala Arg Ala Val Asp Pro Leu Lys Lys
                165                 170                 175

Lys Arg Arg Arg Asp Glu Ser Thr Thr Ser Gln Ala Ser Asp Asp Ser
            180                 185                 190

Ser Ser Thr Ser Ser Gly Trp
        195

<210> SEQ ID NO 28
<211> LENGTH: 199
<212> TYPE: PRT
<213> ORGANISM: Torque teno virus

<400> SEQUENCE: 28

Met Glu Glu Arg Trp Leu Thr Val Ala Tyr Cys Ala His Gly Leu Phe
1               5                   10                  15

Cys Gly Cys Lys Asp Pro Lys Lys His Leu Glu Lys Cys Leu Thr Asp
            20                  25                  30

Ala Ile Ala Asp Ala Glu Gly Asp Arg His Gly Asp Gly Gly Thr Gly
        35                  40                  45

Gly Gly Asp Ala Ser Phe Asp Ile Gly Ile Asp Ala Leu Leu Ala Ala
    50                  55                  60

Ala Ala Gln Ser Gly Glu Ala Thr Glu Pro Lys Asp Ser Lys Gln Pro
65                  70                  75                  80

Ser Glu Ile Pro Ala Pro Tyr His Val Pro Leu Asn Pro Gly Asn Gly
                85                  90                  95

Thr Thr Thr Gly Tyr Lys Thr Pro Pro Arg Tyr Lys Thr Gln Ser Ser
            100                 105                 110

Thr Leu Gly Thr Met Thr Val Thr Gly Leu Leu Glu Gln Ile Leu Ser
        115                 120                 125

Lys Asp Phe Ser Asn Ser Pro Gln Arg Arg Arg Arg Arg Arg Arg Arg
    130                 135                 140

Thr His Ser Leu Asp Lys Lys Gln Arg Lys Ser His Tyr Gln Thr Pro 145                 150                 155                 160
Thr Lys Arg Ala Leu Ser Gln Ala Arg Ala Val Asp Pro Leu Lys Lys
                165                 170                 175

Lys Arg Arg Arg Glu Glu Asp Ser Thr Ser Gln Ala Ser Asp Asp Ser
        180                 185                 190

Ser Ser Thr Ser Ser Gly Trp
        195

<210> SEQ ID NO 29
<211> LENGTH: 21
<212> TYPE: DNA
<213> ORGANISM: Torque teno virus

<400> SEQUENCE: 29
tccgaatggc tgagtttatg c                                         21

<210> SEQ ID NO 30
<211> LENGTH: 17
<212> TYPE: DNA
<213> ORGANISM: Torque teno virus

<400> SEQUENCE: 30
tccgctcagc tgctcct                                              17

<210> SEQ ID NO 31
<211> LENGTH: 18
<212> TYPE: DNA
<213> ORGANISM: Torque teno virus

<400> SEQUENCE: 31
ggtggtaaag aggatgaa                                             18

<210> SEQ ID NO 32
<211> LENGTH: 19
<212> TYPE: DNA
<213> ORGANISM: Torque teno virus

<400> SEQUENCE: 32
aatagattgg acacaggag                                            19

<210> SEQ ID NO 33
<211> LENGTH: 18
<212> TYPE: DNA
<213> ORGANISM: Torque teno virus

<400> SEQUENCE: 33
tatcgggcag gagcagct                                             18

<210> SEQ ID NO 34
<211> LENGTH: 18
<212> TYPE: DNA
<213> ORGANISM: Torque teno virus

<400> SEQUENCE: 34 tagggcgcg ctctacgt                                              18

<210> SEQ ID NO 35
<211> LENGTH: 21
<212> TYPE: DNA
<213> ORGANISM: Torque teno virus

<400> SEQUENCE: 35

```
cctacatgaa ggagaaagac t                                              21

<210> SEQ ID NO 36
<211> LENGTH: 17
<212> TYPE: DNA
<213> ORGANISM: Torque teno virus

<400> SEQUENCE: 36
ccagcgtctc cagggtc                                                   17

<210> SEQ ID NO 37
<211> LENGTH: 17
<212> TYPE: DNA
<213> ORGANISM: Torque teno virus

<400> SEQUENCE: 37
aagctaccaa gggctgg                                                   17

<210> SEQ ID NO 38
<211> LENGTH: 19
<212> TYPE: DNA
<213> ORGANISM: Torque teno virus

<400> SEQUENCE: 38
gcggtctggt agcggtagt                                                 19

<210> SEQ ID NO 39
<211> LENGTH: 22
<212> TYPE: DNA
<213> ORGANISM: Torque teno virus

<400> SEQUENCE: 39
cgaatggctg agtttatgcc gc                                             22

<210> SEQ ID NO 40
<211> LENGTH: 11
<212> TYPE: DNA
<213> ORGANISM: Torque teno virus

<400> SEQUENCE: 40
agtcctcatt t                                                         11

<210> SEQ ID NO 41
<211> LENGTH: 11
<212> TYPE: DNA
<213> ORGANISM: Torque teno virus

<400> SEQUENCE: 41
aaccaatcag a                                                         11

<210> SEQ ID NO 42
<211> LENGTH: 17
<212> TYPE: DNA
<213> ORGANISM: Torque teno virus

<400> SEQUENCE: 42
ctgggcgggt gccggag                                                   17

<210> SEQ ID NO 43
<211> LENGTH: 14
<212> TYPE: DNA
<213> ORGANISM: Torque teno virus

<400> SEQUENCE: 43
```

```
cggagtcaag gggc                                                14
```

<210> SEQ ID NO 44
<211> LENGTH: 11
<212> TYPE: DNA
<213> ORGANISM: Torque teno virus

<400> SEQUENCE: 44

```
tatcgggcag g                                                   11
```

<210> SEQ ID NO 45
<211> LENGTH: 23
<212> TYPE: PRT
<213> ORGANISM: Torque teno virus

<400> SEQUENCE: 45

Thr Ala Cys Ala Cys Thr Thr Cys Cys Gly Gly Thr Thr Cys Ala
1               5                   10                  15

Gly Gly Ala Gly Gly Cys Thr
            20

<210> SEQ ID NO 46
<211> LENGTH: 22
<212> TYPE: DNA
<213> ORGANISM: Torque teno virus

<400> SEQUENCE: 46

```
actcagccat tcggaacctc ac                                       22
```

<210> SEQ ID NO 47
<211> LENGTH: 22
<212> TYPE: DNA
<213> ORGANISM: Torque teno virus

<400> SEQUENCE: 47

```
caatttggct cgcttcgctc gc                                       22
```

<210> SEQ ID NO 48
<211> LENGTH: 25
<212> TYPE: DNA
<213> ORGANISM: Torque teno virus

<400> SEQUENCE: 48

```
tacttatatt cgctttcgtg ggaac                                    25
```

<210> SEQ ID NO 49
<211> LENGTH: 22
<212> TYPE: DNA
<213> ORGANISM: Torque teno virus

<400> SEQUENCE: 49

```
agttacacat aaccaccaaa cc                                       22
```

<210> SEQ ID NO 50
<211> LENGTH: 21
<212> TYPE: DNA
<213> ORGANISM: Torque teno virus

<400> SEQUENCE: 50

```
attaccgcct gcccgatagg c                                        21
```

<210> SEQ ID NO 51

```
<211> LENGTH: 21
<212> TYPE: DNA
<213> ORGANISM: Torque teno virus

<400> SEQUENCE: 51
ccaaaccaca ggaaactgtg c                                              21

<210> SEQ ID NO 52
<211> LENGTH: 20
<212> TYPE: DNA
<213> ORGANISM: Torque teno virus

<400> SEQUENCE: 52
cttgactccg ctctcaggag                                                20

<210> SEQ ID NO 53
<211> LENGTH: 2878
<212> TYPE: DNA
<213> ORGANISM: Torque teno virus

<400> SEQUENCE: 53
tacacttccg ggttcaggag gctcaatttg gctcgcttcg ctcgcaccac gtttgctgcc      60
aggcggacct gattgaagac tgaaaaccgt taaattcaaa tttgaaaatg cgggcaaaa     120 tggcggacag ggggcgggga ttatgcaaat taatttatgc aaagtaggag gagctcgatt    180
ttaatttatg caaagtagga ggagtcattt ctgattggtc gggagctcaa gtcctcattt    240
gcatagggtg taaccaatca gatttaaggc gttcccacta aagtgaatat aagtgagtgc    300
agttccgaat ggctgagttt atgccgccag cggtagacag aactgtctag cgactgggcg    360
ggtgccggag gatcccagat ccggagtcaa ggggcctatc gggcaggagc agctgagcgg    420
agggcctaca tgaaggagaa agactactgg gaagaagcct ggctgaccag ctgtacatcc    480
atacacgacc accactgcga ctgcggtagc tggagagacc acctgtggac gctatgcgct    540
ttagacgacg cagatttggc cgccgccgca gatattatag aaagagaaga ggcggatgga    600
ggagaagatt tcggattcgt agacggcgac cctggagacg ctggcgggta aggagatggc    660
ggcgttccgt cttccgtaga aggggacgta gagcgcgccc ctaccgcatt agcgcgtgga    720
accctaaggt tctaagaaac tgccgcatca caggatggtg gccagtaata cagtgtatgg    780
acgggatgga gtggataaaa tacaagccga tggacttaag agtcgaggca aaccggatat    840
tcgataaaca gggcagtaag atagagacag aacagatggg atacttaatg cagtacggag    900
gaggatggtc aagcggagta atcagcttag agggactttt caatgaaaac agactgtgga    960
gaaacatatg gtctaaaagc aatgacggga tggacttggt cagatacttc gggtgcagaa   1020
ttagactata tccaacagag aatcagggct acttgttctg gtatgacaca gaatttgacg   1080
aacagcagag aagaatgtta gacgaatata cacaacctag tgtaatgctg caggctaaaa   1140
actcccgttt aatagtatgt aaacaaaaga tgccaattag acggagagta aagagcattt   1200
tcataccgcc accggcacag ttaacaacac agtggaagtt tcagcaggaa ctgtgtcaat   1260
ttccattatt taactgggcc tgtatctgta tagacatgga cacgccgttc gactacaacg   1320
gcgcatggcg aaatgcctgg tggctaatga gaaggcttca aaacgaaaac atggagtaca   1380
tagaaagatg gggcagaata ccgatgacag gagacacaga actgccacca gcagacgact   1440
tcaaggcagg aggggtgaac aaaaacttca aaccgacagg tattcagaga atatacccta   1500
tagtagcagt atgcctagtg gagggaaaca agagagtagt gaaatgggcc acagtacaca   1560
atgggccaat agacagatgg agaaaaaaac agacaggaac gttaaaacta tctgcactga   1620
```

-continued

```
gaagactagt gcttagagta tgctcagaaa gtgagacata ctataagtgg acagcatcag    1680
aatttacagg agcatttcag caggactggt ggccagttag cggaacagaa tacccgttat    1740
gtacaattaa aatggagcca gaattcgaaa acccgacagt agaggtgtgg tcatggaaag    1800
caactatacc gacagcagga acactgaaag actatttcgg gctcagttca gggcaacagt    1860
ggaaggacac tgactttggc aggctgcaat acccagaag cagccacaat gttgactttg     1920
gacataaagc tagatttggc ccattttgtg tgaaaaagcc tccagtagaa ttcagagact    1980
cagcccccaa cccactaaat atctgggtga atacacatt ctattttcag ttcggcggca     2040
tgtaccagcc tccaccggaa atccaagatc cctgcacttc taacccgacc tatcctgtca    2100
gaatggtcgg agcagttaca cacccccaaat acgccgggca aggcggaatc gcgacccaaa   2160
ttggagatca aggtatcacc gctgcctctc tccgtgccat cagtgcagct ccaccaaata    2220
cctacacgca gtcggcgttc ctcaaagccc cggaaaccga aaagaagag gaaagagaga     2280
gtgagaccag tttcacgagt gccgaaagct cttctgaggg agatggatcg tctgatgacc    2340
aagcagagag acgcgctgcc agaaagcgag tcatcaagct acttctcaag cgactcgctg    2400
acagacccgt ggacaacaag cgacgacgat tttcagagtg accctgaccc cctcaccaat    2460
aaacgcaaaa agcgcttgca attctaattc gctgtccgtg tattcattgg ggggtccgg     2520
ggggcttgc cccccgtta gttgggttct cgcactcccg cctgccaagt gaaagtcggg      2580
gacgagtgag tgcgggacat cccgtgtaat ggctacataa ctacccggct ttgcttcgac    2640
agtggccgtg gctcgaccct cacacaacaa tgcagatagg gggcgcaatt gggatcgtta    2700
gaaaactatg gccgagcatg ggggggctc cgcccccccc aacccccccg gtgggggggc     2760
caaggcccc cctacacccc ccatgggggg gctgctgccc cccaaacccc ccgcgtcgga     2820
tgggggggc tgcgcccccc ccaaaccccc cttgcccggg gctgtgcccc ggaccccc      2878
```

<210> SEQ ID NO 54
<211> LENGTH: 635
<212> TYPE: PRT
<213> ORGANISM: Torque teno virus

<400> SEQUENCE: 54

```
Met Arg Phe Arg Arg Arg Arg Phe Gly Arg Arg Arg Tyr Tyr Arg
1               5                   10                  15

Lys Arg Arg Gly Gly Trp Arg Arg Phe Arg Ile Arg Arg Arg
            20                  25                  30

Pro Trp Arg Arg Trp Arg Val Arg Trp Arg Arg Ser Val Phe Arg
            35                  40                  45

Arg Arg Gly Arg Arg Ala Arg Pro Tyr Arg Ile Ser Ala Trp Asn Pro
        50                  55                  60

Lys Val Leu Arg Asn Cys Arg Ile Thr Gly Trp Trp Pro Val Ile Gln
65                  70                  75                  80

Cys Met Asp Gly Met Glu Trp Ile Lys Tyr Lys Pro Met Asp Leu Arg
                85                  90                  95

Val Glu Ala Asn Arg Ile Phe Asp Lys Gln Gly Ser Lys Ile Glu Thr
            100                 105                 110

Glu Gln Met Gly Tyr Leu Met Gln Tyr Gly Gly Trp Ser Ser Gly
            115                 120                 125

Val Ile Ser Leu Glu Gly Leu Phe Asn Glu Asn Arg Leu Trp Arg Asn
        130                 135                 140

Ile Trp Ser Lys Ser Asn Asp Gly Met Asp Leu Val Arg Tyr Phe Gly
```

```
            145                 150                 155                 160
Cys Arg Ile Arg Leu Tyr Pro Thr Glu Asn Gln Gly Tyr Leu Phe Trp
                165                 170                 175

Tyr Asp Thr Glu Phe Asp Glu Gln Gln Arg Met Leu Asp Glu Tyr
        180                 185                 190

Thr Gln Pro Ser Val Met Leu Gln Ala Lys Asn Ser Arg Leu Ile Val
            195                 200                 205

Cys Lys Gln Lys Met Pro Ile Arg Arg Val Lys Ser Ile Phe Ile
    210                 215                 220

Pro Pro Pro Ala Gln Leu Thr Thr Gln Trp Lys Phe Gln Gln Glu Leu
225                 230                 235                 240

Cys Gln Phe Pro Leu Phe Asn Trp Ala Cys Ile Cys Ile Asp Met Asp
                245                 250                 255

Thr Pro Phe Asp Tyr Asn Gly Ala Trp Arg Asn Ala Trp Trp Leu Met
                260                 265                 270

Arg Arg Leu Gln Asn Gly Asn Met Glu Tyr Ile Glu Arg Trp Gly Arg
            275                 280                 285

Ile Pro Met Thr Gly Asp Thr Glu Leu Pro Pro Ala Asp Asp Phe Lys
            290                 295                 300

Ala Gly Gly Val Asn Lys Asn Phe Lys Pro Thr Gly Ile Gln Arg Ile
305                 310                 315                 320

Tyr Pro Ile Val Ala Val Cys Leu Val Glu Gly Asn Lys Arg Val Val
                325                 330                 335

Lys Trp Ala Thr Val His Asn Gly Pro Ile Asp Arg Trp Arg Lys Lys
                340                 345                 350

Gln Thr Gly Thr Leu Lys Leu Ser Ala Leu Arg Arg Leu Val Leu Arg
            355                 360                 365

Val Cys Ser Glu Ser Glu Thr Tyr Tyr Lys Trp Thr Ala Ser Glu Phe
    370                 375                 380

Thr Gly Ala Phe Gln Gln Asp Trp Trp Pro Val Ser Gly Thr Glu Tyr
385                 390                 395                 400

Pro Leu Cys Thr Ile Lys Met Glu Pro Glu Phe Glu Asn Pro Thr Val
                405                 410                 415

Glu Val Trp Ser Trp Lys Ala Thr Ile Pro Thr Ala Gly Thr Leu Lys
                420                 425                 430

Asp Tyr Phe Gly Leu Ser Ser Gly Gln Gln Trp Lys Asp Thr Asp Phe
            435                 440                 445

Gly Arg Leu Gln Leu Pro Arg Ser Ser His Asn Val Asp Phe Gly His
    450                 455                 460

Lys Ala Arg Phe Gly Pro Phe Cys Val Lys Lys Pro Pro Val Glu Phe
465                 470                 475                 480

Arg Asp Ser Ala Pro Asn Pro Leu Asn Ile Trp Val Lys Tyr Thr Phe
                485                 490                 495

Tyr Phe Gln Phe Gly Met Tyr Gln Pro Thr Gly Ile Gln Asp
            500                 505                 510

Pro Cys Thr Ser Asn Pro Thr Tyr Pro Val Arg Met Val Gly Ala Val
            515                 520                 525

Thr His Pro Lys Tyr Ala Gly Gln Gly Gly Ile Ala Thr Gln Ile Gly
            530                 535                 540

Asp Gln Gly Ile Thr Ala Ala Ser Leu Arg Ala Ile Ser Ala Ala Pro
545                 550                 555                 560

Pro Asn Thr Tyr Thr Gln Ser Ala Phe Leu Lys Ala Pro Glu Thr Glu
                565                 570                 575
```

```
Lys Glu Glu Arg Glu Ser Glu Thr Ser Phe Thr Ser Ala Glu Ser
            580                 585                 590
Ser Ser Glu Gly Asp Gly Ser Ser Asp Asp Gln Ala Glu Arg Arg Ala
        595                 600                 605
Ala Arg Lys Arg Val Ile Lys Leu Leu Leu Lys Arg Leu Ala Asp Arg
610                 615                 620
Pro Val Asp Asn Lys Arg Arg Arg Phe Ser Glu
625                 630                 635

<210> SEQ ID NO 55
<211> LENGTH: 73
<212> TYPE: PRT
<213> ORGANISM: Torque teno virus

<400> SEQUENCE: 55

Met Lys Glu Lys Asp Tyr Trp Glu Ala Trp Leu Thr Ser Cys Thr
1               5                   10                  15
Ser Ile His Asp His His Cys Asp Cys Gly Ser Trp Arg Asp His Leu
            20                  25                  30
Trp Thr Leu Cys Ala Leu Asp Asp Ala Asp Leu Ala Ala Ala Ala Asp
        35                  40                  45
Ile Ile Glu Arg Glu Glu Ala Asp Gly Gly Glu Asp Phe Gly Phe Val
    50                  55                  60
Asp Gly Asp Pro Gly Asp Ala Gly Gly
65                  70

<210> SEQ ID NO 56
<211> LENGTH: 2872
<212> TYPE: DNA
<213> ORGANISM: Torque teno virus
<220> FEATURE:
<221> NAME/KEY: misc_feature
<222> LOCATION: (2719)..(2732)
<223> OTHER INFORMATION: n is a, c, g, or t

<400> SEQUENCE: 56
tacactttgg ggttcaggag gctcaatttg gctcgcttcg ctcgcaccac gtttgctgcc      60
aggcggacct gattgaagac tgaaaaccgt taaattcaaa attgaaaagg gcgggcaaaa     120
tggcggacag ggggcggagt ttatgcaaat taatttatgc aaagtaggag gagctcgatt     180
ttaatttatg caaagtagga ggagtcaaat ctgattggtc gggagctcaa gtcctcattt     240
gcatagggtg taaccaatca gaattaaggc gttcccacga aagcgaatat aagtaggtga     300
ggttccgaat ggctgagttt atgccgccag cggtagacag aactgtctag cgactgggcg     360
ggtgccggag gatccctgat ccggagtcaa ggggcctatc gggcaggagc agctaggcgg     420
agggcctatg ccggaacact gggaggaagc ctggttggaa gctaccaagg gctggcacga     480
tctcgactgc cgctgcggta actggcagga ccacctatgg ctcctactcg ccgatggaga     540
cgccgctttg gccgccgccg tagacgctat agaaagagac gctatggctg agacgacgc      600 tactaccgct acaggccgcg tgactatcgg cgacgatggc tggtaaggag aaggcggcgt     660
tccgtctacc gtagaggtgg acgtagagcg cgccccctacc gactgtttaa tccaaaagta    720
atgcggagag tagtaattag ggggtggtgg cctatttttac aatgcttaaa aggacaggag    780
gcactaagat atagacctct acagtgggac acagagagac agtggagagt gagatcagac    840
ttcgaagacc agtacggata cctcgtacaa tacgggggag gttggggaag tggtgatgtg    900
acacttgaag gtctctacca agagcactta ttgtggagaa actcttggtc taaaggaaac    960
```

```
gatggaatgg acctagtaag atactttgga tgtgtagtat acctatatcc actaaaggac    1020
caggactatt ggttctggtg ggacacggac ttcaaagaat tatatgcaga aaacataaag    1080
gaatacagcc aaccatcagt aatgatgatg gcaaaaagaa caagaatagt aatagccaga    1140
gaaagggcac cacatagaag aaaagtaaga aaaatattta ttccgccacc ttcgagagac    1200
acaacacagt ggcagtttca gacagatttc tgcaatagaa agttatttac gtgggcagct    1260
ggtctaatag acatgcaaaa accgttcgat gctaatggag cctttagaaa tgcttggtgg    1320
ctggaacaga gaaatgatca gggagaaatg aaatacatag aactgtgggg aagagtaccc    1380
ccacaaggag attcagagct gcccaaaaaa aaagaattct ccacaggaac agataaccca    1440
aactacaatg ttcaggacaa tgaggagaaa acatatacc ccattataat atacgtagac    1500
caaaaagatc aaaaccaag aaaaaagtac tgcgtatgtt ataataagac cctcaacaga    1560
tggagactag acaggcaag tactctaaag ataggaaacc tgaaaggact agtactaaga    1620
cagctgatga atcaagaaat gacgtatata tggaaagaag gagaatacag tgcccccttt    1680
gtacaaaggt ggaaaggcag cagattcgct gtgatagacg caagaaaggc agaccaagaa    1740
aacccgaaag tatcaacatg gccaattgag ggaacgtgga acacacagga cacagtactg    1800
aaggatgtat tcggtattaa cttgcaaaat caacaattta gggcggcgga ctttggtaaa    1860
ctcacactac caaaatcacc gcatgactta gacttcggtc accacagcag atttgggcca    1920
ttttgtgtga aaaatgaacc actggagttt caggtatacc ctccagaacc aactaacttg    1980
tggtttcagt acagattttt ctttcagttt ggaggtgaat accaaccccc cacaggaatc    2040
cgggatccat gcgttgatac accagcctat cctgtgccgc agtcaggaag tattacacac    2100
cccaaattcg ccggaaaagg aggaatgctc acggaaacag accgttgggg tatcactgct    2160
gcctcttcca gagccctcag tgcagataca cccacagagg cagcgcaaag tgcacttctc    2220 cgagggact cggaagcgaa aggagaggaa accgaggaaa ccgcgtcatc gtccagtatc    2280
acgagtgccg aaagctctac tgagggagat ggatcgtctg atgatgaaga gacaatcaga    2340
cgcagaagga ggacctggaa gcgactcaga cgaatggtca gagagcagct tgaccgacga    2400
atggaccaca agcgacagcg acttcattga cacccccata agagaaagat gcctcaataa    2460
aaaacaaaag aaacgctaaa cagtgtccga ttactaatgg ggggggggtcc gggggggggct    2520 tgccccccg caagctgggt taccgcacta actccctgcc aagtgaaact cggggacgag    2580
tgagtgcggg acatcccgtg taatggctac ataactaccc ggctttgctt cgacagtggc    2640
cgtggctcga ccctcacaca acactgcagg taggggcgc aattgggatc gttagaaaac    2700
tatggccgag catgggggnn nnnnnnnnnn nnccaacccc ccggtgggg gggccaaggc    2760 ccccctaca ccccccatg gggggctgcc gcccccaaa ccccccgcgt cggatggggg    2820
gggctgcgcc cccccaaac cccccttgcc cggggctgtg ccccggaccc cc            2872
```

<210> SEQ ID NO 57
<211> LENGTH: 637
<212> TYPE: PRT
<213> ORGANISM: Torque teno virus

<400> SEQUENCE: 57

```
Met Ala Pro Thr Arg Arg Trp Arg Arg Phe Gly Arg Arg Arg Arg
1               5                   10                  15

Arg Tyr Arg Lys Arg Arg Tyr Gly Trp Arg Arg Arg Tyr Tyr Arg Tyr
            20                  25                  30
```

```
Arg Pro Arg Asp Tyr Arg Arg Trp Leu Val Arg Arg Arg Arg
         35                  40                  45

Ser Val Tyr Arg Arg Gly Gly Arg Arg Ala Arg Pro Tyr Arg Leu Phe
 50                      55                  60

Asn Pro Lys Val Met Arg Arg Val Val Ile Arg Gly Trp Trp Pro Ile
 65                  70                  75                  80

Leu Gln Cys Leu Lys Gly Gln Glu Ala Leu Arg Tyr Arg Pro Leu Gln
                 85                  90                  95

Trp Asp Thr Glu Arg Gln Trp Arg Val Arg Ser Asp Phe Glu Asp Gln
            100                 105                 110

Tyr Gly Tyr Leu Val Gln Tyr Gly Gly Trp Gly Ser Gly Asp Val
            115                 120                 125

Thr Leu Glu Gly Leu Tyr Gln Glu His Leu Leu Trp Arg Asn Ser Trp
130                 135                 140

Ser Lys Gly Asn Asp Gly Met Asp Leu Val Arg Tyr Phe Gly Cys Val
145                 150                 155                 160

Val Tyr Leu Tyr Pro Leu Lys Asp Gln Asp Tyr Trp Phe Trp Trp Asp
                165                 170                 175

Thr Asp Phe Lys Glu Leu Tyr Ala Glu Asn Ile Lys Glu Tyr Ser Gln
            180                 185                 190

Pro Ser Val Met Met Met Ala Lys Arg Thr Arg Ile Val Ile Ala Arg
            195                 200                 205

Glu Arg Ala Pro His Arg Arg Lys Val Arg Lys Ile Phe Ile Pro Pro
210                 215                 220

Pro Ser Arg Asp Thr Thr Gln Trp Gln Phe Gln Thr Asp Phe Cys Asn
225                 230                 235                 240

Arg Lys Leu Phe Thr Trp Ala Ala Gly Leu Ile Asp Met Gln Lys Pro
                245                 250                 255

Phe Asp Ala Asn Gly Ala Phe Arg Asn Ala Trp Trp Leu Glu Gln Arg
            260                 265                 270

Asn Asp Gln Gly Glu Met Lys Tyr Ile Glu Leu Trp Gly Arg Val Pro
            275                 280                 285

Pro Gln Gly Asp Ser Glu Leu Pro Lys Lys Lys Glu Phe Ser Thr Gly
290                 295                 300

Thr Asp Asn Pro Asn Tyr Asn Val Gln Asp Asn Glu Glu Lys Asn Ile
305                 310                 315                 320

Tyr Pro Ile Ile Ile Tyr Val Asp Gln Lys Asp Gln Lys Pro Arg Lys
                325                 330                 335

Lys Tyr Cys Val Cys Tyr Asn Lys Thr Leu Asn Arg Trp Arg Leu Gly
            340                 345                 350

Gln Ala Ser Thr Leu Lys Ile Gly Asn Leu Lys Gly Leu Val Leu Arg
            355                 360                 365

Gln Leu Met Asn Gln Glu Met Thr Tyr Ile Trp Lys Glu Gly Glu Tyr
            370                 375                 380

Ser Ala Pro Phe Val Gln Arg Trp Lys Gly Ser Arg Phe Ala Val Ile
385                 390                 395                 400

Asp Ala Arg Lys Ala Asp Gln Glu Asn Pro Lys Val Ser Thr Trp Pro
                405                 410                 415

Ile Glu Gly Thr Trp Asn Thr Gln Asp Thr Val Leu Lys Asp Val Phe
            420                 425                 430

Gly Ile Asn Leu Gln Asn Gln Gln Phe Arg Ala Ala Asp Phe Gly Lys
            435                 440                 445

Leu Thr Leu Pro Lys Ser Pro His Asp Leu Asp Phe Gly His His Ser
```

```
                450             455             460
Arg Phe Gly Pro Phe Cys Val Lys Asn Glu Pro Leu Glu Phe Gln Val
465                 470                 475                 480

Tyr Pro Pro Glu Pro Thr Asn Leu Trp Phe Gln Tyr Arg Phe Phe Phe
                485                 490                 495

Gln Phe Gly Gly Glu Tyr Gln Pro Pro Thr Gly Ile Arg Asp Pro Cys
            500                 505                 510

Val Asp Thr Pro Ala Tyr Pro Val Pro Gln Ser Gly Ser Ile Thr His
        515                 520                 525

Pro Lys Phe Ala Gly Lys Gly Gly Met Leu Thr Glu Thr Asp Arg Trp
    530                 535                 540

Gly Ile Thr Ala Ala Ser Ser Arg Ala Leu Ser Ala Asp Thr Pro Thr
545                 550                 555                 560

Glu Ala Ala Gln Ser Ala Leu Leu Arg Gly Asp Ser Glu Ala Lys Gly
                565                 570                 575

Glu Glu Thr Glu Glu Thr Ala Ser Ser Ser Ile Thr Ser Ala Glu
            580                 585                 590

Ser Ser Thr Glu Gly Asp Gly Ser Ser Asp Glu Glu Thr Ile Arg
        595                 600                 605

Arg Arg Arg Arg Thr Trp Lys Arg Leu Arg Arg Met Val Arg Glu Gln
610                 615                 620

Leu Asp Arg Arg Met Asp His Lys Arg Gln Arg Leu His
625                 630                 635

<210> SEQ ID NO 58
<211> LENGTH: 72
<212> TYPE: PRT
<213> ORGANISM: Torque teno virus

<400> SEQUENCE: 58

Met Pro Glu His Trp Glu Glu Ala Trp Leu Glu Ala Thr Lys Gly Trp
1               5                   10                  15

His Asp Leu Asp Cys Arg Cys Gly Asn Trp Gln Asp His Leu Trp Leu
            20                  25                  30

Leu Leu Ala Asp Gly Asp Ala Ala Leu Ala Ala Val Asp Ala Ile
        35                  40                  45

Glu Arg Asp Ala Met Ala Gly Asp Asp Ala Thr Thr Ala Thr Gly Arg
50                  55                  60

Val Thr Ile Gly Asp Asp Gly Trp
65                  70

<210> SEQ ID NO 59
<211> LENGTH: 2735
<212> TYPE: DNA
<213> ORGANISM: Torque teno virus
<220> FEATURE:
<221> NAME/KEY: misc_feature
<222> LOCATION: (2596)..(2622)
<223> OTHER INFORMATION: n is a, c, g, or t

<400> SEQUENCE: 59
tcatgacagg gttcaccgga agggctgcaa aattacagct aaaaccacaa gtctaacaca      60
ataaaccaca aagtattaca ggaaactgca ataaatttag aaataagtta cacataacca     120
ccaaaccaca ggaaactgtg caaaaaagag gaaataaatt tcattggctg ggcctgaagt     180
cctcattaga ataataaaag aaccaatcag aagaacttcc tcttttagag tatataagta     240
agtgcgcaga cgaatggctg agtttatgcc gctggtggta gacacgaaca gagctgagtg     300
```

```
tctaaccgcc tgggcgggtg ccggagctcc tgagagcgga gtcaaggggc ctatcgggca    360
ggcggtaatc cagcggaacc gggccccccct cgatggaaga aagatggctg acggtagcgt    420
actgcgcaca cggattattc tgcagctgta aagacccgaa aaacatctt gaaaaatgcc     480 ttacagacgc tatcgcagac gccgaagaag accgacacgg agatggaggc accggaggtg    540
gagacgctac tttcgatatc ggtatcgacg cgctcctcgc cgccgccgca caaaggtaag    600
gagacggagg aaaaaagctc cggtcataca atggttccct cctagccgga gaacctgcct    660
catagaggga ttttggccgt tgagctacgg acactggttc cgtacctgtc tccccttttag   720 gcggttaaat ggactagtat tcccgggtgg aggttgtgac tggagccagt ggagtttaca    780
aaacctttac aatgaaaaac ttaactggag aaatatatgg acagctagta atgttggaat    840
ggaattcgct agatttttaa aaggaaagtt ttacttttc agacatccat ggagaaatta    900
tataataact tgggatcaag ataccatg caggccacta ccttatcaaa acctgcatcc     960
actcctaatg ctactaaaaa aacagcacaa aattgtactt tcacagcaaa actgtaaccc   1020
aaacagaaaa caaaaacctg tcacattaaa attcaaacct ccgccaaaac taacatcaca   1080
atggagacta agtagagaat tagcaaagat gccactaata agacttggag taagctttat   1140
agacctaaca gaaccatggg tagaagggtg gggaaatgca ttttattccg tgctaggata   1200
tgaagcagta aaagaccaag gacactggtc aaactggaca caaataaaat actattggat   1260
ctatgacacg ggagtaggaa atgcagtata tgttatacta ttaaaaaaag acgttactga   1320
taatccagga aacatggcaa caacctttaa agcatcagga ggacagcatc cagatgcaat   1380
agatcacatt gaattgataa accaaggatg gccttactgg ttatactttt atggtaaaag   1440
tgaacaagac attaaaaaag aggcacacag cgcagaaata tcaagagaat atactagaga   1500
cccaaaatct aaaaaactaa aaataggaat agtaggatgg gcatcttcaa actacacaac   1560
aacaggcagt gatcaaaaca gtggtggatc aacatcagct atacaaggtg gatatgtagc   1620
atatgcaggg tccggggtca taggagcagg gtcaatagga aatttatatc aacaaggatg   1680
gccatctaat caaaactggc ctaatacaaa cagagacaaa acaaactttg actggggaat   1740
acgaggacta tgtatactca gagataacat gcacttagga agccaagaat tagatgatga   1800
atgcacaatg ctcacattgt tcggaccctt tgtagaaaaa gcaaatccaa tatttgcaac   1860
aacagaccct aaattcttta aacctgaact caaagactat aatataatca tgaaatatgc   1920
ctttaaattt cagtggggag acatggcac agaaagattt aaaaccaaca tcggagaccc   1980
cagcaccata ccctgcccct cgaaccccgg ggaccgcttc cacagcggga tacaagaccc   2040
ctccaaggta caaaacaccg tcctcaaccc ctgggactat gactgtgatg ggattgttag   2100
aaaagatact ctcaaaagac ttctcgaact ccccacagag acagaggagg aggagaaggc   2160
gtacccactc cttggacaaa aaacagagaa agagccatta tcagactccg acgaagagag   2220
cgttatctca agcacgagca gtggatcctc tcaagaagaa gaaacgcaga gacgaagaca   2280
ccacaagcca agcaagcgac gactcctcaa gcacctccag cgggtggtaa agaggatgaa   2340
aacactgtga tagataaata tagaaaccta gcagacccct cactcaatgt cacaggacac   2400
atggaaaaat tcatgcagtt acatattcaa acgtacaag aaataagagc taaaaatgct    2460
aaaaaatccc tcaataaact ttacttttct gattaatagc ggcctcctgt gtccaaccta   2520
ttttccctaa acccttcaa aatgcgggg gggacacaaa atggcggagg gactaaggggg   2580 ggggcaagcc ccctnnnnn nnnnnnnnnn nnnnnnnnnn nngggggggcg accccccgc    2640
```

```
acccccccct gcgggggctc cgcccctgc accccgggaa gggggggaaa cccccctca    2700 accccccgcg ggggcaagc ccccctgcac ccccc                              2735
```

<210> SEQ ID NO 60
<211> LENGTH: 624
<212> TYPE: PRT
<213> ORGANISM: Torque teno virus

<400> SEQUENCE: 60

```
Met Pro Tyr Arg Arg Tyr Arg Arg Arg Arg Pro Thr Arg Arg
 1               5                  10                  15

Trp Arg His Arg Arg Trp Arg Arg Tyr Phe Arg Tyr Arg Tyr Arg Arg
                20                  25                  30

Ala Pro Arg Arg Arg Thr Lys Val Arg Arg Arg Lys Lys Ala
                35                  40                  45

Pro Val Ile Gln Trp Phe Pro Pro Ser Arg Arg Thr Cys Leu Ile Glu
 50                  55                  60

Gly Phe Trp Pro Leu Ser Tyr Gly His Trp Phe Arg Thr Cys Leu Pro
65                  70                  75                  80

Phe Arg Arg Leu Asn Gly Leu Val Phe Pro Gly Gly Gly Cys Asp Trp
                85                  90                  95

Ser Gln Trp Ser Leu Gln Asn Leu Tyr Asn Glu Lys Leu Asn Trp Arg
                100                 105                 110

Asn Ile Trp Thr Ala Ser Asn Val Gly Met Glu Phe Ala Arg Phe Leu
                115                 120                 125

Lys Gly Lys Phe Tyr Phe Phe Arg His Pro Trp Arg Asn Tyr Ile Ile
                130                 135                 140

Thr Trp Asp Gln Asp Ile Pro Cys Arg Pro Leu Pro Tyr Gln Asn Leu
145                 150                 155                 160

His Pro Leu Leu Met Leu Leu Lys Lys Gln His Lys Ile Val Leu Ser
                165                 170                 175

Gln Gln Asn Cys Asn Pro Asn Arg Lys Gln Lys Pro Val Thr Leu Lys
                180                 185                 190

Phe Lys Pro Pro Lys Leu Thr Ser Gln Trp Arg Leu Ser Arg Glu
                195                 200                 205

Leu Ala Lys Met Pro Leu Ile Arg Leu Gly Val Ser Phe Ile Asp Leu
210                 215                 220

Thr Glu Pro Trp Val Glu Gly Trp Gly Asn Ala Phe Tyr Ser Val Leu
225                 230                 235                 240

Gly Tyr Glu Ala Val Lys Asp Gln Gly His Trp Ser Asn Trp Thr Gln
                245                 250                 255

Ile Lys Tyr Tyr Trp Ile Tyr Asp Thr Gly Val Gly Asn Ala Val Tyr
                260                 265                 270

Val Ile Leu Leu Lys Lys Asp Val Thr Asp Asn Pro Gly Asn Met Ala
                275                 280                 285

Thr Thr Phe Lys Ala Ser Gly Gly Gln His Pro Asp Ala Ile Asp His
                290                 295                 300

Ile Glu Leu Ile Asn Gln Gly Trp Pro Tyr Trp Leu Tyr Phe Tyr Gly
305                 310                 315                 320

Lys Ser Glu Gln Asp Ile Lys Lys Glu Ala His Ser Ala Glu Ile Ser
                325                 330                 335

Arg Glu Tyr Thr Arg Asp Pro Lys Ser Lys Leu Lys Ile Gly Ile
                340                 345                 350

Val Gly Trp Ala Ser Ser Asn Tyr Thr Thr Thr Gly Ser Asp Gln Asn
```

```
              355                 360                 365
Ser Gly Gly Ser Thr Ser Ala Ile Gln Gly Gly Tyr Val Ala Tyr Ala
            370                 375                 380

Gly Ser Gly Val Ile Gly Ala Gly Ser Ile Gly Asn Leu Tyr Gln Gln
385                 390                 395                 400

Gly Trp Pro Ser Asn Gln Asn Trp Pro Asn Thr Asn Arg Asp Lys Thr
                405                 410                 415

Asn Phe Asp Trp Gly Ile Arg Gly Leu Cys Ile Leu Arg Asp Asn Met
            420                 425                 430

His Leu Gly Ser Gln Glu Leu Asp Asp Glu Cys Thr Met Leu Thr Leu
        435                 440                 445

Phe Gly Pro Phe Val Glu Lys Ala Asn Pro Ile Phe Ala Thr Thr Asp
    450                 455                 460

Pro Lys Phe Phe Lys Pro Glu Leu Lys Asp Tyr Asn Ile Ile Met Lys
465                 470                 475                 480

Tyr Ala Phe Lys Phe Gln Trp Gly Gly His Gly Thr Glu Arg Phe Lys
                485                 490                 495

Thr Asn Ile Gly Asp Pro Ser Thr Ile Pro Cys Pro Phe Glu Pro Gly
            500                 505                 510

Asp Arg Phe His Ser Gly Ile Gln Asp Pro Ser Lys Val Gln Asn Thr
        515                 520                 525

Val Leu Asn Pro Trp Asp Tyr Asp Cys Asp Gly Ile Val Arg Lys Asp
    530                 535                 540

Thr Leu Lys Arg Leu Leu Glu Leu Pro Thr Glu Thr Glu Glu Glu Glu
545                 550                 555                 560

Lys Ala Tyr Pro Leu Leu Gly Gln Lys Thr Glu Lys Glu Pro Leu Ser
                565                 570                 575

Asp Ser Asp Glu Glu Ser Val Ile Ser Ser Thr Ser Ser Gly Ser Ser
            580                 585                 590

Gln Glu Glu Glu Thr Gln Arg Arg His His Lys Pro Ser Lys Arg
        595                 600                 605

Arg Leu Leu Lys His Leu Gln Arg Val Val Lys Arg Met Lys Thr Leu
    610                 615                 620

<210> SEQ ID NO 61
<211> LENGTH: 68
<212> TYPE: PRT
<213> ORGANISM: Torque teno virus

<400> SEQUENCE: 61

Met Glu Glu Arg Trp Leu Thr Val Ala Tyr Cys Ala His Gly Leu Phe
1               5                   10                  15

Cys Ser Cys Lys Asp Pro Lys Lys His Leu Glu Lys Cys Leu Thr Asp
            20                  25                  30

Ala Ile Ala Asp Ala Glu Glu Asp Arg His Gly Asp Gly Gly Thr Gly
        35                  40                  45

Gly Gly Asp Ala Thr Phe Asp Ile Gly Ile Asp Ala Leu Leu Ala Ala
    50                  55                  60

Ala Ala Gln Arg
65

<210> SEQ ID NO 62
<211> LENGTH: 625
<212> TYPE: PRT
<213> ORGANISM: Torque teno virus
```

<400> SEQUENCE: 62

```
Met Pro Tyr Arg Arg Tyr Arg Arg Arg Arg Pro Thr Arg Arg
1               5                   10                  15

Trp Arg His Arg Arg Trp Arg Arg Tyr Phe Arg Tyr Arg Tyr Arg Arg
                20                  25                  30

Ala Pro Arg Arg Arg Ala Lys Val Arg Arg Arg Arg Lys Ala
            35                  40                  45

Pro Val Ile Gln Trp Asn Pro Pro Ser Arg Arg Thr Cys Leu Ile Glu
50                  55                  60

Gly Phe Trp Pro Leu Ser Tyr Gly His Trp Phe Arg Thr Cys Leu Pro
65                  70                  75                  80

Met Arg Arg Leu Asn Gly Leu Ile Phe Thr Gly Gly Cys Asp Trp
                85                  90                  95

Thr Gln Trp Ser Leu Gln Asn Leu Phe His Glu Lys Leu Asn Trp Arg
                100                 105                 110

Asn Ile Trp Thr Ala Ser Asn Val Gly Met Glu Phe Ala Arg Phe Leu
                115                 120                 125

Arg Gly Lys Phe Tyr Phe Phe Arg His Pro Trp Arg Ser Tyr Ile Val
                130                 135                 140

Thr Trp Asp Gln Asp Ile Pro Cys Lys Pro Leu Pro Tyr Gln Asn Leu
145                 150                 155                 160

Gln Pro Leu Leu Met Leu Leu Lys Lys Gln His Lys Leu Val Leu Ser
                165                 170                 175

Gln Lys Asp Cys Asn Pro Ser Arg Lys Gln Lys Pro Val Thr Leu Lys
                180                 185                 190

Phe Arg Pro Pro Pro Lys Leu Thr Ser Gln Trp Arg Leu Ser Arg Glu
                195                 200                 205

Leu Ser Lys Ile Pro Leu Ile Arg Leu Gly Ile Ser Leu Ile Asp Leu
                210                 215                 220

Ser Glu Pro Trp Leu Glu Gly Trp Gly Asn Ala Phe Tyr Ser Val Leu
225                 230                 235                 240

Gly Tyr Glu Ala Ser Lys His Ser Gly Arg Trp Ser Asn Trp Thr Gln
                245                 250                 255

Met Lys Tyr Phe Trp Ile Tyr Asp Thr Gly Val Gly Asn Ala Val Tyr
                260                 265                 270

Val Ile Leu Leu Lys Lys Asp Val Asp Asn Pro Gly Asp Met Ala
                275                 280                 285

Thr Lys Phe Val Thr Gly Gln Gly Gln His Pro Asp Ala Ile Asp His
                290                 295                 300

Ile Glu Met Val Asn Glu Gly Trp Pro Tyr Trp Leu Phe Phe Tyr Gly
305                 310                 315                 320

Gln Ser Glu Gln Asp Ile Lys Lys Leu Ala His Asp Gln Asp Ile Ala
                325                 330                 335

Arg Glu Tyr Ala Arg Asp Pro Lys Ser Lys Lys Leu Lys Ile Gly Val
                340                 345                 350

Ile Gly Trp Ala Ser Ser Asn Tyr Thr Thr Ala Gly Ser Asn Gln Asn
                355                 360                 365

Thr Thr Ala Gln Thr Pro Glu Ala Ile Gln Gly Tyr Val Ala Tyr
                370                 375                 380

Ala Gly Ser Arg Ile Pro Gly Ala Gly Ser Ile Thr Asn Leu Phe Gln
385                 390                 395                 400

Met Gly Trp Pro Gly Asp Gln Asn Trp Pro Pro Thr Asn Gln Glu Gln
                405                 410                 415
```

```
Thr Asn Phe Asn Trp Gly Leu Arg Gly Leu Cys Val Leu Arg Asp Asn
            420                 425                 430

Met Lys Leu Gly Ala Gln Glu Leu Asp Asp Glu Cys Thr Met Leu Ser
        435                 440                 445

Leu Phe Gly Pro Phe Val Glu Lys Ala Asn Thr Ala Phe Ala Thr Asn
    450                 455                 460

Asp Pro Lys Tyr Phe Arg Pro Glu Leu Lys Asp Tyr Asn Val Val Met
465                 470                 475                 480

Lys Tyr Ala Phe Lys Phe Gln Trp Gly Gly His Gly Thr Glu Arg Phe
                485                 490                 495

Lys Thr Thr Ile Gly Asp Pro Ser Thr Ile Pro Cys Pro Phe Glu Pro
            500                 505                 510

Gly Glu Arg Tyr His His Gly Val Gln Asp Pro Ala Lys Val Gln Asn
        515                 520                 525

Thr Val Leu Asn Pro Trp Asp Tyr Asp Cys Asp Gly Ile Val Arg Thr
        530                 535                 540

Asp Thr Leu Lys Arg Leu Leu Glu Leu Pro Thr Glu Thr Glu Glu Thr
545                 550                 555                 560

Glu Lys Ala Tyr Pro Leu Leu Gly Gln Lys Thr Glu Lys Glu Pro Leu
                565                 570                 575

Ser Asp Ser Asp Glu Glu Ser Val Ile Ser Ser Thr Ser Ser Gly Ser
                580                 585                 590

Ser Gln Glu Glu Glu Thr Gln Arg Arg Arg Gln His Lys Pro Ser Lys
        595                 600                 605

Arg Arg Leu Leu Lys His Leu Gln Arg Val Val Lys Arg Met Lys Thr
    610                 615                 620

Leu
625
```

What is claimed is:

1. A vaccine comprising at least one adjuvant in an immunologically effective amount and a Porcine Torque Teno Virus open reading frame 1 (ORF1) protein according to SEQ ID NO: 16, or an immunogenic fragment of the ORF1 protein according to SEQ ID NO: 16 that comprises subtype specific hypervariable regions (HVR) represented by amino acids 363 to 375 and 388 to 423 of SEQ ID NO: 16.

2. The vaccine according to claim 1, wherein ORF1 protein or immunogenic fragment of the ORF1 protein is a purified plasmid or baculovirus vector expressed recombinant protein.

3. The vaccine according to claim 1, further comprising at least one physiologically acceptable carrier.

4. The vaccine according to claim 1, wherein the adjuvant is selected from one or more of aluminum hydroxide (alum), aluminum potassium sulfate, immunostimulating complexes (ISCOMS), non-ionic block polymers or copolymers, cytokines, saponins, monophosphoryl lipid A (MLA), muramyl dipeptides (MDP), enterotoxins isolated from *Escherichia coli*, cholera toxins, diphtheria toxin, tetanus toxin, pertussis toxin, and subunits of cholera, diphtheria, tetanus, and pertussis toxins.

5. A vaccine for protecting against a Porcine Torque Teno Virus (PTTV) infection, wherein the vaccine comprises at least one adjuvant and a recombinant protein comprising amino acids 310 to 625 of SEQ ID NO: 16.

6. The vaccine according to claim 1, which is adapted to be administered parenterally, intranasally, intradermally, or transdermally to a pig.

7. The vaccine according to claim 1, which is adapted to be administered intralymphoidly or intramuscularly to a pig.

8. An immunogenic composition comprising at least one adjuvant and a recombinant subunit capsid protein or immunogenic fragment thereof expressed from a bacterial or baculovirus expression system wherein the capsid protein or immunogenic fragment thereof comprises a Porcine Torque Teno Virus polypeptide represented by amino acids 363 to 375 of SEQ ID NO: 16 and a Porcine Torque Teno Virus polypeptide represented by amino acids 388 to 423 of SEQ ID NO: 16.

9. The immunogenic composition according to claim 8, which is adapted to be administered parenterally, intranasally, intradermally, transdermally, intralymphoidly or intramuscularly to a pig.

10. A plasmid or baculovirus vector encoding a recombinant capsid protein or immunogenic fragment thereof wherein the recombinant capsid protein or immunogenic fragment comprises a Porcine Torque Teno Virus polypeptide represented by amino acids 363 to 375 of SEQ ID NO: 16 and a Porcine Torque Teno Virus polypeptide represented by amino acids 388 to 423 of SEQ ID NO: 16.

11. The plasmid or baculovirus vector of claim 10, wherein the recombinant capsid protein or immunogenic fragment thereof comprises amino acids 310 to 625 of SEQ ID NO: 16.

* * * * *